US008301229B2

(12) United States Patent
Gono et al.

(10) Patent No.: US 8,301,229 B2
(45) Date of Patent: *Oct. 30, 2012

(54) BIOLOGICAL OBSERVATION DISPLAY APPARATUS FOR PRESENTING COLOR OR SPECTRAL IMAGES

(75) Inventors: Kazuhiro Gono, Sagamihara (JP); Shoichi Amano, Hachioji (JP); Tomoya Takahashi, Hachioji (JP); Mutsumi Ohshima, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 1303 days.

This patent is subject to a terminal disclaimer.

(21) Appl. No.: 11/914,171

(22) PCT Filed: Mar. 14, 2006

(86) PCT No.: PCT/JP2006/305023
§ 371 (c)(1),
(2), (4) Date: Dec. 13, 2007

(87) PCT Pub. No.: WO2006/120798
PCT Pub. Date: Nov. 16, 2006

(65) Prior Publication Data
US 2009/0023991 A1 Jan. 22, 2009

(30) Foreign Application Priority Data

May 12, 2005 (JP) .................. 2005-140379
May 12, 2005 (JP) .................. 2005-140383

(51) Int. Cl.
*A61B 6/00* (2006.01)
(52) U.S. Cl. ........ 600/473; 600/101; 600/407; 600/476; 356/300; 356/302; 356/303; 356/939
(58) Field of Classification Search .................. 600/407, 600/473, 476, 101; 356/300, 302, 303, 939
See application file for complete search history.

(56) References Cited

U.S. PATENT DOCUMENTS
4,885,634 A 12/1989 Yabe
(Continued)

FOREIGN PATENT DOCUMENTS
EP 1 302 152 4/2003
(Continued)

OTHER PUBLICATIONS
Machine Translation of JP 2003-093336.*
(Continued)

*Primary Examiner* — James Kish
(74) *Attorney, Agent, or Firm* — Scully, Scott, Murphy & Presser, P.C.

(57) ABSTRACT

A biological observation apparatus comprises a color image signal creating section that performs signal processing on either a first image pickup signal for which a subject to be examined illuminated by white illumination light is picked up by a color filter having a transmitting characteristic of a plurality of broadband wavelengths or a second image pickup signal for which a subject to be examined is picked up under illumination of frame sequential illumination lights which cover a visible range, and creates a color image signal. The biological observation apparatus comprises a spectral image signal creating section that creates a spectral image signal corresponding to a narrowband image signal through signal processing on a color image signal based on the first or second image pickup signal. The biological observation apparatus comprises one of a characteristic changing/setting section for a display color converting section that performs conversion of display colors when causing the spectral image signal to be displayed or the like, an interface section for performing an instruction operation for switching and/or confirming information including an image to be displayed, or the like.

22 Claims, 39 Drawing Sheets

U.S. PATENT DOCUMENTS

| | | | |
|---|---|---|---|
| 5,032,913 A | | 7/1991 | Hattori et al. |
| 5,078,150 A | * | 1/1992 | Hara et al. ............... 600/476 |
| 5,408,263 A | * | 4/1995 | Kikuchi et al. ............ 348/68 |
| 6,690,409 B1 | * | 2/2004 | Takahashi .................. 348/65 |
| 2003/0176768 A1 | | 9/2003 | Gono et al. |
| 2005/0068427 A1 | | 3/2005 | Sudo et al. |
| 2005/0073578 A1 | * | 4/2005 | Odlivak et al. ............. 348/65 |

FOREIGN PATENT DOCUMENTS

| | | | |
|---|---|---|---|
| EP | 1 491 132 A1 | | 12/2004 |
| JP | 8-313823 | | 11/1996 |
| JP | 2000-148987 | | 5/2000 |
| JP | 2003-093336 | * | 9/2001 |
| JP | 2002-034893 | | 2/2002 |
| JP | 2002-034908 | | 2/2002 |
| JP | 2002-095635 | | 4/2002 |
| JP | 2003-093336 | | 4/2003 |
| RU | 2 119 660 C1 | | 9/1998 |
| RU | 2 137 114 C1 | | 9/1999 |
| WO | WO 02/07588 | | 1/2002 |

OTHER PUBLICATIONS

Extended Supplementary Partial European Search Report dated Sep. 18, 2009.

Lugovskay S.A. et al., "Laboratory haematology", 2002, Ynimedpress, ISBN: 5-94885-002-1.

European communication mailed Jun. 21, 2012 in corresponding European Patent Application No. 06729057.7.

* cited by examiner

| R | G | R | G |
|---|---|---|---|
| R | B | R | B |
| R | G | R | G |
| R | B | R | B |

FROM COEFFICIENT SETTING SWITCH

FIG.32
(A)
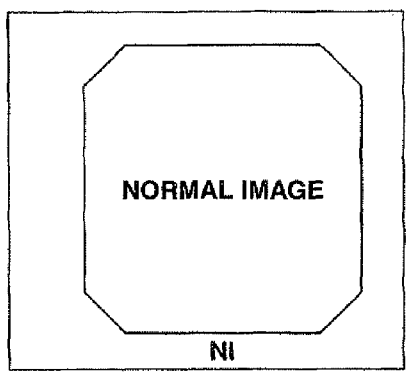
(B)
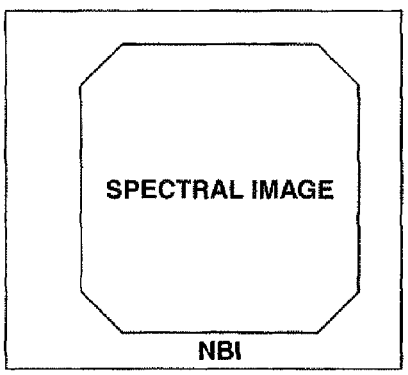
(C)
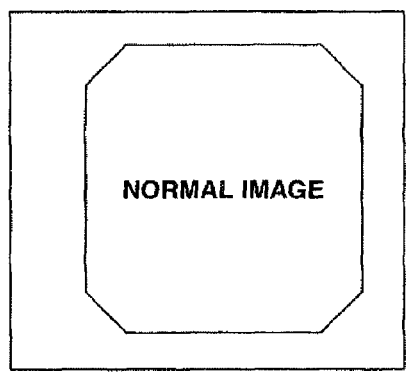
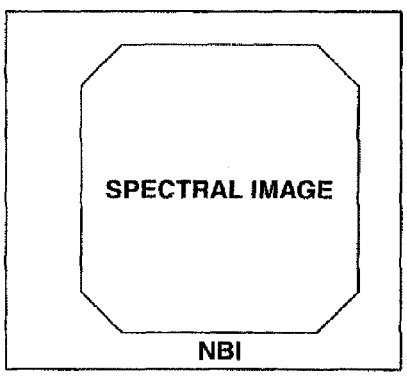
(D)
(E)
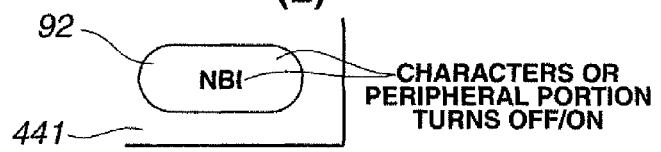
(F)
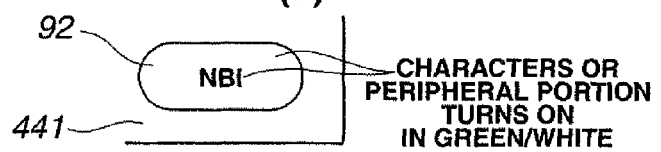

FIG.47
(A)
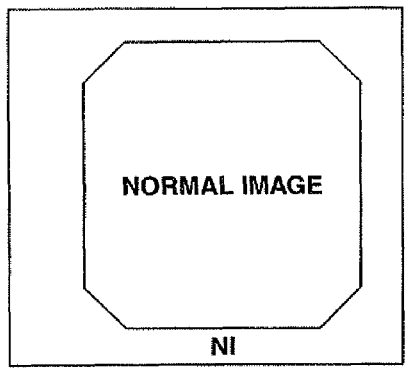
NORMAL IMAGE
NI
(B)
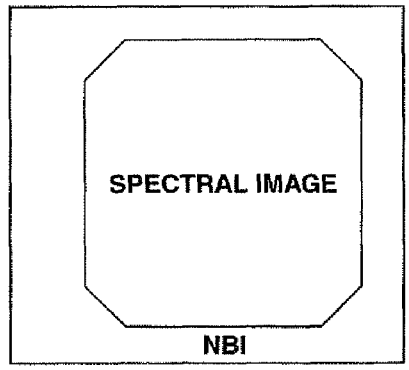
SPECTRAL IMAGE
NBI
(C)
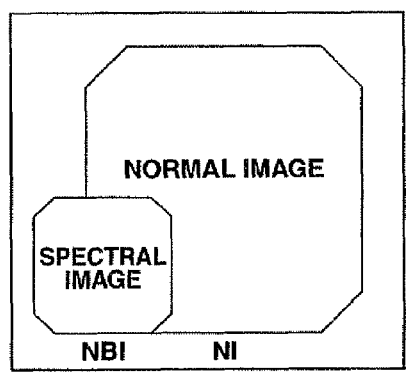
NORMAL IMAGE
SPECTRAL IMAGE
NBI  NI
(D)
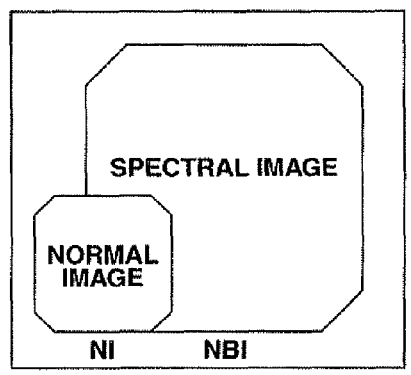
SPECTRAL IMAGE
NORMAL IMAGE
NI  NBI
FIG.48
(A)
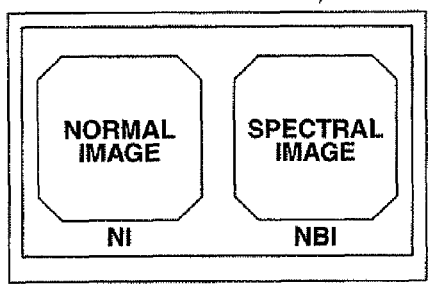
(B)
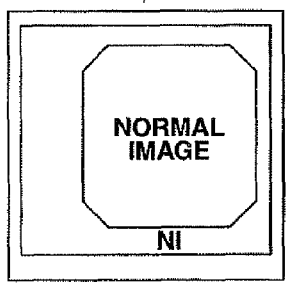
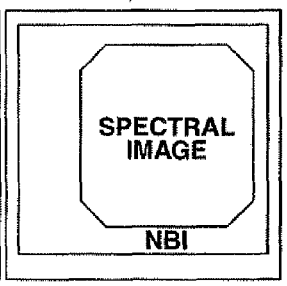

| Mg | G | Mg | G |
| --- | --- | --- | --- |
| Cy | Ye | Cy | Ye |
| G | Mg | G | Mg |
| Cy | Ye | Cy | Ye |

FIG.59
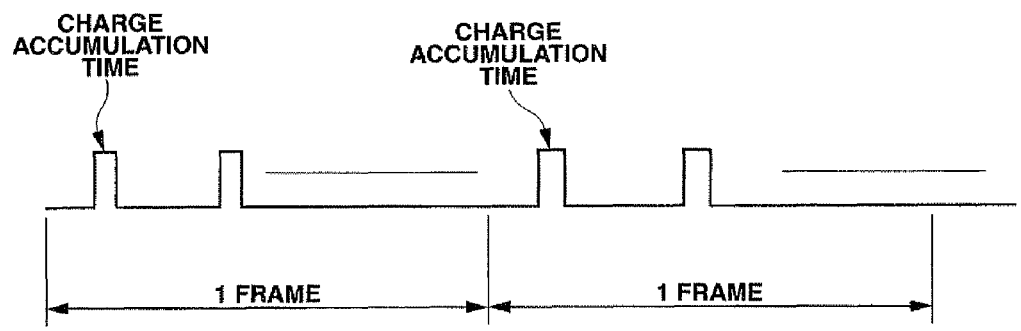
FIG.60
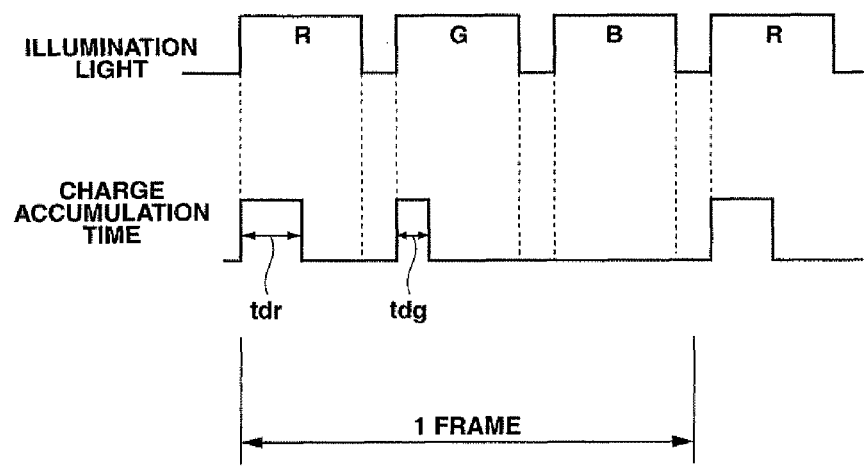
FIG.61
| Mg | G  | Mg | G  |
|----|----|----|----|
| Cy | Ye | Cy | Ye |
| G  | Mg | G  | Mg |
| Cy | Ye | Cy | Ye |

# BIOLOGICAL OBSERVATION DISPLAY APPARATUS FOR PRESENTING COLOR OR SPECTRAL IMAGES

TECHNICAL FIELD

The present invention relates to a biological observation apparatus that creates a spectral image signal corresponding to a quasi-narrowband filter through signal processing using a color image signal obtained by picking up an image of a living body, and displays the spectral image signal as a spectral image on a monitor.

BACKGROUND ART

Conventionally, an endoscope apparatus that irradiates illumination light to obtain an endoscopic image inside a body cavity is widely used as a biological observation apparatus. An endoscope apparatus of this type uses an electronic endoscope having image pickup means that guides illumination light from a light source into a body cavity using a light guide or the like and which picks up a subject image from returning light thereof, and is arranged so that signal processing of an image pickup signal from the image pickup means is performed by a video processor in order to display an endoscopic image on an observation monitor for observing an observed region such as a diseased part.

One method of performing normal biological tissue observation using an endoscope apparatus involves emitting white light in the visible light range from a light source, irradiating frame sequential light on a subject via a rotary filter such as an RGB rotary filter, and obtaining a color image by performing synchronization and image processing on returning light of the frame sequential light by a video processor. In addition, another method of performing normal biological tissue observation using an endoscope apparatus involves positioning a color chip on a front face of an image pickup plane of image pickup means of an endoscope, emitting white light in the visible light range from a light source, picking up images by separating returning light of the frame sequential light at the color chip into each color component, and obtaining a color image by performing image processing by a video processor.

With biological tissue, absorption characteristics and scattering characteristics of light differ according to the wavelength of irradiated light. For example, Japanese Patent Laid-Open 2002-95635 proposes a narrowband light endoscope apparatus that irradiates illumination light in the visible light range on biological tissue as narrowband RGB frame sequential light having discrete spectral characteristics to obtain tissue information on a desired deep portion of the biological tissue.

In addition, Japanese Patent Laid-Open 2003-93336 proposes a narrowband light endoscope apparatus that performs signal processing on an image signal obtained from illumination light in the visible light range to create a discrete spectral image and to obtain tissue information on a desired deep portion of the biological tissue.

With the apparatus described in the above-mentioned Japanese Patent Laid-Open 2003-93336, processing for creating a spectral image signal such as that obtained when using a narrow bandpass filter is performed through electrical arithmetic processing by matrix computation (corresponding to a quasi-narrow bandpass filter) on a color image signal (also referred to as a living body signal) picked up in the broadband wavelength range without using an optical narrow bandpass filter.

However, the apparatus described in the above-mentioned Japanese Patent Laid-Open 2003-93336 has disadvantages including declines in the accuracy of a created spectral image signal, such as a difference in spectral reflection characteristics caused by a difference in biological tissue to be observed creates perturbations in the created spectral image.

For example, in a case where the observation object is the esophagus mucosa or the gastric or large intestinal mucosa, the difference in the type of mucosal tissue (for example, esophagus mucosa is stratified squamous epithelia while gastric mucosa is simple columnar epithelia) gives rise to disadvantages such as a difference in spectral reflection characteristics caused by a difference in mucosal tissue.

In addition, the apparatus described in the above-mentioned Japanese Patent Laid-Open 2003-93336 has a disadvantage in that color tones during output/display of a spectral image signal on display means or a display output device cannot be changed.

As seen, while the apparatus described in the above-mentioned Japanese Patent Laid-Open 2003-93336 has an advantage in that a spectral image signal can be electrically created from a color image signal, it is desired that interface means or the like capable of further enhancing operability is provided, such as converting and displaying a spectral image signal in a color tone desired by a user or an appropriate color tone, or switching and displaying a color image signal (normal image signal) and a color image signal.

Furthermore, the apparatus described in the above-mentioned Japanese Patent Laid-Open 2003-93336 simply outputs an obtained spectral image to a monitor. Therefore, with the apparatus described in the above-mentioned Japanese Patent Laid-Open 2003-93336, not only is there a risk in that an image displayed on the monitor may not be an image having color tones suitable for the observation of issue information in a desired deep portion of biological tissue, it becomes difficult to grasp the relationship to living body function information held by a living body such as the hemoglobin content of blood.

The present invention is made in consideration of the above, and an object thereof is to provide a biological observation apparatus having a function for electrically creating a spectral image signal from a color image signal which is also capable of creating a spectral image signal that can appropriately accommodate differences among biological tissue and the like and improving operability related to spectral image observation and the like.

Another object of the present invention is to provide a biological observation apparatus capable of calculating living body function information related to the blood of a living body based on a spectral image signal obtained through signal processing, thereby contributing towards the improvement of diagnostic performance.

DISCLOSURE OF INVENTION

Means for Solving the Problem

A biological observation apparatus according to a first embodiment of the present invention comprises: a color image signal creating section that performs signal processing on either a first image pickup signal for which a subject to be examined illuminated by white illumination light is picked up by a first image pickup apparatus provided with a color filter having a transmitting characteristic of a plurality of broadband wavelengths or a second image pickup signal for which a subject to be examined illuminated by a plurality of mutually different frame sequential illumination lights in a broadband wavelength range which covers a visible range is picked up by a second image pickup apparatus, and creates a color image signal for display as a color image on a display device; a spectral image signal creating section that creates, based on the first image pickup signal or the second image pickup signal, a spectral image signal corresponding to a narrowband image signal obtained upon picking up an image of a subject to be examined illuminated by an illumination light in a narrowband wavelength range through signal processing of a color signal used to create the color image signal or through signal processing of the color image signal; a display color converting section that performs display color conversion on the spectral image signal when displaying the signal as a spectral image on the display device; and at least one of a characteristic setting section that changes/sets creating characteristics of the spectral image signal at the spectral image signal creating section, a display color changing/setting section that changes/sets a display color of the display color converting section, and an interface section for performing instruction operations for switching and/or confirming information including images displayed on the display device.

The above described configuration provides a function for electrically creating a spectral image signal from a color image signal, and is further capable of improving operability by enabling changes in the display color of the spectral image and changes in characteristics of a created spectral image signal according to biological tissue and the like, allowing confirmation of an image displayed on a display device, or the like.

A biological observation apparatus according to a second embodiment of the present invention comprises: a normal image signal creating section that performs signal processing on either a first image pickup signal for which a subject to be examined illuminated by white illumination light is picked up by a first image pickup apparatus provided with a color filter having a transmitting characteristic of a plurality of broadband wavelengths or a second image pickup signal for which a subject to be examined illuminated by a plurality of mutually different frame sequential illumination lights in a broadband wavelength range which covers a visible range is picked up by a second image pickup apparatus, and creates a color image signal for display as a color image on a display device; a spectral image signal creating section that creates, based on the first image pickup signal or the second image pickup signal, a spectral image signal corresponding to a narrowband image signal obtained upon picking up an image of a subject to be examined illuminated by an illumination light in a narrowband wavelength range through signal processing of a color signal used to create the color image signal or through signal processing of the color image signal; and a living body function information calculating section that calculates, in a case where the subject to be examined is a living body, living body function related to the blood of the living body based on the spectral image signal.

The above described configuration enables calculation of living body function information related to the blood of a living body together with a spectral image signal.

BRIEF DESCRIPTION OF THE DRAWINGS

FIG. 29 is a block diagram showing a configuration of an electronic endoscope apparatus in a case where an ID memory is provided at an endoscope or the like;

FIG. 32 is a diagram showing an example in which, when a normal image and a spectral image are displayed, an observation mode is also explicitly displayed;

FIG. 47 is a diagram showing display examples of normal images and spectral images on a display monitor according to the fifth embodiment;

FIG. 48 is a diagram showing display examples of normal images and spectral images on a display monitor according to a modification;

FIG. 59 is a diagram showing charge accumulation time of a CCD shown in FIG. 58;

FIG. 60 is a diagram showing charge accumulation time of a CCD according to a tenth embodiment of the present invention;

FIG. 61 is a diagram showing an array of color filters according to an eleventh embodiment of the present invention;

BEST MODE FOR CARRYING OUT THE INVENTION

Embodiments of the present invention will now be described with reference to the drawings.

First Embodiment

A first embodiment of the present invention will now be described with reference to FIGS. 1 to 34.

An electronic endoscope apparatus as a biological observation apparatus according to the first embodiment of the present invention irradiates illumination light from an illuminating light source to a living body that is a subject to be examined, receives light reflected off the living body based on the illumination light at a solid state image pickup device that is an image pickup section and creates a broadband color image signal from a photoelectrically converted image pickup signal, and creates from the color image signal through signal processing a spectral image signal corresponding to an image signal having a narrowband optical wavelength.

Before presenting a description on the first embodiment of the present invention, a matrix calculating method that forms the foundation of the present invention will be described below. In this case, "matrix" refers to a predetermined coefficient used when creating a spectral image signal from a color image signal obtained in order to create a color image (hereinafter referred to as a normal signal).

In addition, following the description on a matrix, a correcting method for obtaining a more accurate spectral image signal and an S/N improving method that enhances the S/N of a created spectral image signal will be described. The correcting method and the S/N improving method are to be used as needed. Furthermore, in the following description, vectors and matrices shall be denoted using bold characters or <> (for example, matrix A shall be denoted as "bold A" or "<A>"). Other mathematical concepts shall be denoted without character decoration.

(Matrix Calculating Method)

Figure 1:
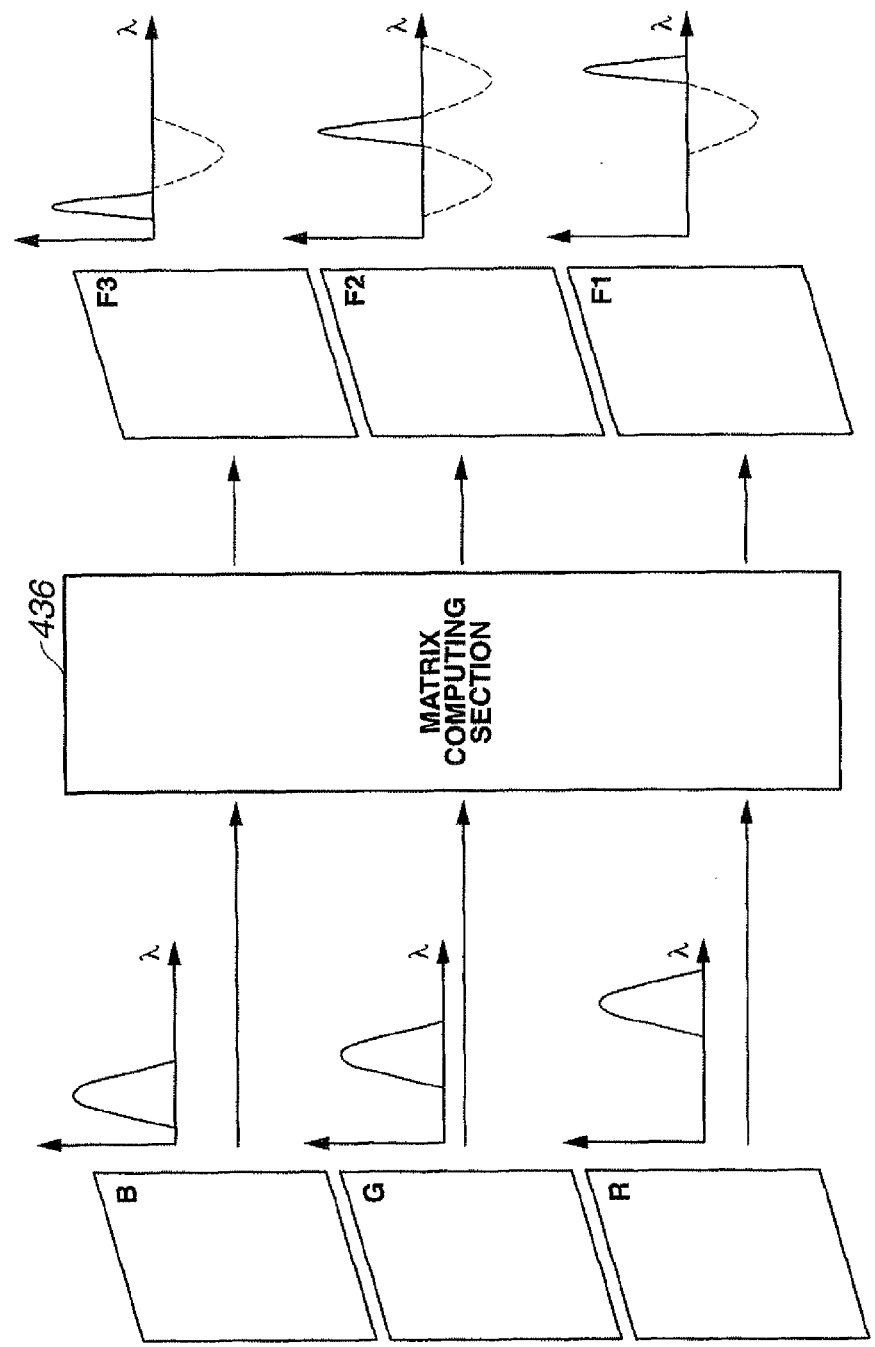
FIG. 1 is a conceptual diagram showing a flow of signals when creating a spectral image signal from a color image signal according to a first embodiment of the present invention.

FIG. 1 is a conceptual diagram showing a flow of signals when creating a spectral image signal to an image having a narrowband optical wavelength from a color image signal (in this case, while R/G/B will be used for simplicity, a combination of G/Cy/Mg/Ye may also be used with a complementary type solid state image pickup device as is the case in an embodiment to be described later).

First, the electronic endoscope apparatus converts the respective color sensitivity characteristics of R/G/B into numerical data. In this case, color sensitivity characteristics of R/G/B refer to the output characteristics of wavelengths respectively obtained when using a white light source to pickup an image of a white subject.

The respective color sensitivity characteristics of R/G/B are displayed on the right hand side of each image data as a simplified graph. In addition, the respective R/G/B color sensitivity characteristics at this point are assumed to be n-dimension column vectors <R>/<G>/<B>.

Next, the electronic endoscope apparatus converts into numerical data the characteristics of narrow bandpass filters F1/F2/F3 for spectral images to be extracted (as a priori information, the electronic endoscope apparatus is aware of characteristics of filters capable of efficiently extracting structures; as for the characteristics of the filters, it is assumed that the passbands of the respective filters are wavelength ranges of approximately 590 nm to 610 nm, approximately 530 nm to 550 nm and approximately 400 nm to 430 nm).

In this case, "approximately" is a concept that includes around ±10 nm as far as wavelengths are concerned. The respective filter characteristics at this point are assumed to be n-dimension column vectors $<F_1>/<F_2>/<F_3>$. Based on the obtained numerical data, an optimum coefficient set approximating the following relationship is determined. In other words, determining elements of a matrix satisfying $$(R\ G\ B)\begin{pmatrix} a_1 & a_2 & a_3 \\ b_1 & b_2 & b_3 \\ c_1 & c_2 & c_3 \end{pmatrix} = (F_1\ F_2\ F_3) \quad (1)$$

shall suffice.

The solution of the optimization proposition presented above is obtained as follows. If <C> denotes a matrix representing color sensitivity characteristics of R/G/B, <F> denotes spectral characteristics of a narrow bandpass filter to be extracted, and <A> denotes a coefficient matrix to be determined that executes principal component analysis or orthogonal expansion (or orthogonal transform), it follows that $$C = (R\ G\ B) \quad A = \begin{pmatrix} a_1 & a_2 & a_3 \\ b_1 & b_2 & b_3 \\ c_1 & c_2 & c_3 \end{pmatrix} \quad F = (F_1\ F_2\ F_3). \quad (2)$$

Therefore, the proposition expressed as Formula 1 is equivalent to determining a coefficient matrix <A> that satisfies the following relationship.

$$CA = F \quad (3)$$

Here, since n>3 is true for n-number of dots in a sequence as spectral data representing spectral characteristics, Formula 3 is obtained as a solution of linear least squares method instead of a linear simultaneous equation. In other words, deriving a pseudo inverse matrix from Formula 3 shall suffice. Assuming that a transposed matrix of the matrix <C> is $<^tC>$, Formula 3 may be expressed as $$^tCCA = {}^tCF \quad (4).$$

Since $<^tCC>$ is an n by n square matrix, Formula 4 may be viewed as a simultaneous equation on the coefficient matrix <A>, whereby a solution thereof may be determined from $$A = (^tCC)^{-1}{}^tCF \quad (5)$$

By transforming the left hand side of Formula 3 with respect to the coefficient matrix <A> determined by Formula 5, the electronic endoscope apparatus is able to approximate the characteristics of the narrow bandpass filters F1/F2/F3 to be extracted. This concludes the description on the matrix calculating method that forms the foundation of the present invention.

Using a matrix calculated in this manner, a matrix computing section 436, to be described later, creates a spectral image signal from a color image signal.

Through signal processing performed by the matrix computing section 436 and the like as described above, signals corresponding to narrow bandpass filters F1/F2/F3 to be calculated (from an RGB broad bandpass filter) becomes a spectral image signal. Therefore, in the embodiment hereinafter described, F1/F2/F3 will be used as a spectral image signal.

In addition, since F1/F2/F3 as a spectral image signal corresponds to narrow bandpass filters created through electrical signal processing, there are cases where a quasi-narrow bandpass filter is used to clearly specify spectral characteristic features thereof.

(Correcting Method)

Next, a correcting method for obtaining a more accurate spectral image signal will be described.

In the description of the matrix calculating method presented above, the method is accurately applied in a case where a light flux received by a solid state image pickup device such as a CCD is perfect white light (all wavelength intensities are the same in the visible range). In other words, optimum approximation is achieved when the respective outputs of R, G and B are the same.

However, in real-world endoscopic observation, since an illuminated light flux (light flux from a light source) is not perfect white light nor is the reflectance spectrum of a living body uniform, the light flux received by a solid state image pickup device is also not white light (coloration suggests that the R, G and B values are not the same).

Therefore, in actual processing, in order to more accurately solve the proposition expressed by Formula 3, it is desirable to take spectral characteristics of illumination light and reflection characteristics of a living body into consideration in addition to RGB color sensitivity characteristics.

Let us now assume that the color sensitivity characteristics are respectively R(λ), G(λ) and B(λ), an example of the spectral characteristics of illumination light is S(λ), and an example of the reflection characteristics of a living body is H(λ). Incidentally, the spectral characteristics of illumination light and the reflection characteristics of a living body need not necessarily be the characteristics of the apparatus to be used for examination or the subject to be examined, and, for example, general characteristics obtained in advance may be used instead.

Using these coefficients, correction coefficients $k_R/k_G/k_B$ may be determined by $$k_R = (\int S(\lambda) \times H(\lambda) \times R(\lambda) d\lambda)^{-1}$$

$$k_G = (\int S(\lambda) \times H(\lambda) \times G(\lambda) d\lambda)^{-1}$$

$$k_B = (\int S(\lambda) \times H(\lambda) \times B(\lambda) d\lambda)^{-1} \quad (6).$$

A sensitivity correction matrix denoted by <K> may be determined as follows.

$$K = \begin{pmatrix} k_R & 0 & 0 \\ 0 & k_G & 0 \\ 0 & 0 & k_B \end{pmatrix} \quad (7)$$

Therefore, as for the coefficient matrix <A>, the addition of the correction represented by Formula 7 to Formula 5 results in the following.

$$A^t = KA = K({}^tCC)^{-1t}CF \quad (8)$$

In addition, when performing actual optimization, taking advantage of the fact that 0 replaces negative spectral sensitivity characteristics of targeted filters (F1/F2/F3 in FIG. 1) during image display (in other words, only portions having positive sensitivity among the spectral sensitivity characteristics of filters are used), an allowance for portions of an optimized sensitivity distribution becoming negative is added. In order to create narrowband spectral sensitivity characteristics from broad spectral sensitivity characteristics, the electronic endoscope apparatus can create a component that approximates a band having sensitivity by adding negative sensitivity characteristics to the targeted characteristics of F1/F2/F3 as shown in FIG. 1.

(S/N Improving Method)

Next, a description will be given on a method for enhancing the S/N and accuracy of a created spectral image signal. Through the addition of the above-described processing method, the S/N improving method further solves the following problems.

(i) When any of original signals (R/G/B) in the above-described matrix calculating method temporarily enters a saturated state, there is a possibility that the characteristics of the filters F1 to F3 in the processing method differ significantly from characteristics (ideal characteristics) of a filter capable of efficiently extracting a structure of an observation object portion (when filters F1 to F3 are created only from two signals among R/G/B, it is required that neither of the two original signals are saturated).

(ii) Since a narrowband filter is created from a broadband filter when converting a color image signal into a spectral image signal, sensitivity degradation occurs, resulting in the creation of a smaller spectral image signal component and inferior S/N.

Figure 2:
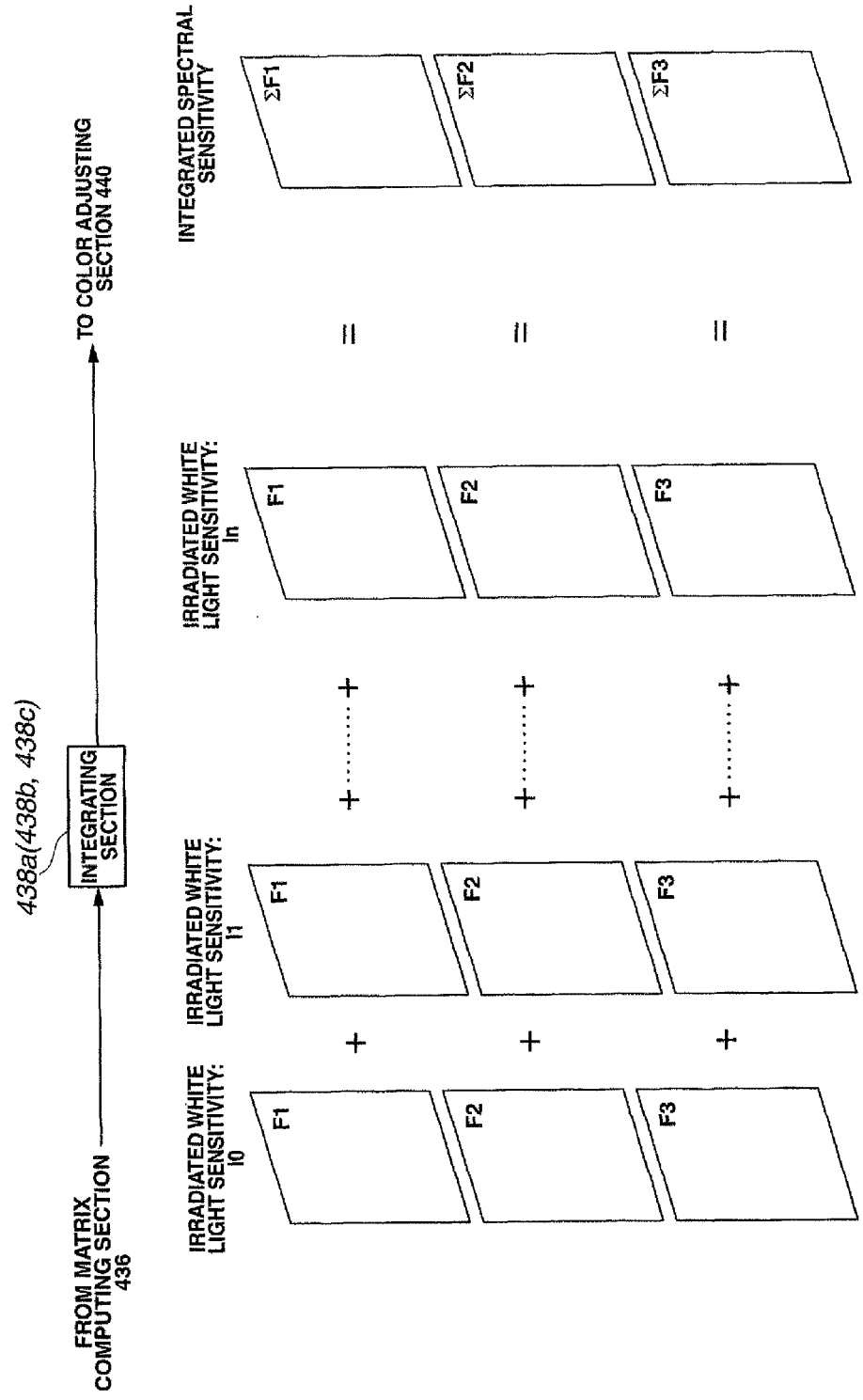
FIG. 2 is a conceptual diagram showing integrating computation of a spectral image signal according to the first embodiment of the present invention.

With the present S/N improving method, as shown in FIG. 2, illumination light is irradiated in several stages (e.g., n-stages, where n is an integer equal to or greater than 2) through 1 field (1 frame) of a normal image (an ordinary color image) (irradiation intensity may be varied for each stage; in FIG. 2, the stages are denoted by reference characters I0 to In; this procedure can be achieved wholly by controlling illumination light).

Consequently, the electronic endoscope apparatus can reduce illumination intensity for each stage, thereby suppressing occurrences of saturated states in the respective R, G and B signals. In addition, image signals separated into several stages are added n-times at a post-stage. As a result, the electronic endoscope apparatus is able to increase the signal component to enhance S/N. In FIG. 2, integrating sections 438a to 438c function as image quality adjusting sections that improve S/N.

This concludes the descriptions on the matrix calculating method that forms the foundation of the present invention, as well as the correcting method for determining an accurate and executable spectral image signal and the method for enhancing the S/N of a created spectral image signal.

A modification of the above-described matrix calculating method will now be described.

(Modification of Matrix Calculating Method)

Let us assume that color image signals are denoted as R, G, B, and spectral image signals to be estimated as F1, F2 and F3. More precisely, although color image signals R, G, B and the like are functions of a position x,y on an image and therefore, for example, R should be denoted as R(x,y), such notations shall be omitted herein.

An objective is to estimate a 3 by 3 matrix <A> that calculates F1, F2 and F3 from R, G, and B. Once <A> is estimated, it is now possible to calculate F1, F2 and F3 ($F_1$, $F_2$ and $F_3$ in matrix notation) from R, G, B using Formula 9 below.

$$\begin{pmatrix} F_1 \\ F_2 \\ F_3 \end{pmatrix} = A \begin{pmatrix} R \\ G \\ B \end{pmatrix} \quad (9)$$

Notation of the following data will now be defined.
Spectral characteristics of a subject to be examined: $H(\lambda)$, <H>=$(H(\lambda 1), H(\lambda 2), \ldots H(\lambda n))^t$,
where $\lambda$ denotes wavelength and t denotes transposition in matrix computation. In a similar manner,
spectral characteristics of illumination light: $S(\lambda)$, <S>=$(S(\lambda 1), S(\lambda 2), \ldots S(\lambda n))^t$,
spectral sensitivity characteristics of a CCD: $J(\lambda)$, <J>=$(J(\lambda 1), J(\lambda 2), \ldots J(\lambda n))^t$,
spectral characteristics of filters performing color separation: in the case of primary colors $R(\lambda),<R>=(R(\lambda 1),R(\lambda 2),\ldots R(\lambda n))^t$, $G(\lambda),<G>=(G(\lambda 1),G(\lambda 2),\ldots G(\lambda n))^t$, and $B(\lambda),<B>=(B(\lambda 1),B(\lambda 2),\ldots B(\lambda n))^t$.

As indicated by Formula 10, <R>, <G> and <B> can be bundled together into a matrix <C>.

$$C = \begin{pmatrix} R \\ G \\ B \end{pmatrix} \quad (10)$$

Image signals R, G, B and spectral signals F1, F2 and F3 may be expressed by matrix as follows.

$$P = \begin{pmatrix} R \\ G \\ B \end{pmatrix}, \quad Q = \begin{pmatrix} F_1 \\ F_2 \\ F_3 \end{pmatrix} \quad (11)$$

An image signal <P> may be calculated using the following formula.

$$P = CSJH \quad (12)$$

Assuming now that a color separation filter for obtaining <Q> is denoted as <F>, in the same manner as Formula 12, $$Q = FSJH \quad (13).$$

At this point, as a first important hypothesis, if it is assumed that the spectral reflectance of the subject to be examined may be expressed as a linear sum of three elementary spectral characteristics, <H> in Formulas 12 and 13 may be expressed as $$H \approx DW \quad (14),$$

where <D> denotes a matrix having three elementary spectrums $D1(\lambda)$, $D2(\lambda)$, $D3(\lambda)$ as column vectors and <W> denotes a weighting coefficient representing the contribution of $D1(\lambda)$, $D2(\lambda)$, $D3(\lambda)$ towards <H>. It is known that the above approximation is true when the color tone of the subject to be examined does not vary significantly.

Assigning Formula 14 into Formula 12 we obtain $$P = CSJH = CSJDW = MW \quad (15),$$

where the 3 by 3 matrix <M> represents a matrix in which the calculation results of matrices <CSJD> are bundled together.

In the same manner, assigning Formula 14 into Formula 13 we obtain $$Q = FSJH = FSJDW = M'W \quad (16),$$

where, similarly, the 3 by 3 matrix <M'> represents a matrix in which the calculation results of matrices <FSJD> are bundled together.

Ultimately, eliminating <W> from Formulas 15 and 16 we obtain $$Q = M'M^{-1}P \quad (17),$$

where <$M^{-1}$> represents an inverse matrix of matrix <M>. Ultimately, <M', $M^{-1}$> turns out to be a 3 by 3 matrix which becomes the estimation target matrix <A>.

At this point, as a second important hypothesis, when performing color separation using a bandpass filter, let us assume that the spectral characteristics of the subject to be examined within the band may be approximated using a single numerical value. In other words, $$H = (h_1, h_2, h_3)^t \quad (18).$$

If the hypothesis is true when also taking into consideration a case where the bandpass for color separation is not a perfect bandpass and may have sensitivity in other bands, a matrix similar to that of Formula 17 can be ultimately estimated by considering the <W> in Formulas 15 and 16 as the above-described <H>.

Next, a specific configuration of an electronic endoscope apparatus in the first embodiment of the biological observation apparatus according to the present invention will be described with reference to FIG. 3. Incidentally, the other embodiments described later may be similarly configured.

Figure 3:
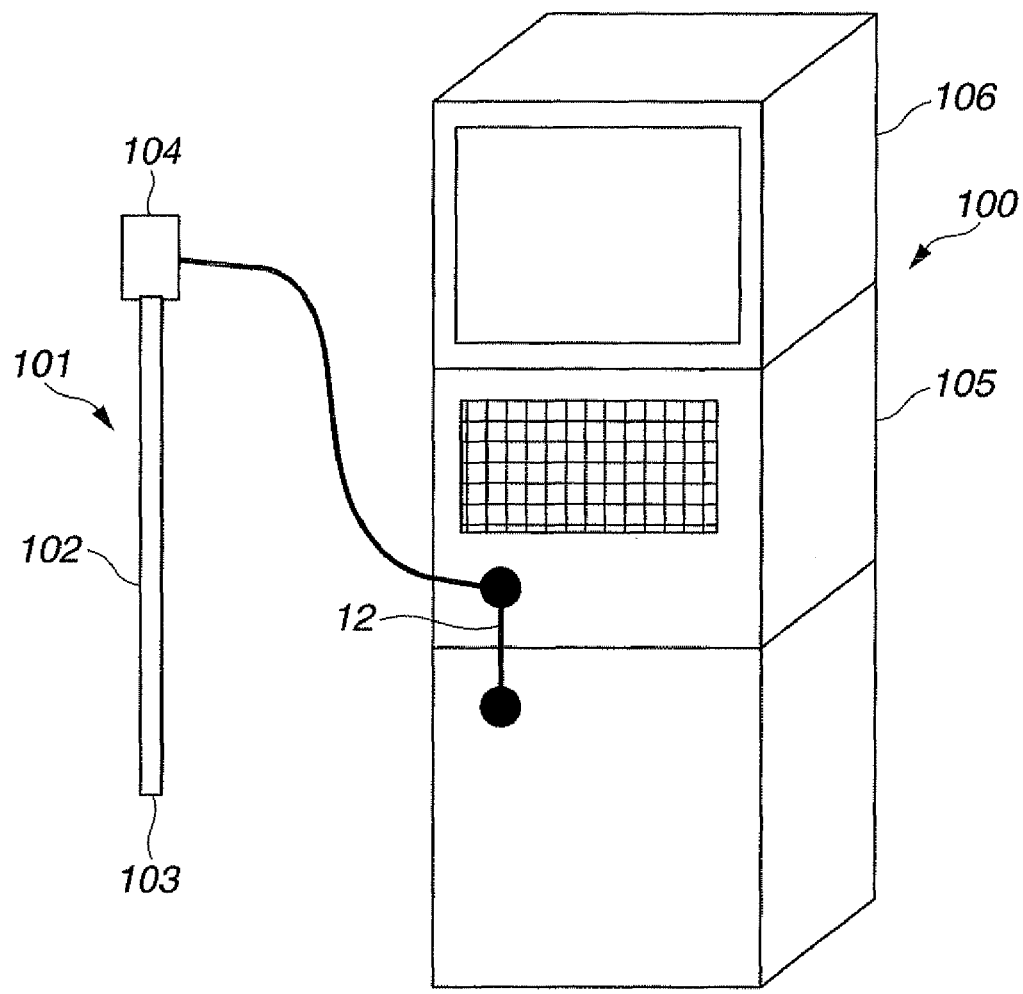
FIG. 3 is a conceptual diagram showing an external appearance of an electronic endoscope apparatus according to the first embodiment of the present invention.

As shown in FIG. 3, an electronic endoscope apparatus 100 comprises an electronic endoscope (abbreviated to endoscope) 101, an endoscope apparatus main body 105, and a display monitor 106 as a display device. In addition, the endoscope 101 is primarily constituted by: an insertion portion 102 to be inserted into the body of a subject to be examined; a distal end portion 103 provided at an distal end of the insertion portion 102; and an angle operating section 104 provided on an opposite side of the distal end side of the insertion portion 102 and which is provided for performing or instructing operations such as bending operations of the distal end portion 103 side.

An image of the interior of the subject to be examined or the like acquired by the endoscope 101 is subjected to predetermined signal processing at the endoscope apparatus main body 105, and a processed image is displayed on the display monitor 106.

Figure 4:
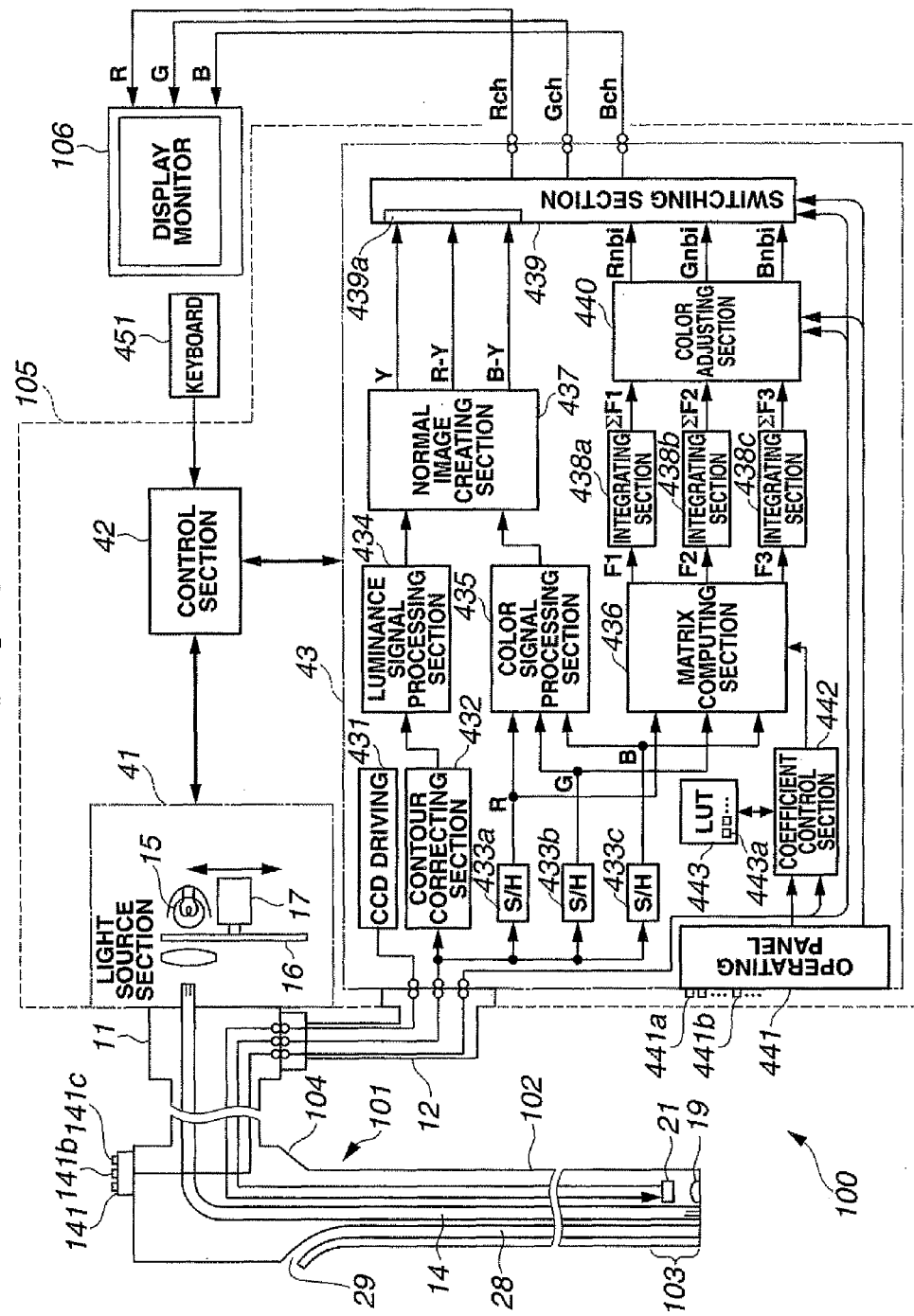
FIG. 4 is a block diagram showing a configuration of the electronic endoscope apparatus shown in FIG. 3.

Next, the endoscope apparatus main body 105 will be described in detail with reference to FIG. 4. FIG. 4 is a block diagram of the electronic endoscope apparatus 100.

As shown in FIG. 4, the endoscope apparatus main body 105 comprises: a light source section 41 that primarily acts as an illuminating section that generates illumination light; a control section 42 that controls the light source section 41 and a main body processing apparatus 43 described below; and the main body processing apparatus 43 that performs signal processing for creating a normal image and signal processing for creating a spectral image. The control section 42 and the main body processing apparatus 43 control operations of the light source section 41 and/or a CCD 21 as an image pickup section, and constitute a signal processing control section that outputs an image pickup signal to the display monitor 106 that is a display device.

Incidentally, for the present embodiment, while a description will be given on the assumption that the light source section 41 and the main body processing apparatus 43 that performs image processing and the like are provided within the endoscope apparatus main body 105 that is a single unit, these sections may be alternatively configured as connectable and detachable separate units. In addition, while the biological observation apparatus can be configured by the endoscope 101, the light source section 41 and the main body processing apparatus 43, the present invention is not limited to this configuration. For example, the biological observation apparatus can be either configured by the light source section 41 and the main body processing apparatus 43, or by the main body processing apparatus 43 alone.

The light source section 41 is connected to the control section 42 and the endoscope 101. The light source section 41 irradiates a white light (including light that is not perfectly white) at a predetermined light quantity based on a signal from the control section 42. In addition, the light source section 41 comprises: a lamp 15 as a white light source; a chopper 16 for adjusting light quantity; and a chopper driving section 17 for driving the chopper 16.

Figures 5, 6:
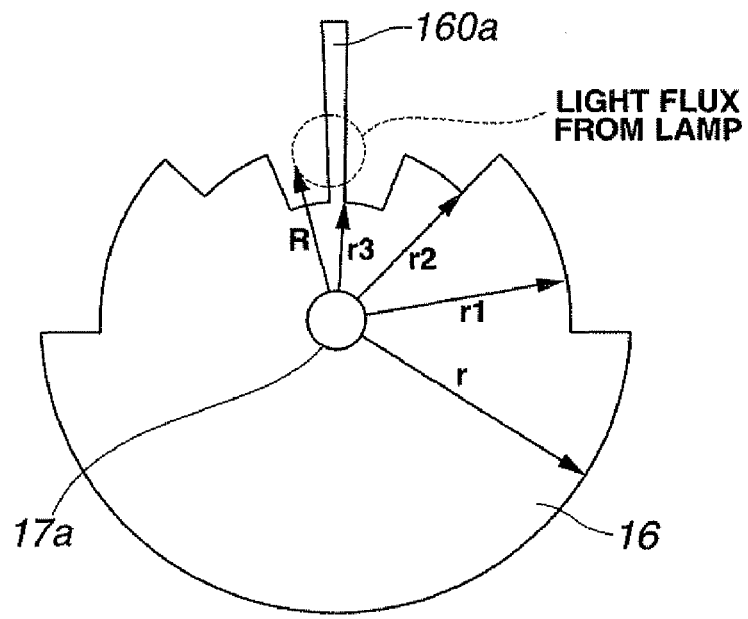
FIG. 5 is an exterior view of a chopper shown in FIG. 4.
FIG. 6 is a diagram showing an array of color filters positioned on an image pickup plane of a CCD shown in FIG. 4.

As shown in FIG. 5, the chopper 16 is configured as a disk-like structure having a predetermined radius r around a central point 17a and having notched portions of predetermined circumferential lengths. The central point 17a is connected to a rotary shaft provided at the chopper driving section 17. In other words, the chopper 16 performs rotational movement around the central point 17a. In addition, a plurality of notched portions are provided in intervals of a predetermined radius. In the diagram, from radius r0 to radius ra, the notched portion has a maximum length of $2\pi r \times \theta 0$ degrees/360 degrees and a width of r0–ra. In a similar manner, the notched portion is configured so as to have, from radius ra to radius rb, a maximum length of $2\pi ra \times 2\theta 1$ degrees/360 degrees and a width of ra–rb, and from radius rb to radius rc, a maximum length of $2\pi rb \times 2\theta 2$ degrees/360 degrees and a width of rb–rc (where the respective radii have a relationship of r0>ra>rb>rc).

The lengths and widths of the notched portions of the chopper 16 are merely exemplary and are not limited to the present embodiment.

In addition, the chopper 16 has a protruding portion 160a that radially extends at an approximate center of the notched portion. The control section 42 is arranged so as to minimize intervals of light irradiated before and after 1 frame to minimize blurring due to the movement of the subject to be examined by switching frames when light is cut off by the protruding portion 160a.

Furthermore, the chopper driving section 17 is configured so as to be movable in a direction facing the lamp 15 as is indicated by the arrow in FIG. 4.

In other words, the control section 42 is able to change a direction R between the rotational center 17a of the chopper 16 shown in FIG. 5 and a light flux (indicated by the dotted circle) from the lamp. For example, in the state shown in FIG. 5, since the distance R is considerably small, illumination light quantity is low. By increasing the distance R (moving the chopper driving section 17 away from the lamp 15), the notched portion through which the light flux is passable becomes longer, thereby extending irradiating time and enabling the control section 42 to increase illumination light quantity.

As described above, with the electronic endoscope apparatus, since there is a possibility that the S/N of a newly created spectral image is insufficient and a saturation of any of the necessary RGB signals upon creation of a spectral image results in improper computation, it is necessary to control illumination light quantity. The chopper 16 and the chopper driving section 17 are responsible for light quantity adjustment.

In addition, the endoscope 101 detachably connected to the light source section 41 via a connector 11 is provided: with an objective lens 19 that forms an optical image on the distal end portion 103; and a solid state image pickup device 21 such as a CCD that performs photoelectric conversion (hereinafter simply referred to as CCD) arranged at an image forming position thereof. The CCD used in the present embodiment is a single-plate CCD (the CCD used in a synchronous electronic endoscope), and has a primary color-type color transmitting filter (abbreviated to color filter). FIG. 6 shows an array of color filters positioned on an image pickup plane of a CCD. In addition, FIG. 7 shows respective spectral sensitivity characteristics of RGB of the color filters shown in FIG. 6.

Figure 7:
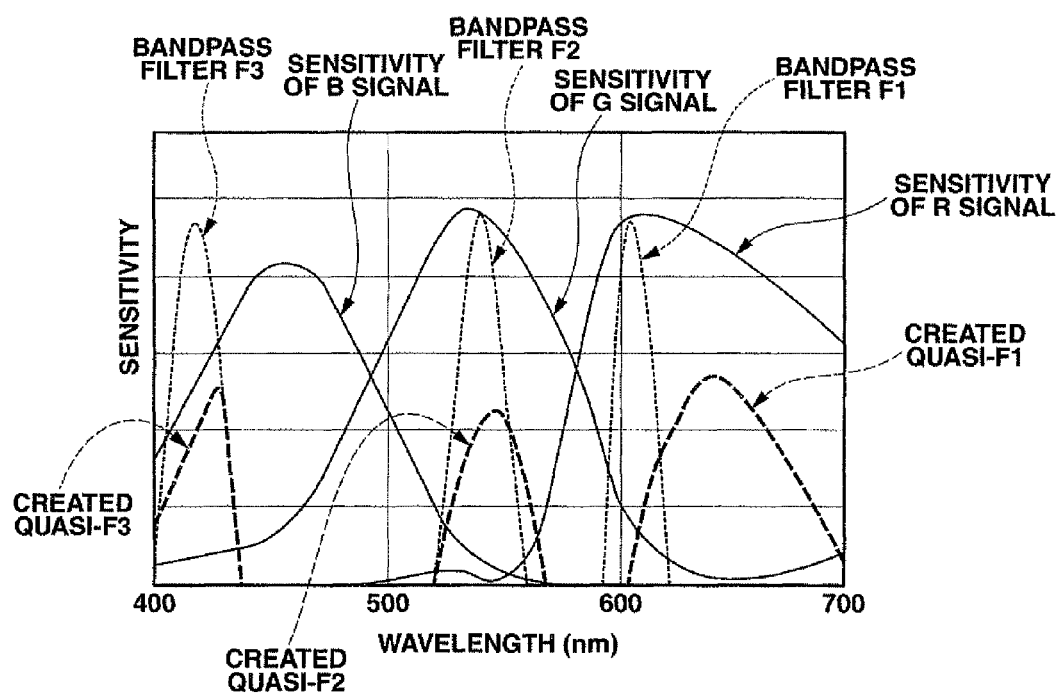
FIG. 7 is a diagram showing spectral sensitivity characteristics of the color filters shown in FIG. 6.

As shown in FIG. 7, the RGB color filters have spectral characteristics that respectively transmit R, G and B wavelength regions of the visible range in a broadband.

In addition, as shown in FIG. 4, the insertion portion 102 comprises: a light guide 104 that guides light irradiated from the light source section 41 to the distal end portion 103; a signal line for transferring an image of the subject to be examined obtained by the CCD to the main body processing apparatus 43; and a forceps channel 28 or the like for performing treatment. Incidentally, a forceps aperture 29 for inserting forceps into the forceps channel 28 is provided in the vicinity of an operating section 104.

Furthermore, in the same manner as the light source section 41, the main body processing apparatus 43 is connected to the endoscope 101 via the connector 11. The main body processing apparatus 43 is provided with a CCD driving circuit 431 for driving the CCD 21.

In addition, the main body processing apparatus 43 comprises as signal processing systems: a luminance signal processing system that creates a luminance signal; and a color signal processing system that creates a broadband color signal.

The luminance signal processing system comprises: a contour correcting section 432 connected to the CCD 21 and which performs contour correction; and a luminance signal processing section 434 that creates a luminance signal from data corrected by the contour correcting section 432.

In addition, the color signal processing system comprises: sample-and-hold circuits (S/H circuits) 433a to 433c, connected to the CCD 21, which perform sampling and the like on a signal obtained by the CCD 21 and create an RGB signal as a broadband color signal (or a color image signal); and a color signal processing section 435 connected to output terminals of the S/H circuits 433a to 433c and which performs processing on a color signal.

Furthermore, the main body processing apparatus 43 is provided with a normal image creating section 437 that creates a single color normal image as a color image picked up in the visible range from outputs of the luminance signal processing system and the color signal processing system. Then, a Y signal, an R-Y signal and a B-Y signal are sent as normal color image signal from the normal image creating section 437 to the display monitor 106 via the switching section 439.

On the other hand, a matrix computing section 436 that creates spectral image signals F1, F2 and F3 from outputs signals of the S/H circuits 433a to 433c that create the above-mentioned RGB signals is provided as a signal circuit system as spectral image creating means that obtains spectral images. The matrix computing section 436 performs predetermined matrix computation on RGB signals.

Matrix computation refers to addition processing of color image signals using a computation coefficient corresponding to a coefficient matrix and to processing of multiplying the matrix obtained by the above-described matrix calculating method (or modification thereof). The matrix computing section 436 creates narrowband spectral image signals F1, F2 and F3 from R, G and B color image signals.

In the present embodiment, while a method using electronic circuit processing (processing by hardware using an electronic circuit) will be described as the matrix calculating method, a method using numerical data processing (processing by software using a program) such as in an embodiment described later may be used instead. In addition, upon execution, a combination thereof may also be used.

Figure 8:
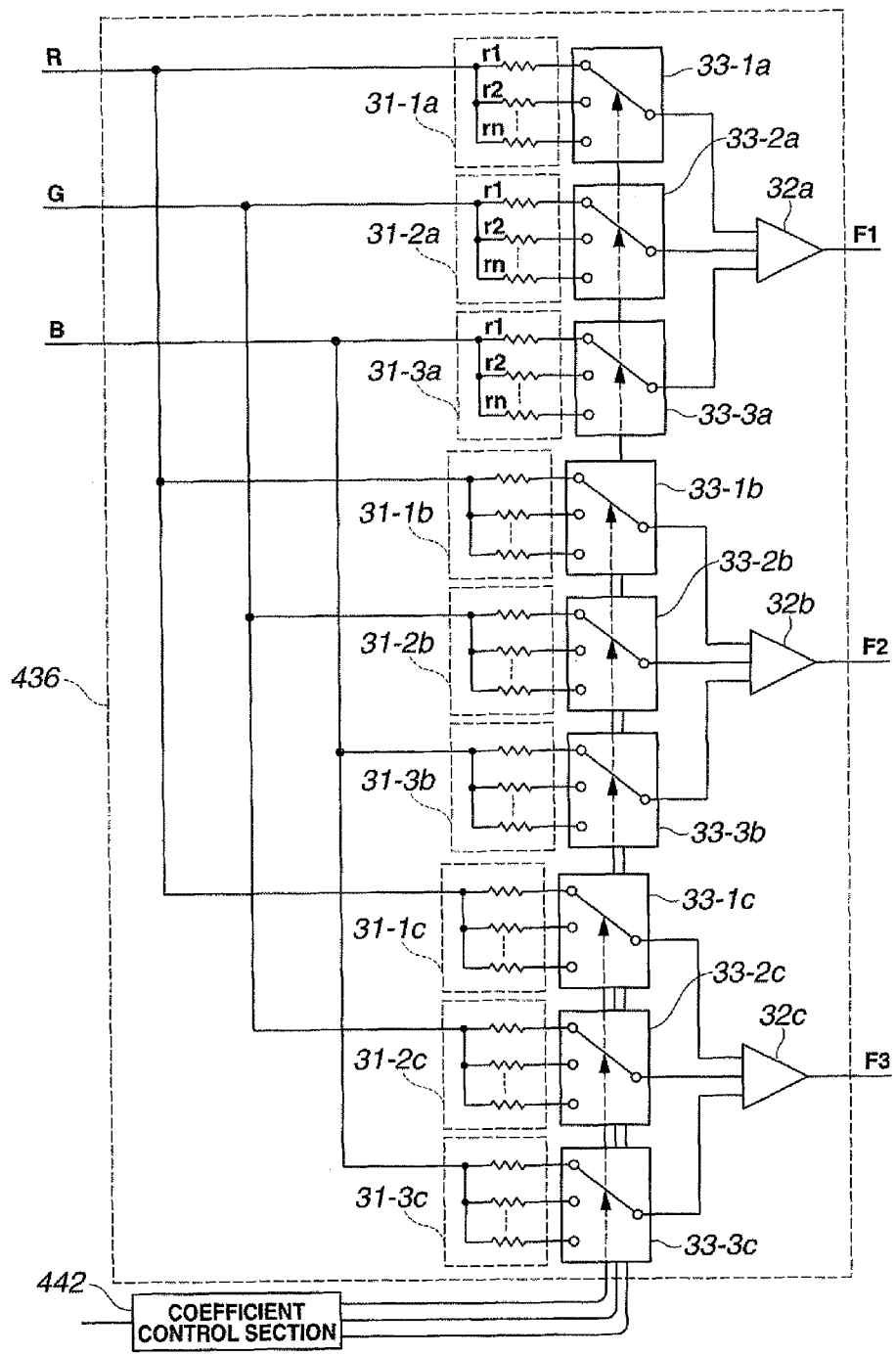
FIG. 8 is a configuration diagram showing a configuration of a matrix computing section shown in FIG. 4.

FIG. 8 is a circuit diagram of the matrix computing section 436. RGB signals are respectively inputted to amplifiers 32a to 32c via resistor groups 31-1a to 31-1c, 31-2a to 31-2c and 31-3a to 31-3c and multiplexers 33-1a to 33-1c, 33-2a to 33-2c and 33-3a to 33-3c.

The resistor groups 31-1a, 31-2a, . . . , 31-3c are respectively constituted by resistors r1, r2, . . . , rn having mutually different resistance values (in FIG. 8, only a portion thereof are denoted by characters r1, r2, . . . , rn). One resistor is respectively selected by the multiplexers 33-1a, 33-2a, . . . , 33-3c.

The multiplexers 33-1a, 33-2a, . . . , 33-3c are subjected to, for example, a switching operation or a selecting operation by a user at an operating panel 441 (refer to FIG. 4) constituting coefficient setting/switching means provided on a front panel or the like to determine a selected resistor among the resistors r1, r2, . . . , rn via a coefficient control section 442. The operating panel 441 operated by the user also functions as interface means by which the user performs switching (selection), status confirmation and the like of observation modes of the main body processing apparatus 43 that performs signal processing.

Incidentally, selection of observation modes (observation image modes) includes a function for selecting an image displayed on the display monitor 106 as well as a function of a signal processing system of the main body processing apparatus 43 so that at least a video signal (image signal) corresponding to the image is created through signal processing.

In other words, in a case where a color normal image (also simply referred to as normal image) observation mode is selected as an observation mode, switching of the switching section 439 is performed so that a normal image is displayed on the display monitor 106 and, at the same time, a normal image processing system changes to an active state so that a normal image signal corresponding to the normal image is created. In this case, the contour correcting section 432, the luminance signal processing section 434, the color signal processing section 435 and the normal image creating section 437 shown in FIG. 4 correspond to the normal image processing system.

In addition, in a case where a spectral image observation mode is selected as an observation mode, switching of the switching section 439 is performed so that a spectral image is displayed on the display monitor 106 and, at the same time, a spectral image processing system changes to an active state so that a spectral image signal corresponding to the spectral image is created. In this case, the coefficient control section 442, an LUT 443, the matrix computing section 436, the integrating sections 438a to 438c, and a color adjusting section 440 shown in FIG. 4 correspond to the spectral image processing system.

Operating states common to both observation modes are maintained for the CCD driving circuit 431 and the S/H circuits 433a to 433c. The control section 42 may be arranged to perform control so that, in accordance with the above-described selection of an observation mode, a signal processing system corresponding to the selected observation mode changes to an active state. Alternatively, both signal processing systems may be constantly maintained at active states.

In this case, an operation of observation mode selection attains the same result as a selection of an image (observation image) to be displayed on the monitor 106. However, as described later, there are cases where parameter values (or target values) when performing light quantity control of the illumination light quantity to a target value are preferably changed in conjunction with a selection (switching) of observation modes.

In addition, the user may also perform a selection operation via an endoscope switch 141 provided at the operating section of the endoscope 101. The endoscope switch 141 also forms coefficient setting/switching means that performs coefficient switching and interface means by which the user performs switching (selection) of observation modes.

The operating panel 441 or the like is provided with a plurality of selection switches (or switching buttons) 441a corresponding to, for example, type of subject to be examined, observed region, tissue type of biological tissue (morphological type of tissue) or the like. Upon operation of the selection switch 441a by the user, the selection switch 441a outputs an instruction signal corresponding to the type of subject to be examined, the observed region, the tissue type of biological tissue or the like to the coefficient control section 442.

As shown in FIG. 4, an LUT 443 as computation coefficient storing means storing computation coefficients (hereinafter simply referred to as coefficients) that determine matrix computing characteristics or matrix computing results of the matrix computing section 436 is connected to the coefficient control section 442. In accordance with an instruction signal from a selection switch 441a of the operating panel 441 or the like, the coefficient control section 442 reads out a coefficient corresponding to the type of subject to be examined or the like from the LUT 443, and sends the coefficient to the matrix computing section 436.

In other words, a plurality of coefficients 443a corresponding to the types of spectral characteristics (spectral reflectance characteristics) of subjects to be examined or, more specifically, to the types of spectral reflectance characteristics of mucosal tissue of a living body as subjects to be examined are stored in the LUT 443. Simply put, the coefficient 443a is a living body coefficient corresponding to the type of mucosal tissue of a living body or the like.

Subsequently, the matrix computing section 436 performs matrix computation using the coefficient 443a read and sent from the LUT 443. In this manner, computation for creating a spectral image signal (a quasi-optical spectral image signal through signal processing) is made possible even when types of subjects to be examined, tissue types of biological tissue or the like differ by actually using an optical narrow bandpass filter to suppress degradation in accuracy in comparison to a picked up (acquired) optical narrowband image signal or a spectral image signal.

As described above, in the present embodiment, the matrix computing section 436 is connected via the coefficient control section 442 to the LUT 443 that stores a plurality of coefficients 443a. By operating the operating panel 441 or the like, the user is able to change and set (switch and set) coefficients actually used in matrix computation by the matrix computing section 436 via the coefficient control section 442 and to change and set characteristics of the spectral image signals F1, F2 and F3 to be created. In other words, the coefficient control section 442 and the LUT 443 are provided with functions as characteristic changing/setting means that changes/sets a characteristic of a spectral image signal created by spectral image signal creating means.

An output of the matrix computing section 436 are respectively inputted to the integrating sections 438a to 438c to be subjected to respective integral computation by the integrating sections 438a to 438c. As a result, spectral image signals $\Sigma F1$ to $\Sigma F3$ are created. The spectral image signals $\Sigma 1$ to $\Sigma F3$ are inputted to the color adjusting section 440, whereby the color adjusting section 440 performs computation for color adjustment through a configuration to be described later. The color adjusting section 440 respectively creates spectral channel image signals Rnbi, Gnbi and Bnbi as color tone-adjusted spectral image signals from the spectral image signals $\Sigma F1$ to $\Sigma F3$.

Subsequently, a color image signal (also referred to as a living body signal) from the normal image creating section 437 or spectral channel image signals Rnbi, Gnbi and Bnbi from the color adjusting section 440 are respectively outputted via the switching section 439 to an R channel, a G channel and a B channel (sometimes abbreviated to Rch, Gch and Bch) of the display monitor 106 and displayed in the display colors of R, G and B on the display monitor 106. Therefore, the color adjusting section 440 is provided with a function of display color converting means that converts the display colors used when quasi-color displaying the spectral image signals $\Sigma F1$ to $\Sigma F3$ on the display monitor 106. In addition, by performing changing/setting such as the switching of coefficients used when performing display color conversion by the display color converting means, a function of display color adjusting means or color adjusting means that adjusts display colors is provided. A supplementary description on the color adjusting section 440 may be given as below.

As described above, (display) color adjustment processing including display color conversion performed on the spectral image signals $\Sigma F1$ to $\Sigma F3$ by the color adjusting section 440 results in spectral channel image signals Rnbi, Gnbi and Bnbi, which are then respectively outputted to the R channel, G channel and the B channel of the display monitor 106. Respectively outputting (allocating display color) the spectral image signals $\Sigma F1$ to $\Sigma F3$ to the R channel, G channel and the B channel of the display monitor 106 without performing (display) color conversion results in fixed color tones which cannot be selected or changed by the user.

In the present embodiment, by providing color adjusting means including color conversion as described above, quasi-color display is made available in color tones that are desirable to the user. In addition, quasi-color display can be performed under better visibility by performing color conversion or color adjustment. Incidentally, as is apparent from the above description, the spectral channel image signals Rnbi, Gnbi and Bnbi are used to clearly demonstrate that output is respectively performed to the R channel, G channel and the B channel of the display monitor 106. Accordingly, these signals shall be collectively referred to as a spectral image signal. By changing focus to quasi-colored display performed on the monitor side as in a seventh embodiment to be described later, the spectral channel image signals Rnbi, Gnbi and Bnbi can also be referred to as color channel image signals. The configuration of the color adjusting section 440 shall be described later.

The color adjusting section 440 is connected to the operating panel 441 provided with a function as display color changing/setting means or interface means, the endoscope switch 141, and the like. The color adjusting section 440 is arranged so that the user or the like can perform operations for display color changing/setting for color adjustment (more specifically, coefficient switching/setting operations) via the operating panel 441, the endoscope switch 141, and the like. As will be described later, according to a signal from the operating panel 441 or the like, the coefficient of a 3 by 3 matrix circuit 61 that performs display color conversion can be switched via a coefficient changing circuit 64 constituting the color adjusting section 440.

Incidentally, the switching section 439 is provided for switching between a normal image and a spectral image, but is also capable of switching/displaying among spectral images. In other words, upon selection operation by the user such as an operator of a signal to be outputted to the display monitor 106 among a normal image signal and spectral channel image signals Rnbi, Gnbi and Bnbi, the switching section 439 selects (switches) the selection-operated signal and outputs the same to the display monitor 106.

The switching section 439 is connected to the operating panel 441 and the endoscope switch 141 which are operated by the user to easily perform switching or selection of normal images and spectral images. Therefore, according to the present embodiment, operability can be enhanced. Incidentally, as shown in FIG. 4, an instruction inputted to a keyboard 451 is arranged to be inputted to the control section 42. When an inputted instruction is a switching instruction, the control section 42 performs switching control and the like of the switching section 439 in correspondence with the switching instruction.

Furthermore, a configuration in which any two or more images are simultaneously displayable on the display monitor 106 is also possible. A relevant configuration shall be described later with reference to FIG. 46 and the like.

In particular, in a case where a normal image and a spectral channel image (also referred to as a spectral image) are simultaneously displayable, a generally observed normal image and a spectral image can be easily compared, and observation can be performed while taking into consideration the respective features thereof (a feature of normal images is that the color tones thereof closely resemble that of naked eye observation for easy observation; a feature of spectral images is that observation of predetermined blood vessels or the like which cannot be observed through normal images are possible), making it extremely useful in diagnostics.

Next, a detailed description on operations of the electronic endoscope apparatus 100 according to the present embodiment will be given with reference to FIG. 4.

In the following, operations during normal image observation will be described first, followed by a description on operations during spectral image observation.

First, an operation of the light source section 41 will be described. Based on a control signal from the control section 42, the chopper driving section 17 is set to a predetermined position and rotates the chopper 16. A light flux from the lamp 15 passes through a notched portion of the chopper 16, and is collected by a collecting lens at an incident end of the light guide 14 that is a light fiber bundle provided inside the connector 11 located at a connecting portion of the endoscope 101 and the light source section 41.

The collected light flux passes the light guide 14 and is irradiated into the body of a subject to be examined from an illuminating optical system, not shown, provided at the distal end portion 103. The irradiated light flux is reflected inside the subject to be examined, and signals are collected via the objective lens 19 by the CCD 21 provided with color filters according to each color filter shown in FIG. 6. Signals (image pickup signals) collected according to color filter by the CCD 21 are inputted in parallel to the luminance signal processing system and the color signal processing system described above.

Signals collected according to color filter are added on a per-pixel basis and inputted to the contour correcting section 432 of the luminance signal system, and after contour correction, inputted to the luminance signal processing section 434. A luminance signal is created at the luminance signal processing section 434, which is then inputted to the normal image creating section 437.

Meanwhile, signals collected according to color filter by the CCD 21 is inputted on a per-filter basis to the S/H circuits 433a to 433c, and R/G/B signals are respectively created as a plurality of broadband color signals. In addition, after the R/G/B signals are subjected to signal processing for color signals at the color signal processing section 435, a Y signal, an R-Y signal and a B-Y signal are created at the normal image creating section 437 as color image signals from the afore-mentioned luminance signals and color signals, and a normal image of the subject to be examined is color-displayed on the display monitor 106 via the switching section 439.

Incidentally, as shown in FIG. 4, the output signal from the normal image creating section 437 and the output signal from the color adjusting section 440 may be arranged to be inputted to the R channel, G channel and the B channel of the display monitor 106 by sharing the output end of the switching section 439. In the case of a configuration in which the output end is shared, incorporating a converting circuit 439a (refer to FIG. 4) that converts the Y signal, the R-Y signal and the B-Y signal that are output signals from the normal image creating section 437 into R, G and B signals into the switching section 439 shall suffice.

In an alternative configuration, instead of incorporating the converting circuit 439a, the output signal from the normal image creating section 437 is inputted to a Y/color difference signal input end of the display monitor 106 while the output signal from the color adjusting section 440 is respectively inputted to the R channel, G channel and the B channel of the display monitor 106. Below, for simplicity, a case will be described in which even an output signal from the normal image creating section 437 is inputted to the display monitor 106 via a common R channel, a common G channel and a common B channel when outputted from the switching section 439.

Next, operations during spectral image observation will be described. Incidentally, descriptions on operations similar to those performed during normal image observation shall be omitted.

An operator issues an instruction for observing a spectral image from a normal image by operating the endoscope switch 141, the keyboard 451 or the like connected to the endoscope apparatus main body 105. At this point, the control section 42 changes the control state of the light source section 41 and the main body processing apparatus 43.

More specifically, as required, the control section 42 changes the light quantity irradiated from the light source section 41. As described above, since saturation of an output signal from the CCD 21 is undesirable, illumination light quantity is reduced in comparison to normal image observation. Furthermore, in addition to controlling the light quantity so that an output signal from the CCD 21 does not reach saturation, the control section 42 is also able to change illumination light quantity within a range in which saturation is not reached.

In addition, as an example of changing control contents over the main body processing apparatus 43 by the control section 42, a signal outputted from the switching section 439 is switched from an output of the normal image creating section 437 to an output of the color adjusting section 440, in other words, the spectral channel image signals Rnbi, Gnbi and Bnbi.

In addition, the outputs of the S/H circuits 433a to 433c are inputted to the matrix computing section 436, and subjected to amplification/addition processing at the matrix computing section 436 to create narrowband spectral image signals F1, F2 and F3. The spectral image signals F1, F2 and F3 are outputted to the integrating sections 438a to 438c according to each band.

Even when illumination light quantity is reduced by the chopper 16, storage and integration by the integrating sections 438a to 438c enable signal intensity to be increased as shown in FIG. 2. In addition, through the integrating sections 438a to 438c, integrated spectral image signals ΣF1, ΣF2 and ΣF3 with improved S/N over spectral image signals F1, F2 and F3 respectively can be obtained.

A specific description will now be given on matrix processing performed by the matrix computing section 436 according to the present embodiment. In the present embodiment, when attempting to create bandpass filters (hereinafter referred to as a quasi-bandpass filters) closely resembling ideal narrowband pass filters F1 to F3 (in this case, the respective wavelength transmitting ranges are assumed to be F1: 590 nm to 620 nm, F2: 520 nm to 560 mm, and F3: 400 nm to 440 nm) depicted in FIG. 7 from the spectral sensitivity characteristics of the RGB color filters indicated by the solid lines in FIG. 7, according to the contents represented by Formulas 1 to 5 presented above, the following matrix becomes optimum.

$$A = \begin{pmatrix} 0.625 & -3.907 & -0.05 \\ -3.097 & 0.631 & -1.661 \\ 0.036 & -5.146 & 0.528 \end{pmatrix} \quad (19)$$

Furthermore, by performing correction using contents represented by Formulas 6 and 7, the following coefficient is obtained.

$$K = \begin{pmatrix} 1 & 0 & 0 \\ 0 & 1.07 & 0 \\ 0 & 0 & 1.57 \end{pmatrix} \quad (20)$$

Figure 9:
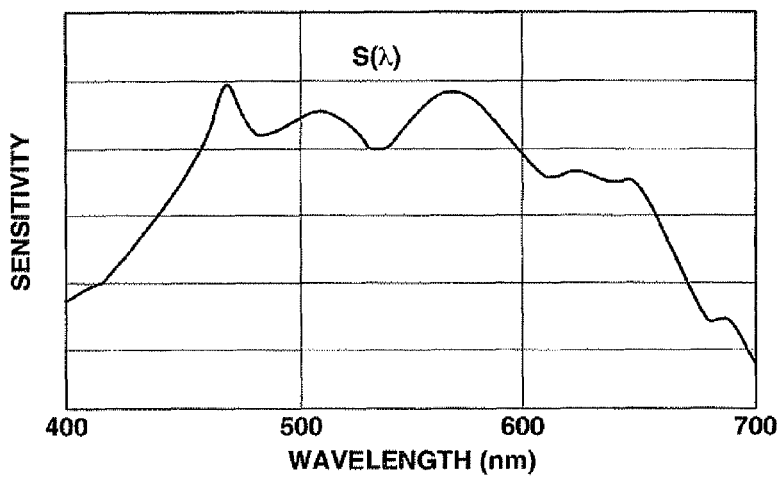
FIG. 9 is a spectrum diagram showing a spectrum of a light source according to the first embodiment of the present invention.
Figure 10:
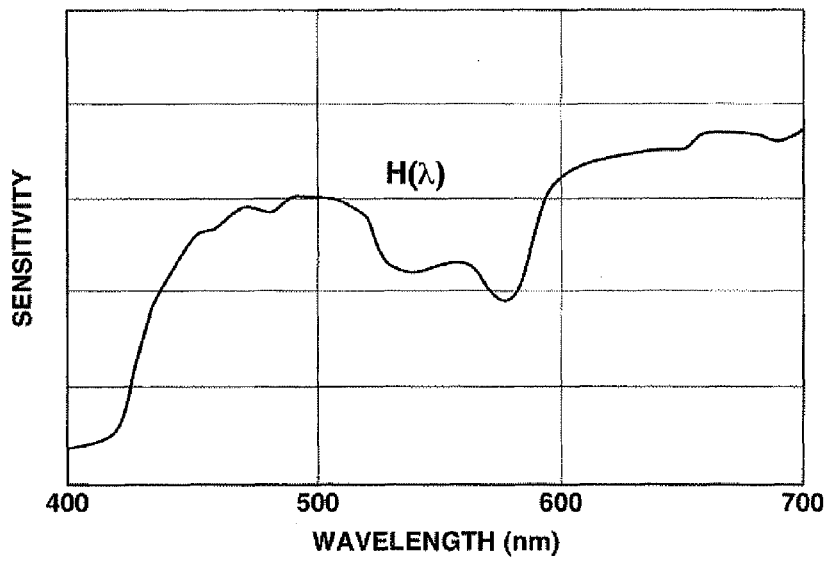
FIG. 10 is a spectrum diagram showing a reflectance spectrum of a living body according to the first embodiment of the present invention.

Incidentally, the above uses a priori information that the spectrum S(λ) of a light source represented by Formula 6 is depicted in FIG. 9 and the reflectance spectrum H(λ) of the living body to be studied represented by Formula 7 is depicted in FIG. 10.

Therefore, the processing performed by the matrix computing section 436 is mathematically equivalent to the matrix computation below.

$$A' = KA \quad (21)$$

$$= \begin{pmatrix} 1 & 0 & 0 \\ 0 & 1.07 & 0 \\ 0 & 0 & 1.57 \end{pmatrix} \begin{pmatrix} 0.625 & -3.907 & -0.05 \\ -3.097 & 0.631 & -1.661 \\ 0.036 & -5.146 & 0.528 \end{pmatrix}$$

$$= \begin{pmatrix} 0.625 & -3.907 & -0.050 \\ -3.314 & 0.675 & -1.777 \\ 0.057 & -8.079 & 0.829 \end{pmatrix}$$

By performing the matrix computation, quasi-filter characteristics (indicated as characteristics of quasi-F1 to quasi-F3 in FIG. 7) are obtained. In other words, the aforementioned matrix processing is for creating a spectral image signal by using a quasi-bandpass filter (i.e., matrix) created in advance as described above on a color image signal.

An illustrative example of an endoscopic image created using the quasi-filter characteristics is described below.

Figure 11:
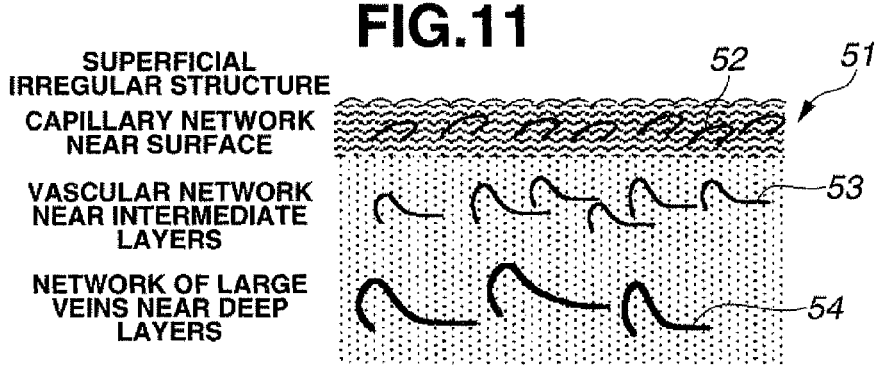
FIG. 11 is a diagram showing a layer-wise structure of biological tissue to be observed by the electronic endoscope apparatus shown in FIG. 4.

As shown in FIG. 11, tissue inside a body cavity 51 often has a distributed structure of absorbing bodies such as blood vessels which differ in a depth direction. Capillaries 52 are predominantly distributed in the vicinity of the surface layers of the mucous membrane, while veins 52 larger than capillaries are distributed together with capillaries in intermediate layers that are deeper than the surface layers, and even larger veins 54 are distributed in further deeper layers.

Figure 12:
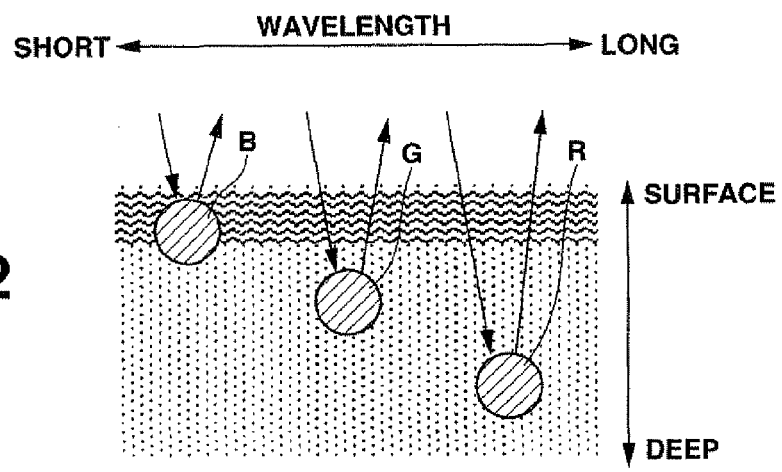
FIG. 12 is a diagram describing layer-wise reached states in biological tissue of an illumination light from the electronic endoscope apparatus shown in FIG. 4.

Meanwhile, a reachable depth of light in the depth direction with respect to the tissue inside a body cavity 51 is dependent on the wavelength of the light. In addition, as shown in FIG. 12, in the case of a light having a short wavelength such as blue (B), illumination light including the visible range only reaches the vicinity of the surface layers due to absorption characteristics and scattering characteristics of the biological tissue. Thus, the light is subjected to absorption and scattering within a range up to that depth, and light exiting the surface is observed.

Furthermore, in the case of green (G) light whose wavelength is longer than that of blue (B) light, light reaches a greater depth than the reachable range of blue (B) light. Thus, light is subjected to absorption and scattering within the range, and light exiting the surface is observed. Moreover, red (R) light whose wavelength is longer than that of green (G) light reaches an even greater depth.

Figure 13:
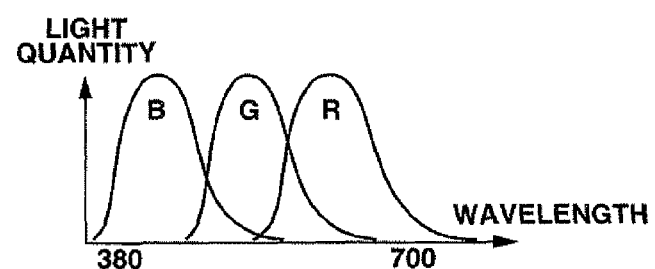
FIG. 13 is a diagram showing spectral characteristics of respective bands of white light.
Figure 15:
FIG. 15 is a second diagram showing respective band images by the white light of FIG. 13.
Figure 16:
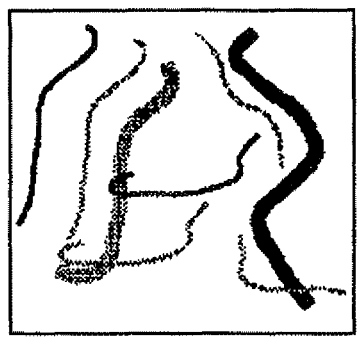
FIG. 16 is a third diagram showing respective band images by the white light of FIG. 13.

As shown in FIG. 13, with RGB light during normal observation of the tissue inside a body cavity 51, since the respective wavelength band overlap each other in the broadband:
(1) an image pickup signal picked up by the CCD 21 under B band light picks up a band image having superficial and intermediate tissue information including a large amount of superficial tissue information such as that shown in FIG. 14;

(2) an image pickup signal picked up by the CCD 21 under G band light picks up a band image having superficial and intermediate tissue information including a large amount of intermediate tissue information such as that shown in FIG. 15; and (3) an image pickup signal picked up by the CCD 21 under R band light picks up a band image having intermediate and deep tissue information including a large amount of deep tissue information such as that shown in FIG. 16.

In addition, by performing signal processing on the RGB image pickup signals at the endoscope apparatus main body 105, it is now possible to obtain a desirable endoscopic image or an endoscopic image with natural color reproduction.

The matrix processing performed by the above-described matrix computing section 436 is for creating a spectral image signal using a matrix having quasi-bandpass filter characteristics and which is created in advance as described above on a color image signal.

In addition, the user can change the quasi-bandpass filter characteristics by operating the operating panel 441 and the like to read the coefficient 443*a* stored in the LUT 443 via the coefficient control section 442 and change/set the characteristics of the matrix computation performed by the matrix computing section 436.

For example, by changing and setting the coefficient 443*a*, it is possible to set the quasi-bandpass filter characteristics created by the matrix computing section 436 to accurately create a superficial layer-side characteristic and not to created other quasi-bandpass filter characteristics. In other words, it is possible to set a band wavelength (median) value of the quasi-bandpass filter characteristics created by the coefficient 443*a* in correspondence to a feature value.

Therefore, the coefficient 443*a* is provided with a function of a living body feature value coefficient that creates a spectral image signal that emphasizes a feature value such as a vascular structure distributed among the depths from the surface of a biological tissue.

In other words, the spectral image signal creating means and the characteristic changing/setting section thereof according to the present embodiment primarily have two major advantages as described below.

By performing change/setting (including switching) so that an appropriate coefficient 443*a* (as a living body coefficient) is used in accordance with the spectral reflection characteristics of a living body, the user is able to obtain spectral image signals having high accuracy with respect to biological tissue having different spectral reflection characteristics.

In addition, when the observation of a living body portion that is likely to be observed effectively under a particular narrowband wavelength (N) is desired, the user is able to observe the living body portion in a state where S/N is preferable by performing change/setting so that a coefficient 443*a* that emphasizes and creates a spectral image signal corresponding to the narrowband wavelength (N) (or suppresses spectral image signals of other narrowband wavelengths) is used.

Figure 17:
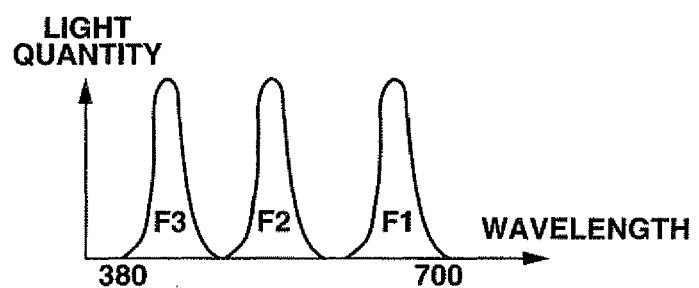
FIG. 17 is a diagram showing spectral characteristics of a spectral image created at the matrix computing section shown in FIG. 8.
Figure 18:
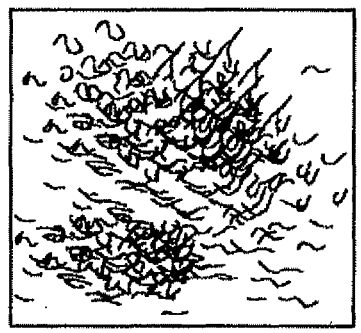
FIG. 18 is a first diagram showing respective spectral images of FIG. 17.
Figure 19:
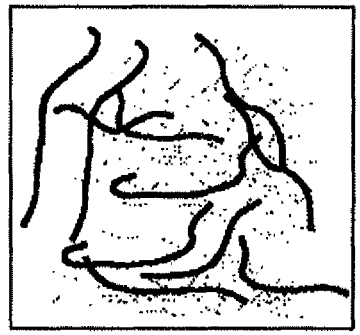
FIG. 19 is a second diagram showing respective spectral images of FIG. 17.
Figure 20:
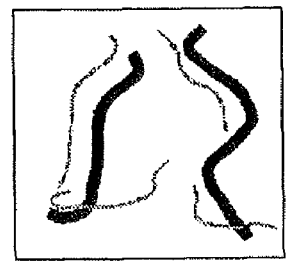
FIG. 20 is a third diagram showing respective spectral images of FIG. 17.

Meanwhile, spectral image signals F1 to F3 are obtained by using quasi-bandpass filters F1 to F3 having discrete narrow-band spectral characteristics and which are capable of extracting desired deep tissue information, as shown in FIG. 17. As shown in FIG. 17, since the respective wavelength ranges of the quasi-bandpass filters F1 to F3 do not overlap each other, (4) a band image having superficial tissue information such as that shown in FIG. 18 is picked up in the spectral image signal F3 by the quasi-bandpass filter F3;

(5) a band image having intermediate layer tissue information such as that shown in FIG. 19 is picked up in the spectral image signal F2 by the quasi-bandpass filter F2; and (6) a band image having deep layer tissue information such as that shown in FIG. 20 is picked up in the spectral image signal F1 by the quasi-bandpass filter F1.

Next, with respect to the spectral image signals $\Sigma F1$ to $\Sigma F3$ resulting from integrating the spectral image signals F1 to F3 obtained as described above, the color adjusting section 440 respectively allocates the spectral image signal F1 to the spectral channel image signal Rnbi, the spectral image signal F2 to the spectral channel image signal Gnbi, and the spectral image signal F3 to the spectral channel image signal Bnbi. Then, the spectral channel image signals Rnbi, Gnbi and Bnbi are respectively inputted via the switching section 439 to the R, G and B channels Rch, Gch and Bch of the display monitor 106.

Figure 21:
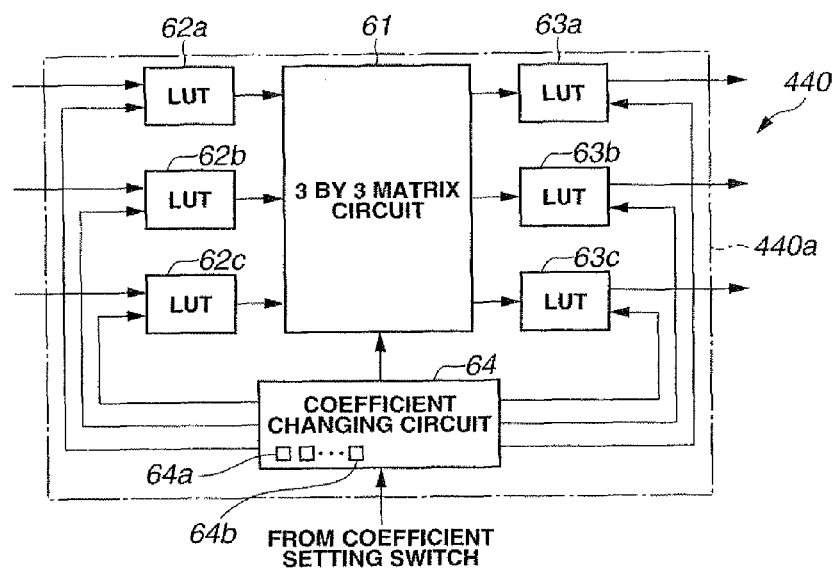
FIG. 21 is a block diagram showing a configuration of a color adjusting section shown in FIG. 4.

As shown in FIG. 21, the color adjusting section 440 is constituted by a color conversion processing circuit 440*a* comprising: a 3 by 3 matrix circuit 61 as display color converting means; three sets of LUTs 62*a*, 62*b*, 62*c*, 63*a*, 63*b* and 63*c* provided anteriorly and posteriorly to the 3 by 3 matrix circuit 61; and a coefficient changing circuit 64 as display color changing/setting means that changes table data of the LUTs 62*a*, 62*b*, 62*c*, 63*a*, 63*b* and 63*c* or the matrix coefficient of the 3 by 3 matrix circuit 61.

The spectral image signals F1 to F3 inputted to the color conversion processing circuit 440*a* are subjected to inverse $\gamma$ correction, non-linear contrast conversion and the like on a per-band data basis by the LUTs 62*a*, 62*b* and 62*c*.

Then, after color conversion is performed at the 3 by 3 matrix circuit 61, $\gamma$ correction or appropriate tone conversion processing is performed at the post-stage LUTs 63*a*, 63*b* and 63*c*.

Table data of the LUTs 62*a*, 62*b*, 62*c*, 63*a*, 63*b* and 63*c* or the matrix coefficient of the 3 by 3 matrix circuit 61 can be changed by the coefficient changing circuit 64 that changes coefficients and the like. A plurality of types of matrix coefficients 64*a* to be used when performing matrix computation by the 3 by 3 matrix circuit 61 are stored as color conversion (color adjustment) coefficients in the coefficient changing circuit 64.

By performing matrix computation using a matrix coefficient 64*a* selected via the coefficient changing circuit 64, the 3 by 3 matrix circuit 61 performs color conversion corresponding to the used matrix coefficient 64*a*.

The changing of matrix coefficients by the coefficient changing circuit 64 is based on a control signal or a switching signal from the operating panel 441 or a coefficient setting switch (or a color tone changing/setting switch) 141*b* (refer to FIG. 4) inside the endoscope switch 141 provided at, for example, an operating section of the endoscope 101.

In addition, matrix coefficients 64*a* in the coefficient changing circuit 64 include, for example, a vascular matrix coefficient 64*b* that enables a vascular structure to be displayed in an easily distinguishable color tone as a feature value retained by a living body as will be described below. The user is able to select the vascular matrix coefficient 64*b* from the coefficient changing circuit 64 by operating the coefficient setting switch 114*b*.

Incidentally, by operating the coefficient setting switch 141*b*, the user can output a control signal for changing the table data of the LUTs 62*a*, 62*b*, 62*c*, 63*a*, 63*b* and 63*c* to the coefficient changing circuit 64 in addition to a control signal for changing the matrix coefficient 64*a* used by the 3 by 3 matrix circuit 61.

Upon receiving the control signal, the coefficient changing circuit 64 reads out appropriate data from data such as the plurality of types of matrix coefficients 64*a* stored in advance in the color adjusting section 440, and overwrites the current circuit coefficient with the data.

Next, specific contents of color conversion processing will be described. Formula 22 represents an example of a color conversion equation.

$$\begin{pmatrix} R_{nbi} \\ G_{nbi} \\ B_{nbi} \end{pmatrix} = \begin{pmatrix} 1 & 0 & 0 \\ 0 & 1 & 0 \\ 0 & 0 & 1 \end{pmatrix} \begin{pmatrix} F_1 \\ F_2 \\ F_3 \end{pmatrix} \qquad (22)$$

The processing represented by Formula 22 is color conversion in which spectral image signals F1 to F3 are assigned to the spectral channel image signals Rnbi, Gnbi and Bnbi (the R channel, the G channel and the B channel as indicated by the display on the display monitor 106) in ascending order of wavelengths.

Figure 22:
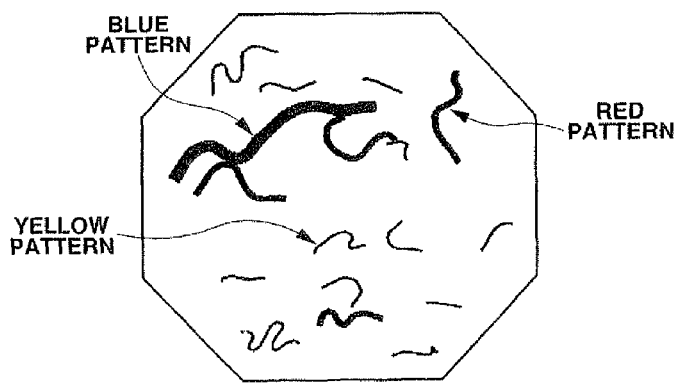
FIG. 22 is a diagram describing operations of the color adjusting section shown in FIG. 21.

In a case of observation by a color image based on the spectral channel image signals Rnbi, Gnbi and Bnbi, for example, the image shown in FIG. 22 is obtained. The spectral image signal F3 is reflected on a large vein existing at a deep position, and the display color thereof is depicted as a blue pattern. Since the spectral image signal F2 is strongly reflected on a vascular network near intermediate layers, a display color thereof is displayed by a red pattern.

In addition, among the vascular network, those existing near the surface of the mucosal membrane are expressed by a display color of a green pattern.

In particular, changes in the pattern in the vicinity of the surface of the mucosal membrane are important for the discovery and differential diagnosis of early-stage diseases. However, a yellow pattern tends to have a weak contrast against background mucosa and therefore low visibility.

In this light, in order to reproduce patterns in the vicinity of the surface of the mucosal membrane with higher visibility, a conversion expressed by Formula 23 becomes effective.

$$\begin{pmatrix} R_{nbi} \\ G_{nbi} \\ B_{nbi} \end{pmatrix} = \begin{pmatrix} 1 & 0 & 0 \\ 0 & \omega_G & \omega_B \\ 0 & 0 & 1 \end{pmatrix} \begin{pmatrix} F_1 \\ F_2 \\ F_3 \end{pmatrix} \qquad (23)$$

The processing represented by Formula 23 is an example of a conversion in which the spectral image signal F1 is mixed with the spectral image signal F2 at a certain ratio and created data is newly used as the spectral G channel signal Gnbi. Adopting the conversion enables greater clarification of the fact that absorption/scattering bodies such as a vascular network differs according to depth positions. Therefore, by adjusting the matrix coefficient 64*a* via the coefficient changing circuit 64, the user is able to adjust display colors so that a preferable display effect is achieved.

Such an operation is performed as follows.

In conjunction with an operation, by a user, of the operating panel 441 or a mode switching switch 141*c* (refer to FIG. 4) inside the endoscope switch 141 provided at an operating section of the endoscope 101, the matrix coefficient 64*a* is set to a default value within the color adjusting section 440 (color conversion processing circuit 440*a*) from a through operation.

A through operation in this case refers to a state in which a unit matrix is mounted on the 3 by 3 matrix circuit 61 and a non-conversion table is mounted on the LUTs 62*a*, 62*b*, 62*c*, 63*a*, 63*b*, and 63*c*. This means that, for example, preset values of $\omega_G$=0.2, $\omega_B$=0.8 are to be provided as default values of the matrix coefficient 64*a*.

Then, by operating the operating panel 441 or the coefficient setting switch 1411*b* provided at the endoscope switch 141 placed at an operating section of the endoscope 101, the user selects the vascular matrix coefficient 64*b* from the coefficient changing circuit 64. Next, as the matrix coefficient of the 3 by 3 matrix circuit 61, changing/setting is performed from the above-mentioned preset values $\omega_G$=0.2, $\omega_B$=0.8 to, for example, $\omega_G$0.4, $\omega_B$=0.6. An inverse γ correction table and a γ correction table are applied as required to the LUTs 62*a*, 62*b*, 62*c*, 63*a*, 63*b* and 63*c*.

While the color conversion processing circuit 440*a* according to the present embodiment is illustrated by an example in which color conversion is performed by a matrix computing unit constituted by the 3 by 3 matrix circuit 61, the present invention is not limited to this example. Instead, color conversion processing means may be configured using a numerical processor (CPU) or an LUT.

Figure 23:
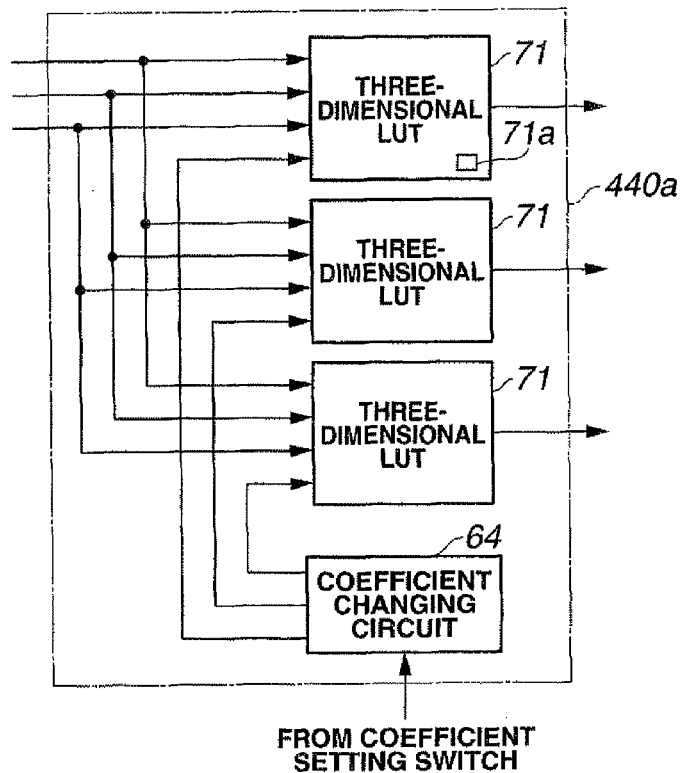
FIG. 23 is a block diagram showing a configuration of a modification of the color adjusting section shown in FIG. 4.

For example, in the above-described embodiment, while the color conversion processing circuit 440*a* is illustrated by a configuration centered around the 3 by 3 matrix circuit 61, similar operations and advantages may be realized by replacing the color conversion processing circuit 440*a* with three-dimensional LUTs 71 corresponding to each band as shown in FIG. 23.

In this case, based on a control signal from the operating panel 441 or the coefficient setting switch 141*b* provided at the endoscope switch 141 or the like of the operating section of the endoscope 101, coefficient changing circuit 64 performs an operation for changing the contents of table data 71*a* stored in the LUT 71 (while table data 71*a* is shown in one LUT 71 in FIG. 23, table data 71*a* is similarly stored in the other LUTs 71). Subsequently, the color conversion processing circuit 440*a* shown in FIG. 23 performs color conversion processing corresponding to the changed/set table data 71*a*.

Stored inside the table data 71*a* is, for example, vascular and living body mucosal data that causes vascular structures, living body mucosal structures and the like as living body feature values to be displayed in color tones with good visibility.

Incidentally, the filter characteristics of the quasi-bandpass filters F1 to F3 are not limited to the visible range. As a first modification of the quasi-bandpass filters F1 to F3, filter characteristics may be arranged as, for example, discrete narrowband spectral characteristics such as those shown in FIG. 24. A change to such filter characteristics may be made by the user by operating the selection switch 441*a* provided on the operating panel 441 or the like to change the computation coefficient of the matrix computing section 436.

Figure 24:
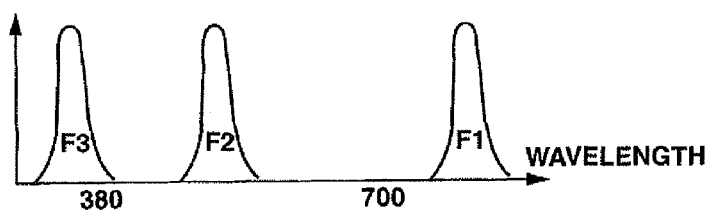
FIG. 24 is a diagram showing spectral characteristics of a first modification of the spectral image shown in FIG. 17.

The spectral image signals F1 to F3 created by the matrix computing section 436 are shown in FIG. 24 (as well as FIGS. 25 and 26 described below) as spectral characteristics similar to the quasi-bandpass filters shown in FIG. 7.

By setting F3 in the near-ultraviolet range and setting F1 in the near-infrared range in order to observe irregularities on the living body surface and absorbing bodies in the vicinity of extremely deep layers, the filter characteristics of the first modification is suitable for obtaining image information unobtainable through normal observation. In other words, as shown in FIG. 24, optical image information of the deep layer-side of the living body can be obtained by F1 in the near-infrared range, and image information of irregular structures on the living body surface can be obtained by F3 in the near-ultraviolet range.

Figure 25:
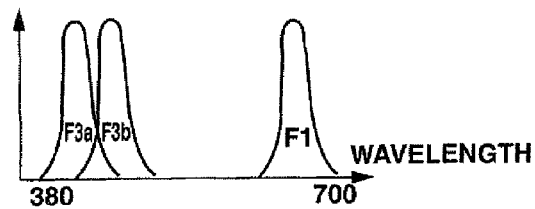
FIG. 25 is a diagram showing spectral characteristics of a second modification of the spectral image shown in FIG. 17.

In addition, as a second modification of the quasi-bandpass filters F1 to F3, as shown in FIG. 25, the quasi-bandpass filter F2 may be replaced by two quasi-bandpass filters F3a and F3b having adjacent filter characteristics in the short wavelength range. This modification takes advantage of the fact that wavelength ranges in the vicinity thereof only reach the vicinity of the uppermost layers of a living body, and is suitable for visualizing subtle differences in scattering characteristics rather than absorption characteristics. From a medical perspective, utilization in the discriminatory diagnosis of early carcinoma and other diseases accompanied by a disturbance in cellular arrangement in the vicinity of the surface of mucous membrane is envisaged.

Figure 26:
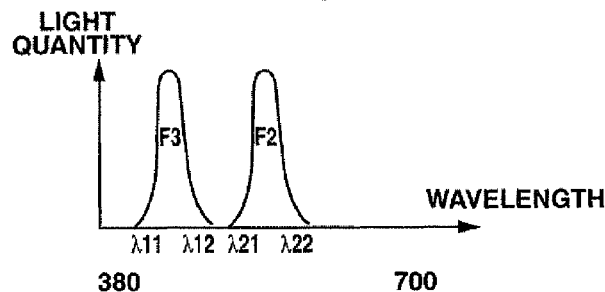
FIG. 26 is a diagram showing spectral characteristics of a third modification of the spectral image shown in FIG. 17.

Furthermore, as a third modification of the quasi-bandpass filters F1 to F3, as shown in FIG. 26, two quasi-bandpass filters F2 and F3 having dual-narrowband filter characteristics with discrete spectral characteristics and which are capable of extracting desired layer-tissue information can be created by the matrix computing section 436.

In the case of the quasi-bandpass filters F2 and F3 shown in FIG. 26, for the colorization of an image during narrowband spectral image observation, the color adjusting section 440 performs color conversion in a sequence of: spectral channel image signal Rnbi←spectral image signal F2; spectral channel image signal Gnbi←spectral image signal F3; and spectral channel image signal Bnbi←spectral image signal F3, and outputs the same to the three RGB channels Rch, Gch and Bch of the display monitor 106.

In other words, with respect to the spectral image signals F2 and F3, the color adjusting section 440 creates spectral image signals (Rnbi, Gnbi and Bnbi) to be outputted to the three RGB channels of the display monitor 106 and color-displayed on the display monitor 106 in RGB using Formula 24 below.

$$\begin{pmatrix} R_{nbi} \\ G_{nbi} \\ B_{nbi} \end{pmatrix} = \begin{pmatrix} h_{11} & h_{12} \\ h_{21} & h_{22} \\ h_{31} & h_{32} \end{pmatrix} \begin{pmatrix} F_2 \\ F_3 \end{pmatrix} \quad (24)$$

For instance, let us assume that h11=1, h12=0, h21=0, h22=1.2, h31=0, and h32=0.8.

Operations for coefficient switching and the like performed by the color adjusting section 440 in this case will be described later in the second embodiment.

Figure 27:
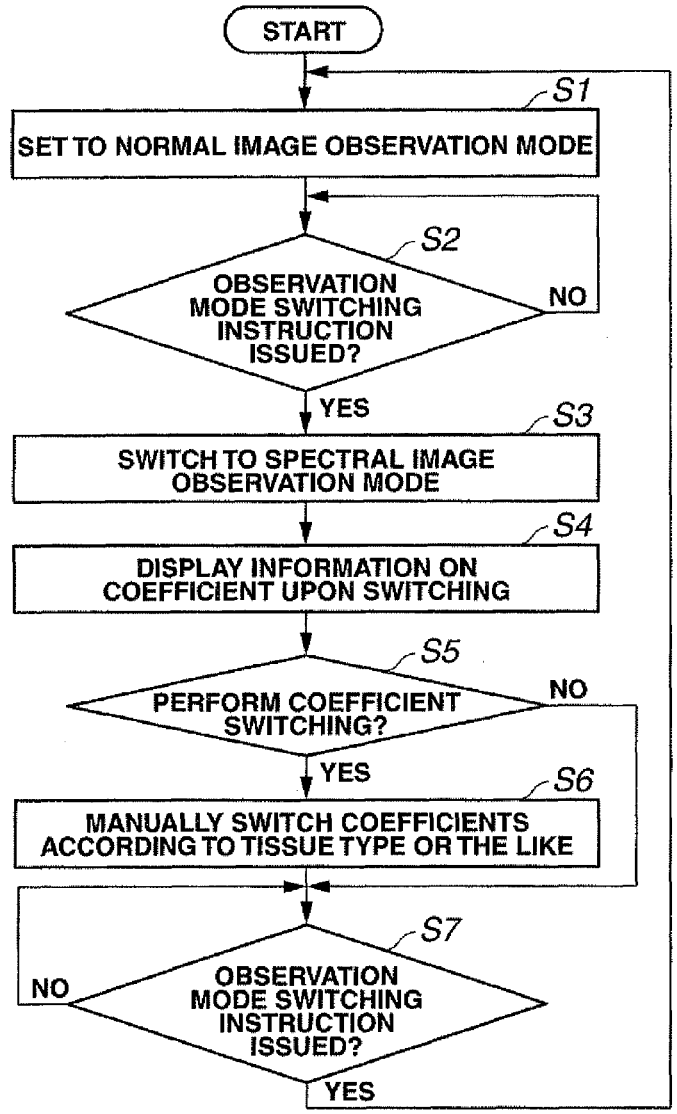
FIG. 27 is a flowchart showing an operation of manually performed coefficient switching when switching is made to a spectral image observation mode.

A flowchart of operations in a case of living body surface observation in which the user such as an operator manually performs coefficient setting (coefficient switching) of the matrix computing section 436, which creates spectral image signals, in accordance with the type of the living body to be observed, features and the like as described above and according to the present embodiment is as shown in FIG. 27.

Upon activation, the control section 42 and the like assume an operating state and control the respective sections so that an operating state in normal observation mode is assumed as an initial setting as shown in step S1.

Then, an observation mode switching instruction wait state is assumed as shown in step S2. When an observation mode switching instruction is issued by the operator from the operating panel 441 or the like, the control section 42 performs control for switching to an operating state in spectral observation mode as shown in step S3.

Furthermore, when performing control for switching to the operating state in spectral observation mode, as shown in step S4, the control section 42 performs control so as to display, for example, information on a coefficient set as spectral image observation mode upon switching on the display monitor 106. As for the contents of display information of the coefficient during switching in step S4, for example, information on a coefficient set at the matrix computing section 436 during spectral image observation mode set during switching is displayed.

Subsequently, in a next step S5, the control section 42 confirms with the user whether coefficient switching (selection) is to be performed.

The user (operator) then determines whether switching is to be performed according to features and the type of a subject to be actually examined or, more specifically, features, type or the like of living body mucosa. In the case where switching is to be performed, an operation for manually switching the coefficient according to the type of the subject to be examined or, more specifically, the tissue type or the like of living body mucosa is performed as shown in step S6. Then, together with the case where switching is not performed, the routine proceeds to step S7.

As described, switching may either be performed based on a type of the living body mucosa that is actually observed such as a name of an observed region including esophagus mucosa, gastric mucosa and large intestinal mucosa, or based on a spectral reflectance characteristic, type or the like of an observation target portion such as the tissue types (i.e., name and type of epithelia constituting the living body mucosa to be observed).

For example, the epithelial tissue of esophagus mucosa is stratified squamous epithelia, while gastric and large intestinal mucosa are covered by simple columnar epithelia. This means that basic spectral characteristics thereof differ. Therefore, the use of a spectral image estimation matrix calculated using basic spectral characteristics estimated from a set of esophagus mucosal spectral reflectance data in an examination of the large intestine is unlikely to produce desired results.

In order to obtain accurate spectral images, it is necessary to perform the matrix computation using basic spectral characteristics corresponding to the type or tissue type of living body mucosa. Even in actual observation, it is desirable to use appropriate matrix computation.

Accordingly, in the present embodiment, the operator operates the selection switch 441b (refer to FIG. 4) as coefficient setting/switching means constituting interface means which is provided on, for example, the operating panel 441 or the like, and which performs coefficient switching or coefficient selection of the matrix computing section 436.

As a result of the operation, a coefficient 443a corresponding to the spectral characteristics of the observation object is read from the LUT 443, and switching is performed so that appropriate matrix computation is performed using the coefficient 443a.

In step S7, the control section 42 enters an observation mode switching instruction wait state. Then, when the operator performs a switching instruction operation, the control section 42 returns to step S1 and switches to normal image observation mode. Thereafter, the processing described above is repeated. Incidentally, in the case of switching coefficients in step S5 described above, switching (selection) items according to the type of the subject to be examined, switching (selection) items according to living body features or the like may be displayed so that the user may use such items to perform, in an even easier manner, switching/setting of a coefficient corresponding to spectral characteristics that enable a living body mucosa type, a blood vessel or the like to be more suitably observed.

As seen, according to the present embodiment, a quasi-narrowband filter is created through electrical signal processing using a color image signal of a normal electronic endoscopic image (normal image). Accordingly, the present embodiment enables a spectral image having desired deep portion tissue information such as a vascular pattern to be suitably obtained through coefficient setting, coefficient switching or the like by coefficient setting/switching means without having to use an optical narrow bandpass filter for spectral images, and at the same time, a color conversion coefficient of the color adjusting section 440 may be suitably set according to the spectral image.

In addition, the present embodiment makes it possible to realize a representation method that makes full use of a feature that is reachable depth information during narrowband spectral image information, and as a result, effective separation and visual confirmation of tissue information of a desired depth in the vicinity of the surface of biological tissue or, more specifically, vascular patterns or the like can be realized.

Furthermore, particularly, in a case of a three-band spectral image, by having the color adjusting section 440 respectively allocate an image corresponding to, for example, 415 nm to the color channel Bch of the display monitor 106, an image corresponding to, for example, 445 nm to the color channel Gch and an image corresponding to, for example, 500 nm to the color channel Rch, the following advantages on images may be achieved according to the present embodiment.

(a) High visibility of capillaries in an uppermost layer of a biological tissue is attained by reproducing epithelia in the uppermost layer or mucosa in a color having low chroma and reproducing capillaries in the uppermost layer in low luminance or, in other words, as dark lines.

(b) At the same time, since blood vessels positioned deeper than capillaries are reproduced by rotating towards blue in a hue-wise direction, discrimination from capillaries in the uppermost layer becomes even easier.

Incidentally, according the above-described channel allocation method, residue and bile that are observed in a yellow tone under normal observation during endoscopic examination of the large intestine are reproduced in a red tone. Moreover, with the color adjusting section 440 according to the second embodiment to be described later, substantially the same advantages may also be achieved in the case of a two-band spectral image.

Figure 28:
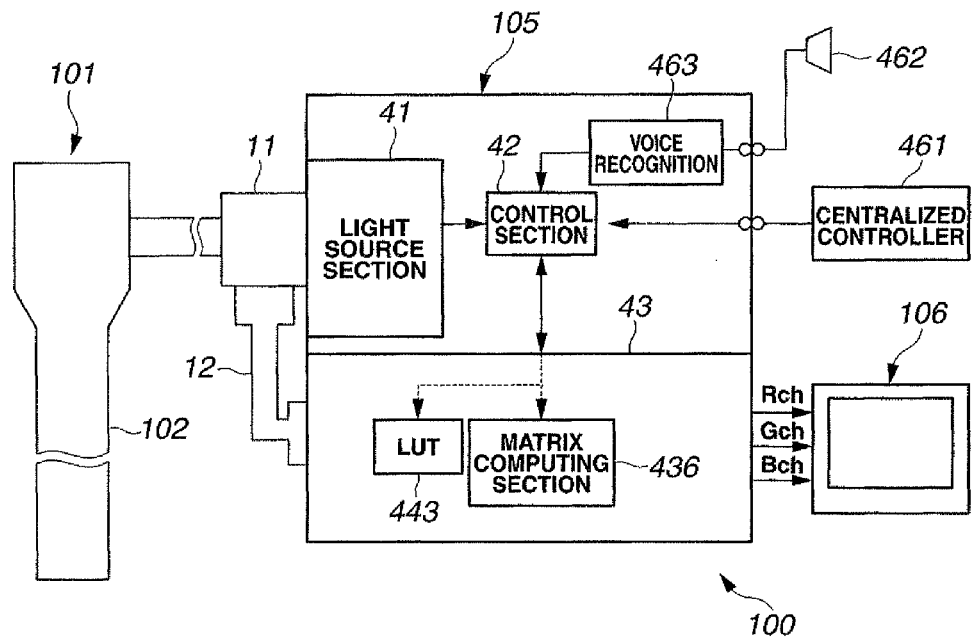
FIG. 28 is a block diagram showing a configuration of an electronic endoscope apparatus in a modification in which coefficient switching via a centralized controller or by voice input is enabled.

An electronic endoscope apparatus 100 according to a first modification of the present embodiment is shown in FIG. 28.

While the electronic endoscope apparatus 100 according to the first embodiment is arranged so that switching/setting of coefficients of the matrix computing section 436 is operable from the operating panel 441 or the like, the present modification is arranged so that the operation can be performed from a centralized controller 461 as interface means connected to the control section 42.

In addition, for the present modification, a microphone 462 that accepts a voice-based coefficient switching instruction from a user as an electric signal is connected to the main body 105, and at the same time, a voice recognition circuit 463 is provided inside the main body 105. Accordingly, a voice signal from the user inputted via the microphone 462 is subjected to voice recognition at the voice recognition circuit 463, and a voice recognition result thereof is inputted to the control section 42.

Subsequently, in accordance with an instruction signal such as for coefficient switching from the user through the centralized controller 461 or by voice through the microphone 462, the control section 42 suitably performs matrix computation by the matrix computing section 436 in accordance with a coefficient 443a stored in the LUT 443. Incidentally, in the present modification (as well as a next modification), the control section 42 is shown to be configured so as to combine the functions of the coefficient control section 442 shown in FIG. 4. It is needless to say that coefficient switching may be arranged to be performed from the control section 42 via the coefficient control section 442.

Furthermore, the centralized controller 461 or the like may be arranged to be used as an interface for performing an observation mode switching operation or a selection operation of an observation mode to be enabled upon power activation. In addition thereto, an interface such as a foot switch, not shown, may be provided.

Figure 29:
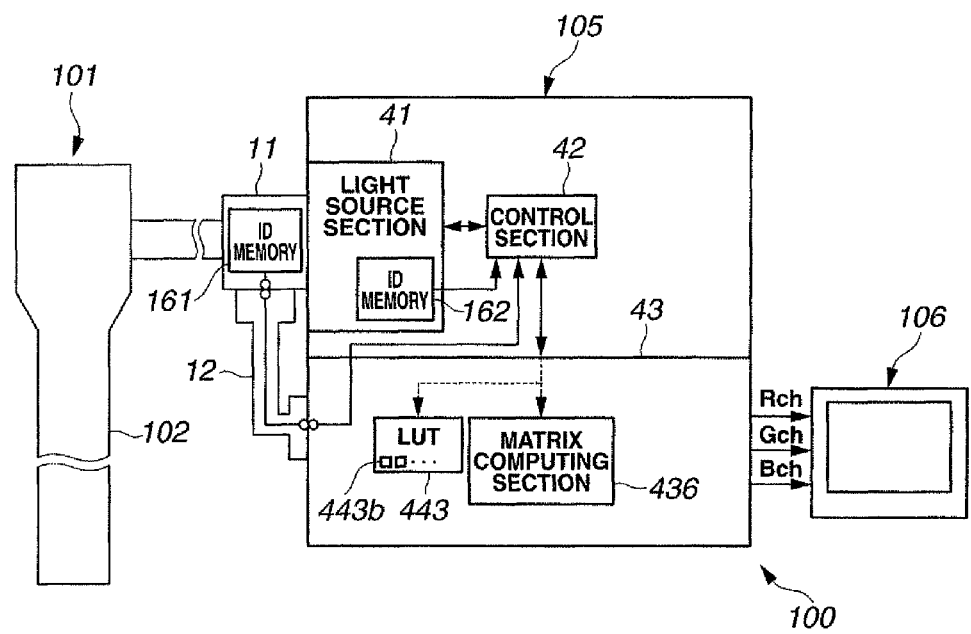

Moreover, the electronic endoscope apparatus 100 as an illustrative example of a biological observation apparatus may be configured similar to a second modification shown in FIG. 29. In the electronic endoscope apparatus 100 according to the second modification shown in FIG. 29, an ID memory 161 is provided in, for example, the connector 11 inside the endoscope 101 and an ID memory 162 is provided in, for example, the light source section 41 of the main body 105.

ID information respectively stored in the ID memory 161 and the ID memory 162 are inputted to the control section 42 upon, for example, power activation. In accordance with components of the electronic endoscope apparatus 100 such as the endoscope 101 which are actually combined to constitute the electronic endoscope apparatus 100, the control section 42 performs control so that coefficient switching/setting by the matrix computing section 436 automatically attains an appropriate setting in accordance with the components of the electronic endoscope apparatus 100 side.

Figure 30:
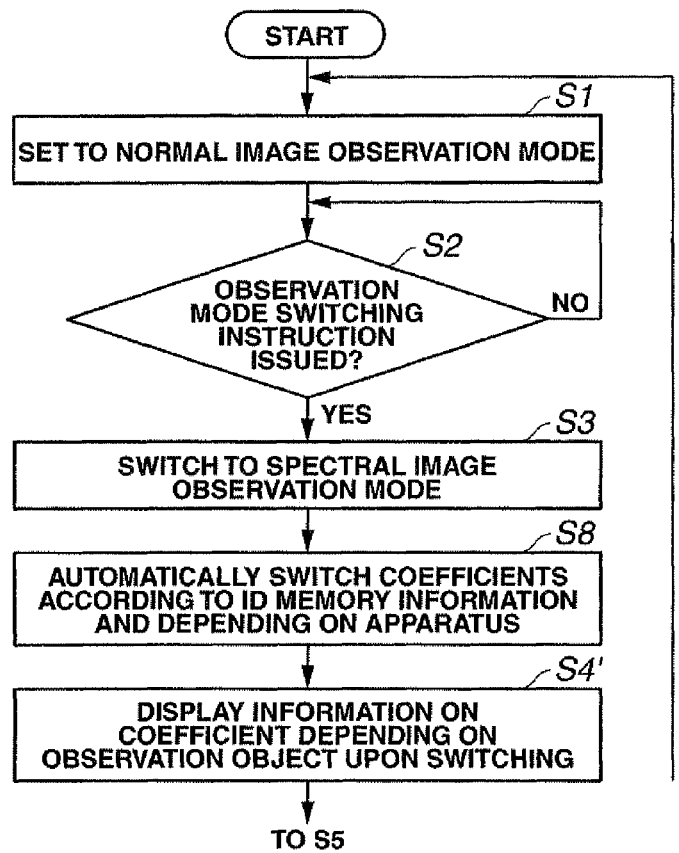
FIG. 30 is a flowchart of an operation of performing coefficient switching by an apparatus-side combination in the case of the configuration shown in FIG. 29.

Operations in this case are as depicted in a flowchart shown in FIG. 30. The operations depicted in FIG. 30 are basically the operations depicted in FIG. 27 but now arranged so that the processing represented by step S8 is performed between steps S3 and S4.

After switching to spectral image observation mode in step S3, in the next step S8, the control section 42 reads information from the ID memory 161 of the endoscope 101 and the ID memory 162 of the light source section 41. Then, based on color image pickup characteristics of the CCD 21 employed in the endoscope 101, the type or emission wavelength characteristics (spectral characteristics) of the lamp 15 of the light source section 41 or the like from the respective information, the control section 42 reads a coefficient that is suitable for the computation at the matrix computing section 436 from the LUT 443. Subsequently, the control section 42 sends the coefficient to the matrix computing section 436 and performs automatic switching/setting of coefficients.

Incidentally, (in addition to the coefficient 443a shown in FIG. 4), the LUT 443 shown in FIG. 29 stores a plurality of coefficients 443b corresponding to color image pickup characteristics of the CCD 21, a type and emission wavelength characteristics (spectral characteristics) of the lamp 15 of the light source section 41, or the like.

Subsequently, the routine proceeds to the processing of step S4' that corresponds to the next step S4 in FIG. 27. In step S4', the control section 42 performs control so that information on the coefficient set according to an observation object that is set (by default or by a previous selection) during switching is displayed. Processing subsequent to the step S4' is the same as the case shown in FIG. 27.

According to the present modification, even in a case where the spectral characteristics of color filters of the CCD 21 mounted on the endoscope 101 to be actually connected and used differ according to the type or individual difference of the endoscope 101 or according to the type (for example, a type such as a halogen lamp, a xenon lamp or the like which have different emission spectral characteristics) or individual difference of the lamp 15 as a light source in the light source section 41, influences of such differences may be reduced and a spectral image with greater reliability may be obtained.

Incidentally, in a case where the ID memory 161 or the like is not provided, switching/setting to a suitable coefficient may be performed manually. In addition, a mode in which coefficient switching/setting is performed automatically and a mode in which coefficient switching/setting is performed manually may be provided to be selected by the user to perform coefficient switching/setting regardless of the availability of the ID memory 161 or the like.

Furthermore, in the present modification, while a mode in which the setting of a coefficient used when performing matrix computation by the matrix computing section 436 has been described, a coefficient used when performing color adjustment or color conversion by the color adjusting section 440 may be automatically set in the same manner. This arrangement enables automatic setting to the same color tone state in the case where a combination of the endoscope 101 and the like which constitute the electronic endoscope apparatus 100 are the same. In addition, the respective coefficients may be arranged to be automatically set at the matrix computing section 436 and the color adjusting section 440 based on ID information from the ID memories 161 and 162 or the like.

In the case where the light source section 41 is incorporated into the endoscope apparatus main body 105, the control section 42 may be arranged to perform automatic setting of coefficients solely by ID information of the endoscope 101 side. It is needless to say that, even in the case where the light source section 41 is incorporated into the endoscope apparatus main body 105) the coefficient used when performing matrix computation by the matrix computing section 436 may be arranged to be automatically set while also taking into consideration the spectral characteristics of the lamp 15 in the light source section 41.

Figure 31:
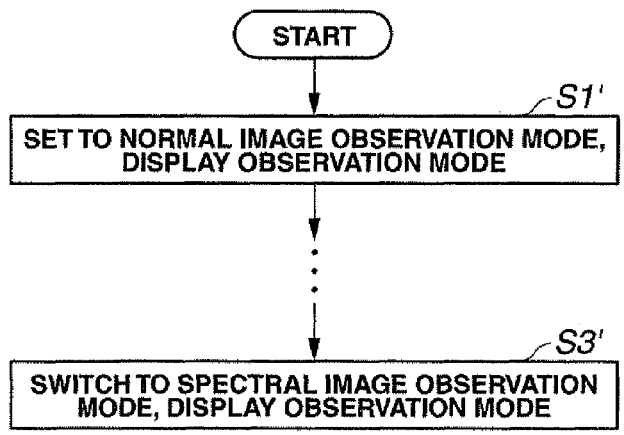
FIG. 31 is a flowchart showing a portion of operations in a case where display of observation modes is further enabled in the operation shown in FIG. 30.

When setting or switching/setting of an observation mode is performed as shown in FIG. 31 in the processing shown in FIG. 27 or 30, the observation mode may be further arranged to be explicitly displayed.

In the example shown in FIG. 31, in the first step S1', the control section 42 sets normal image observation mode in the same manner as in step S1. Furthermore, the control section 42 performs control so as to explicitly display the observation mode.

For example, as shown in FIG. 32A, the control section 42 performs control so that "NI", which explicitly indicates that the present mode is normal image observation mode or that a normal image is being displayed, is displayed, for example, under a display area of a normal image displayed on the display monitor 106. The control section 42 may perform control so that "Normal Imaging", "normal image" or the like is displayed instead of displaying character information using "NI".

In addition, similarly in step S3' corresponding to step S3, when switching is performed to the spectral image observation mode, the control section 42 further explicitly displays the observation mode.

For example, the control section 42 performs control so that "NBI", which explicitly indicates a spectral image, is displayed, for example, under a display area of a spectral image as shown in FIG. 32B. The control section 42 may perform control so that "Narrow Band Imaging", "spectral image" or the like is displayed instead of causing "NBI" to be displayed.

This arrangement enables the user to confirm the observation mode that is actually set in a more reliable manner.

In addition, in the case of a normal image such as that shown in FIG. 32C, control may be performed so that "NI" or the like is not displayed while "NBI" is displayed only in the case of a spectral image.

Furthermore, while examples in which an observation mode is explicitly indicated on the display monitor 5 are shown in FIGS. 32A to 32C, interface means may be formed that enables an observation mode to be explicitly displayed on the operating panel 441 through which the user can confirm the observation mode state.

For example, as shown in FIG. 32D, an LED 91 for explicitly displaying an observation mode (in this case, the spectral image observation mode) is provided on the operating panel 441. The control section 42 controls the LED 91 so that the LED 91 is turned off during normal image observation mode and turned on during spectral image observation mode.

It is even better if characters of "NBI" or the like which indicate whether the on/off state of the LED 91 is the spectral image observation mode or not are displayed in the vicinity of the LED 91.

Furthermore, in the example shown in FIG. 32E, an LED 92 on which the characters "NBI" themselves or a periphery of the characters are lighted is provided on the operating panel 441. Accordingly, the control section 42 may control the LED 92 so that the LED 92 is turned off during normal image observation mode and turned on during spectral image observation mode as described above.

Moreover, in the example shown in FIG. 32F, an LED 93 on which the characters "NBI" themselves or a periphery of the characters are lighted is provided on the operating panel 441. Accordingly, the control section 42 may control the LED 93 so that the LED 93 is lighted (displayed) in different colors according to observation mode such as the case where the LED 93 is lighted in green during normal image observation mode to indicate a turned-off state and lighted in white during spectral image observation mode. Incidentally, while examples in which information regarding an observation mode or an observation image is displayed on the operating panel 441 as interface means have been described, information regarding an observation mode or the like may be arranged to be displayed on a keyboard or other interface means.

Figure 33:
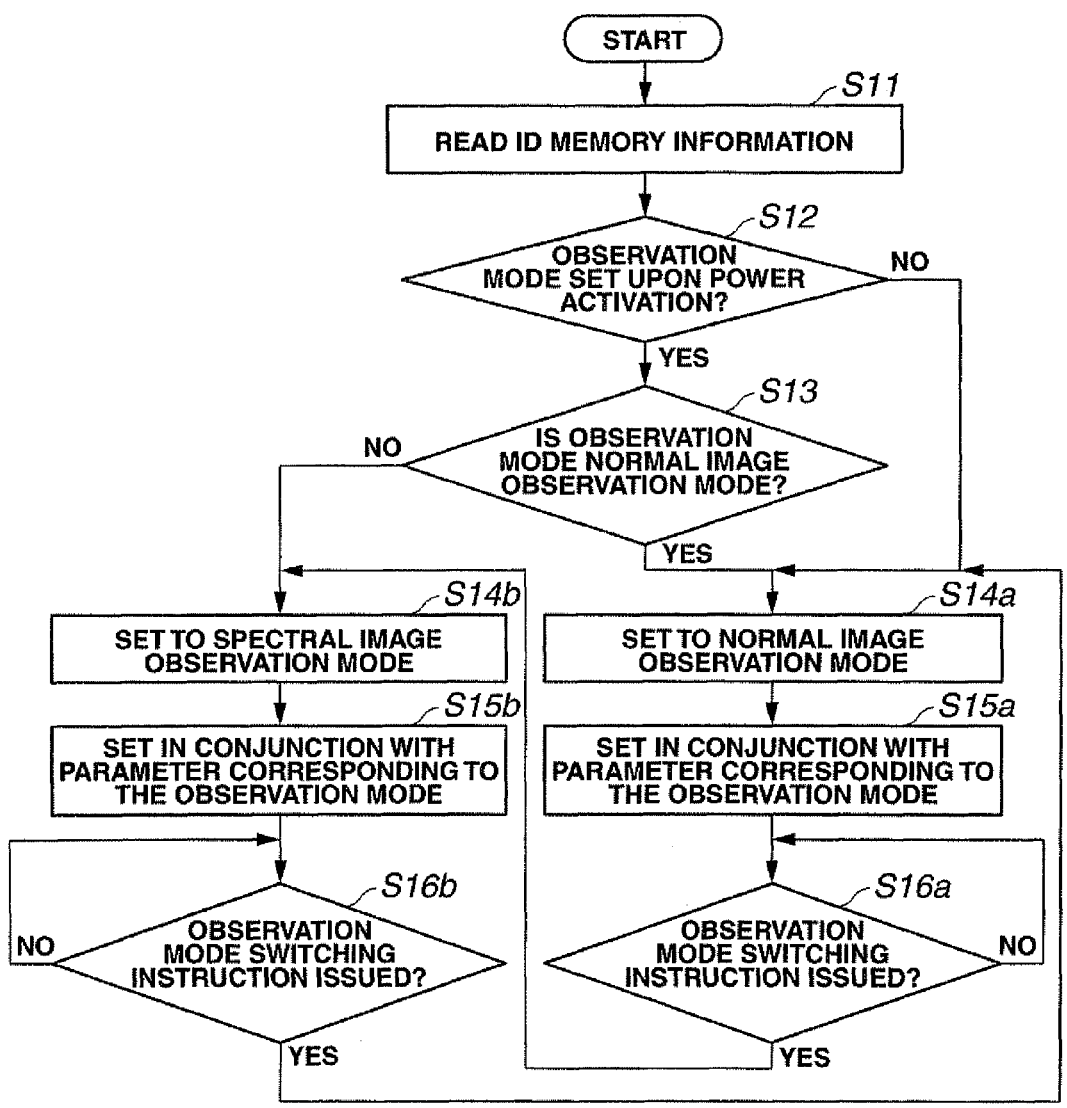
FIG. 33 is a flowchart of an operation for also changing and setting a parameter in conjunction with switching of observation modes in the case of the configuration shown in FIG. 29.

In the case of a configuration similar to that shown in FIG. 29, coefficient setting suitable for each observation mode may be arranged to be performed in conjunction to the switching of observation modes using information written into the ID memory 161 or the like of the endoscope 101 as shown in FIG. 33.

Upon power activation, in a first step S11, the control section 42 reads information of the ID memory 161 of the endoscope 101 and the ID memory 162 of the light source section 41.

In a next step S12, the control section 42 judges whether an observation mode to be enabled upon power activation has been set. Observation mode setting information is stored in, for example, a nonvolatile memory, not shown, inside the control section 42. Incidentally, when an observation mode to be enabled upon power activation is set by the user from the keyboard 451, the control section 42 stores the setting information into the nonvolatile memory.

Then, the control section 42 reads the setting information and enables the preset observation mode. In addition, when setting has not been performed, for example, the normal image observation mode is enabled.

Therefore, in step S12, when the control section 42 judges that an observation mode to be enabled upon power activation has been set, in the next step S13, the control section 42 judges whether the normal image observation mode has been set.

Subsequently, when the normal image observation mode has been set or when an observation mode upon power activation has not been in step S12, the routine proceeds to step S14a, whereby the control section 42 sets the electronic endoscope apparatus 100 to normal image observation mode and performs activation.

In addition, when the normal image observation mode has been set, the control section 42 sets a parameter (coefficient) corresponding to the observation mode. In other words, as indicated by step S15a, setting is performed in conjunction with a parameter corresponding to the observation mode.

For example, while the control section 42 performs light quantity control of the light source section 41 according to observation mode, in doing so, the control section 42 changes a target value (reference value) of light quantity control or a parameter that variably sets the target value so that the light value becomes suitable for the observation mode.

Incidentally, in the case where light quantity control may be equally performed using either a mean value or a peak value of brightness, light quantity control may be arranged so that the user can select a type to be used for light quantity control. In addition, the control section 42 also stores separately for normal image observation and for spectral image observation, in a nonvolatile memory or the like therein, information such as set values of various parameters including type of contour enhancement, type of tone conversion, type of color painting. Upon mode switching, the control section 42 also automatically switches setting conditions of parameters other than those required by the observation mode.

Such controls performed by the control section 42 enables normal images to be displayed with suitable brightness, color tones appropriate for diagnosis, correct contour state and the like.

After setting the parameters, in step S16a, the control section 42 enters an observation mode switching instruction wait state. After an observation mode switching instruction is issued, the routine proceeds to step S14b.

In addition, in step S13, when the setting of observation mode upon power activation is not the normal image observation mode, the routine proceeds to step S14b in which the control section 42 sets the observation mode to spectral image observation mode. Furthermore, as indicated by a next step S15b, the control section 42 performs setting in conjunction with a parameter corresponding to the observation mode.

In this case, the control section 42 performs light quantity control so that a target value suitable for spectral image observation mode is attained, and at the same time, as indicated by step S8 in FIG. 30, performs switching/setting of the coefficient of the matrix computation by the matrix computing section 436 in accordance with the spectral characteristics of the color filters of the CCD 21 or the like.

In this case, the target value for spectral image observation mode is set to a value that is lower than the target value for normal image observation mode.

Subsequently, the control section 42 performs light quantity control using parameters such as the above-mentioned target value so that unsaturated R, G and B signals are inputted to the matrix computing section 436 in order to ensure that a spectral image signal is appropriately calculated, and at the same time, performs coefficient switching so that the matrix computing section 436 can appropriately calculate a spectral image signal in accordance with the spectral characteristics of the color filters or the like. In other words, the control section 42 ensures that signal processing is appropriately performed. In addition, the control section 42 may be arranged so as to also set other parameters for the above-mentioned contour enhancement and the like to values suitable for spectral image observation.

After setting the parameters, in step S16b, the control section 42 enters an observation mode switching instruction wait state. After an observation mode switching instruction is issued, the routine proceeds to step S14a.

According to the present modification, an observation mode to be enabled upon power activation may be set to an observation mode in accordance with user settings. In addition, setting of various parameters can be performed smoothly in conjunction with switching of observation modes so that image display and signal processing are performed in a state suitable to the switched observation mode while minimizing setting operations by the user. Therefore, according to the present modification, operability is improved.

Incidentally, while an example in which an observation mode to be enabled upon power activation is set using information set by the user prior to power activation was used in the description of operations shown in FIG. 33, an observation mode to be enabled upon power activation may be set by performing specific key input upon, for example, power activation as described below.

Figure 34:
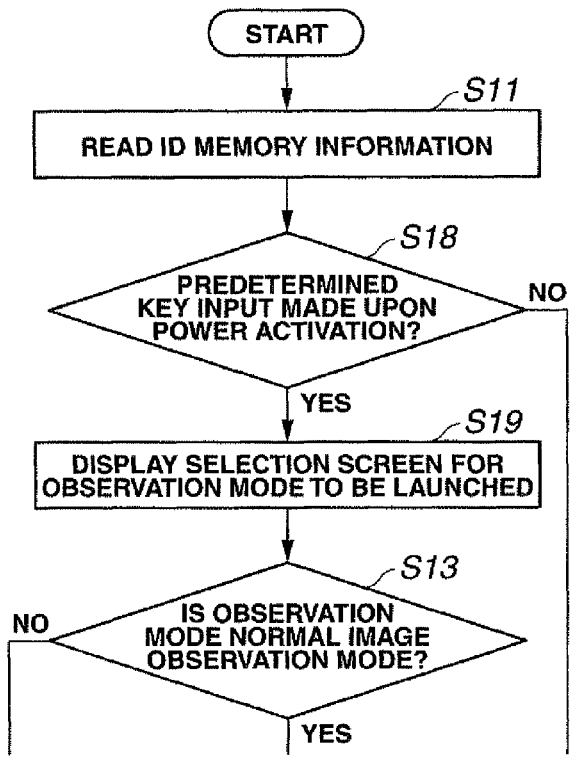
FIG. 34 is a flowchart of a portion of operations of a modification of FIG. 33.

A portion of operations in this case is depicted in the flowchart shown in FIG. 34. For example, when power is activated, the control section 42 performs the same processing as in step S11 of FIG. 33. Subsequently, as represented by step S18, the control section 42 performs judgment over a predetermined time period on whether a predetermined key input operation that is preset to select an observation mode to be enabled upon power activation is performed.

When the user desires to select an observation mode to be enabled upon power activation, the user operates a preset predetermined key on the keyboard 451 or the like to perform key input. When it is judged that the predetermined key input has been performed, as represented by step S19, the control section 42 performs control so that a selection screen for selecting an observation mode to be enabled upon power activation is displayed.

The control section 42 causes a selection screen to be displayed which inquires, for example, whether the normal image observation mode or the spectral image mode should be enabled, and requests a selection by the user.

Subsequently, in approximately the same manner as in step S13 of FIG. 33, the control section 42 judges whether the selected observation mode is the normal image mode. On the other hand, when it is judged in the judgment processing of step S18 that the predetermined key input has not been performed, the routine proceeds to step S14a of FIG. 33. Subsequent processing is the same as that of FIG. 33.

According to the present modification, the user is able to perform selection/setting of an observation mode upon activation. Although selection of an observation mode is arranged to be made by performing the above-mentioned key operation, as a modification thereof, an observation mode to be enabled upon power activation may be arranged to be determined by a key operated in advance.

For the first embodiment (including modifications thereof) above, a configuration in which the matrix computation by the matrix computing section 436 for spectral image estimation is suitably switched was described. However, as is the case of the second embodiment described below, the computation coefficient of the color adjustment means may be arranged to be suitably switched.

Second Embodiment

Figure 35:
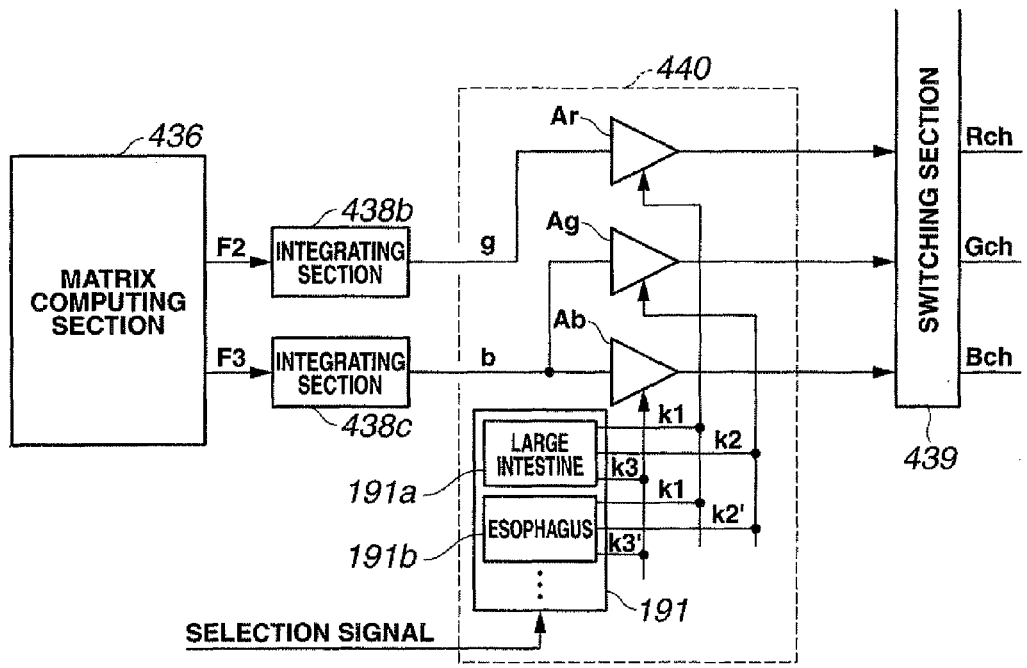
FIG. 35 is a block diagram showing a configuration of a peripheral portion of a color adjusting section in an electronic endoscope apparatus according to a second embodiment of the present invention.

Next, the second embodiment of the present invention will be described with reference to FIG. 35. FIG. 35 shows a configuration of a peripheral portion of a color adjusting section in an electronic endoscope apparatus according to the second embodiment. The present embodiment is an illustrative example in which color adjustment by the color adjusting section 440 is suitably performed using, for example, two spectral image signals ΣF2 and ΣF3 in the configuration shown in FIG. 4 of the first embodiment. Therefore, in the present embodiment, the integrating section 438a shown in FIG. 4 has not been provided, a spectral channel image signal to be color-displayed on the display monitor 5 is created from the two spectral image signals ΣF2 and ΣF3.

In the present embodiment, as an illustrative example of a method for appropriately switching the computation coefficient of the color adjustment means, color-display of a spectral image is performed using two spectral image signals ΣF2 and ΣF3 outputted from the integrating sections 438b and 438c as described below.

For example, using spectral images (spectral channel images) whose central wavelengths are approximately 415 nm and approximately 540 nm and taking digestive tract mucosa as a subject to be examined, a spectral image is displayed as a quasi-color image on the display monitor 5.

As for an allocation method of spectral images to color channels (of the display monitor 106), in consideration of the visibility on the display monitor 5, it is conceivable that a preferred example involves performing output adjustment of the 540 nm spectral channel image to the R channel of the display monitor 106 and the 415 nm spectral channel image to the B and G channels before display.

In this case, by fixing the output (signal gain) of the R channel and adjusting the output (signal gain) of the G and B channels, the color of a spectral color signal can be adjusted according to the type of epithelial tissue of biological tissue of subjects to be examined having different spectral reflectance characteristics such as esophagus mucosa and large intestinal mucosa. A configuration of the color adjusting section 440 in this case is shown in FIG. 35 as an example employing three gain variable amplifiers Ar, Ag and Ab.

For instance, if output signals to the R, G and B channels of the display monitor 5 are denoted as R, G, B, the 415 nm spectral channel image as b and the 540 nm spectral channel image as g, setting is performed so that R=k1*g, G=k2*b, and B=k3*b, where k1, k2 and k3 are weighting coefficients.

For example, weighting coefficients are set such that k1>k2>k3 when observing large intestinal mucosa, and k1>k2'>k3' and k2>k2' when observing esophagus mucosa.

In the example shown in FIG. 35, gain control data corresponding to a coefficient that regulates gain of the gain variable amplifiers Ar, Ag and Ab in advance according to the type of living body mucosa to be observed is stored in an LUT 191. When gain control data outputted from the LUT 191 is applied to a gain control end, the gain of the gain variable amplifier Ar, Ag or Ab to which is applied the gain control data is controlled.

In FIG. 35, for example, gain control data for large intestines 191a, gain control data for esophagus 191b or the like is stored in the LUT 191. By operating the selection switch 441a of the operating panel 441 or the like, the user is able to apply a selection signal (control signal) that selects the gain control data for large intestines 191a or the gain control data for esophagus 191b to the LUT 191. The LUT 191 is arranged so as to apply, based on the selection signal, corresponding gain control data to the gain variable amplifiers Ar, Ag and Ab.

According to the present embodiment configured as described above, when observation of esophagus mucosa is desired, the selection of gain control data for esophagus 191b enables stratified squamous epithelia to be reproduced in white, resulting in favorable visibility of capillaries in the epithelia.

In addition, when observation of large intestinal mucosa is desired, the selection of gain control data for large intestines 191a enables polyps and detailed patterns on mucosal surfaces to be displayed under favorable visibility. Therefore, according to the present embodiment, feature values of a living body to be used as an observation object such as the detailed structure on mucosal surfaces can be displayed under favorable visibility.

On the other hand, when a reproduction of blood vessels in a deep portion of mucosa at an even higher contrast is desired, a possible variation involves adding g spectral images that reflect the blood vessels to b spectral images at a constant ratio or the like and reproducing the blood vessels on the G channel. A portion of a configuration example for this case is shown in FIG. 36.

Figure 36:
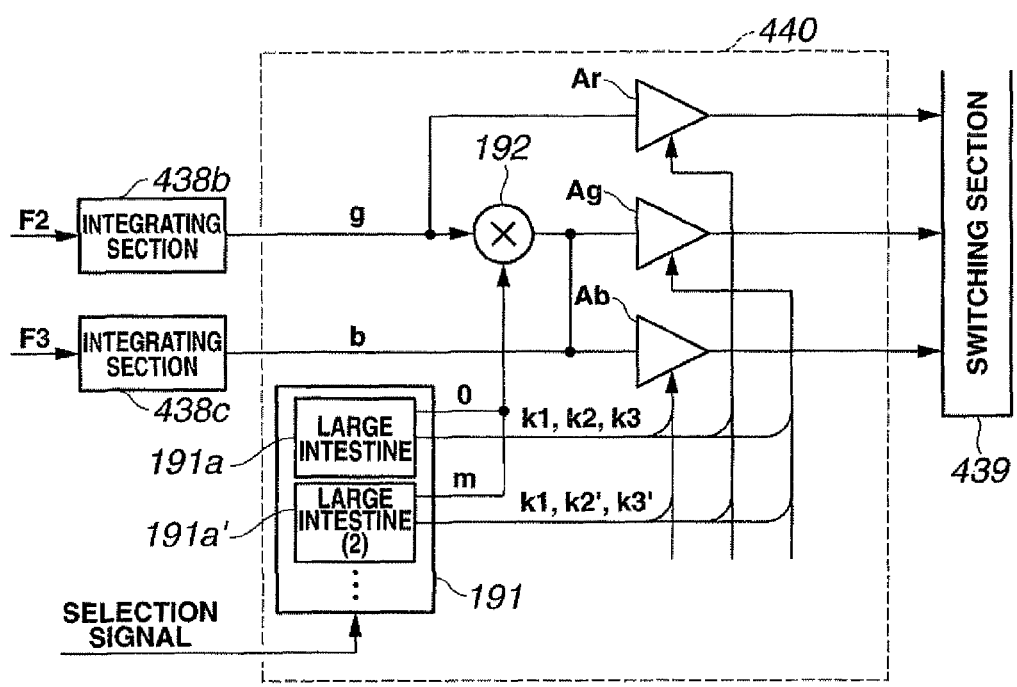
FIG. 36 is a block diagram showing a configuration of a peripheral portion of a color adjusting section in a modification of the second embodiment.

FIG. 36 is configured so that, in addition to the configuration shown in FIG. 35, g spectral images are also inputted to the gain variable amplifier Ag via a multiplier 192. In addition, a multiplier coefficient is inputted to the multiplier 192 from the LUT 191.

In this case, for example, the multiplier coefficient is set to 0 (in this case, the same effect as in FIG. 35 is attained) for the above-described gain control data for large intestines 191a in the LUT 191, and the multiplier coefficient is set to, for example, m (0<m<1) when selecting gain control data for large intestines 191a' (in the diagram, abbreviated to large intestines (2)) for reproducing deep portion-side blood vessels at an even higher contrast.

Accordingly, when the user selects gain control data for large intestines 191a via a selection signal, capillaries and detailed patterns of the large intestines can be observed in an highly visible state or, in other words, in a detailed pattern enhanced mode, and when gain control data for large intestines 191a' is selected, blood vessels on a mucosal deep portion-side can be observed in an highly visible state at high contrast or, in other words, in a deep layer blood vessel enhanced mode.

As seen, by preparing a plurality of mode of the color adjusting means that performs color adjustment switching, and by switching and using the modes through a predetermined user interface, it is possible to color display (i.e., suitable quasi-color display) a spectral image in an highly visible state.

Incidentally, while an illustrative example in which two spectral image signals ΣF2 and ΣF3 are used to perform suitable color adjustment by the color adjusting section 440 has been described for the present embodiment, color adjustment by the color adjusting section 440 may be arranged to be performed using three spectral image signals ΣF1, ΣF2 and ΣF3.

Third Embodiment

Next, a third embodiment of the present invention will be described with reference to FIGS. 37 to 40.

The present embodiment is arranged so that, when a preset condition is met during spectral image observation mode in which a spectral image is observed, control is performed so that a forced switchover to normal image observation mode is made. More specifically, when the brightness of a spectral image reaches or falls under a threshold set in order to discriminate dark images in advance, the control section 42 switches the switching section 439 to perform control for switching to normal image observation mode.

Figure 37:
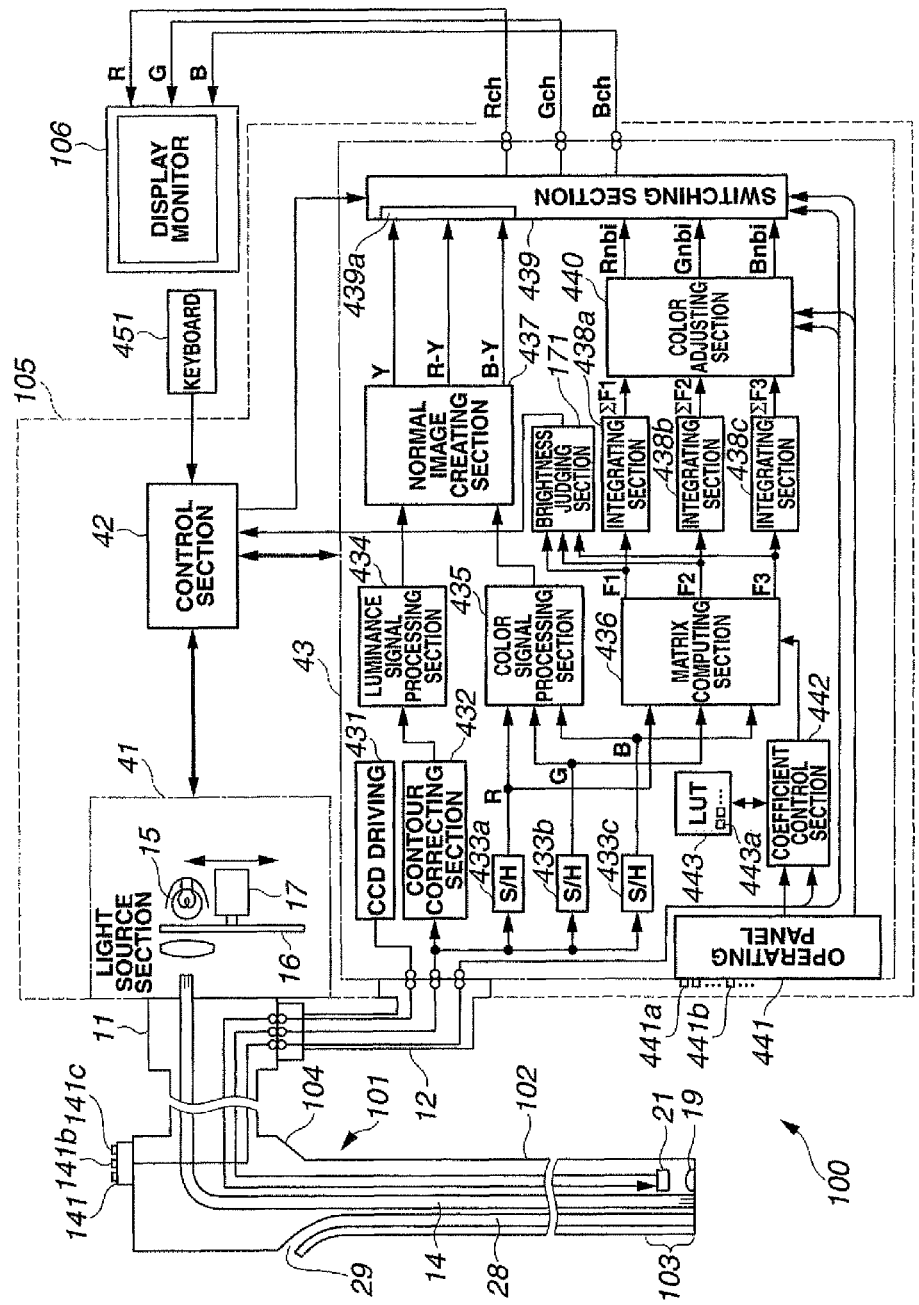
FIG. 37 is a block diagram showing a configuration of an electronic endoscope apparatus according to a third embodiment of the present invention.

An electronic endoscope apparatus 100 shown in FIG. 37 according to the third embodiment is the electronic endoscope apparatus 100 shown in FIG. 4, configured so that, for example, spectral image signals F1, F2 and F3 outputted from the matrix computing section 436 are inputted to a brightness judging section 171, and a signal of a comparison result (judgment result) of a comparison with a preset brightness level threshold Vth is outputted to the control section 42.

For example, the brightness judging section 171 performs a conditional judgment (comparative judgment) on whether a signal of a sum of absolute values of the three spectral image signals corresponding to a single frame equals or falls below the threshold Vth set in order to discriminate dark image states. Then, the brightness judging section 171 outputs the comparison result signal to the control section 42. When the condition is met, the control section 42 controls switching of the switching section 439 and performs control to forcibly switch the observation mode to normal image observation mode.

Figure 38:
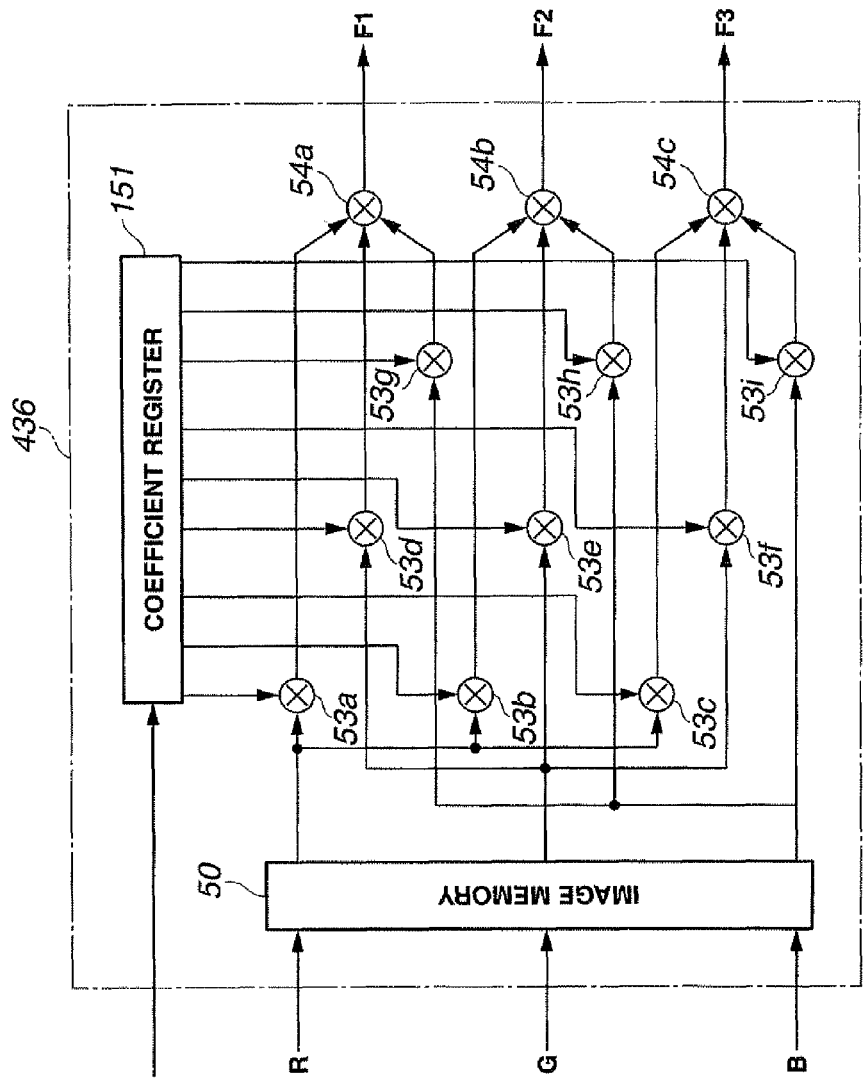
FIG. 38 is a block diagram showing a configuration of a matrix computing section.

Furthermore, in the first embodiment, while the matrix computing section 436 is configured by hardware using the resistor group 31-1a and the like as shown in FIG. 8, with the present embodiment, for example, matrix computation numerical data processing (processing by software using a program) is performed as shown in FIG. 38.

The matrix computing section 436 shown in FIG. 38 includes an image memory 50 for storing respective color image signals of R, G and B. In addition, a coefficient register 151 in which respective values of the matrix <A'> expressed by Formula 21 are stored as numerical data is provided.

The coefficient register 151 and the image memory 50 are connected to multipliers 53a to 53i; the multipliers 53a, 53d and 53g are connected to a multiplier 54a; and the output of the multiplier 54a is inputted to the integrating section 438a shown in FIG. 4.

In addition, the multipliers 53b, 53e and 53h are connected to a multiplier 54b, and the output thereof is inputted to the integrating section 438b. Furthermore, the multipliers 53c, 53f and 53i are connected to a multiplier 54c, and the output thereof is inputted to the integrating section 438c.

As for operations in the present embodiment, inputted RGB image data is temporarily stored in the image memory 50. Next, a computing program stored in a predetermined storage device (not shown) causes each coefficient of the matrix <A'> from the coefficient register 151 to be multiplied at a multiplier with RGB image data stored in the image memory 50.

Incidentally, FIG. 38 shows an example in which the R signal is multiplied by each matrix coefficient at the multipliers 53a to 53c. In addition, as is shown in the same diagram, the G signal is multiplied by each matrix coefficient at the multipliers 53d to 53f, while the B signal is multiplied by each matrix coefficient at the multipliers 53g to 53i.

As for data respectively multiplied by a matrix coefficient, outputs of the multipliers 53a, 53d and 53g are multiplied by the multiplier 54a, outputs of the multipliers 53b, 53e and 53h are multiplied by the multiplier 54d, and the outputs of the multipliers 53c, 53f and 53i are multiplied by the multiplier 54c.

An output of the multiplier 54a is sent to the integrating section 438a. In addition, the outputs of the multipliers 54b and 54c are respectively sent to the integrating sections 438b and 438c.

Furthermore, the coefficient register 151 is connected to the coefficient control section 442 shown in FIG. 4. When a selection of an observed region is performed, a matrix coefficient corresponding to the observed region is read from the coefficient control section 442 and from the LUT 443, and stored in the coefficient register 151. Then using the matrix coefficient, matrix computation processing suitable for the observed region is performed by the coefficient register 151, and spectral image signals F1, F2 and F3 are created.

Also in the case of the matrix computing section 436, a spectral image capable of clearly displaying a vascular pattern can be obtained in the same manner as in the first embodiment.

Moreover, in the present embodiment, since matrix processing is performed using software without using hardware as is the case with the first embodiment, for example, changes to each matrix coefficient or the like can be made without having to change hardware.

In addition, in a case where matrix coefficients are stored by resultant values alone or, in other words, not stored as a matrix <A'> but stored according to $S(\lambda)$, $H(\lambda)$, $R(\lambda)$, $G(\lambda)$ and $B(\lambda)$, and computed as required to determine a matrix <A'> to be used, a change can be made to only one of the elements, thereby improving convenience. For example, it is possible to change only the illumination light spectral characteristics $S(\lambda)$ or the like. Other components are similar to those of the first embodiment or the modifications thereof.

Next, an operation for switching observation modes based on a judgment result by the brightness judging section 171 according to the present embodiment will be described with reference to FIG. 39.

Upon power activation, the control section 42 and the like assume an operating state and control the respective sections so that an operating state in normal image observation mode is assumed as an initial setting as shown in step S21.

Then, an observation mode switching instruction wait state is assumed as shown in step S22. When an observation mode switching instruction is issued by the user such as an operator from the operating panel 441 or the like, the control section 42 performs control for switching to an operating state in spectral image observation mode as shown in step S23.

Consequently, spectral image signals F1, F2 and F3 subjected to matrix computation by the matrix computing section 436 are created. The spectral image signals F1, F2 and F3 are integrated by the integrating sections 438a to 438c, changed into spectral channel image signals Rnbi, Gnbi and Bnbi after color tone adjustment by the color adjusting section 440, applied to the R, G and B channels of the display monitor 106 via the switching section 439, whereby a spectral image is color-displayed on the display screen of the display monitor 106.

In the spectral image observation mode, an output signal from the matrix computing section 436 is inputted to the brightness judging section 171 that judges brightness. As represented by step S24, the brightness judging section 171 performs an operation for judging whether the spectral image has reached or fallen below a set threshold Vth.

When the condition is not met, in the next step S25, the control section 42 judges whether an observation mode switching instruction has been issued. Then, in a case where an observation mode switching instruction has not been issued, the routine returns to step S24 at which brightness judgment processing is performed.

On the other hand, in step S25, in a case where an observation mode switching instruction has been issued, as represented by step S6, the control section 42 performs control for switching to a normal observation mode operating state.

Furthermore, in the present embodiment, when it is judged by the judgment processing of step S24 that the brightness detected by the brightness judging section 171 has reached or fallen below the threshold Vth, the routine proceeds to step S26. Then, in step S26, even in a case where an observation mode switching instruction has not been issued, the control section 42 performs control for switching to a normal observation mode operating state.

After performing the control for switching to normal observation mode, the routine returns to the processing of step S22 to continue the above-described processing.

As described above, when brightness corresponding to a single frame of each image equals or falls below the threshold Vth in the spectral image observation mode, discrimination of a vascular structure or the like through a spectral image becomes difficult. Therefore, by forcibly switching to a normal observation image at the apparatus-side, a change can be made to an image that is readily observed, and a switching operation by the user becomes unnecessary. Therefore, according to the present embodiment, operability is improved.

Incidentally, as a modification of the present embodiment, coefficient setting/switching means may be formed which is arranged to switch, for example, a color tone coefficient of the color adjusting section 440 according to a brightness of a screen (scene) in a case where the brightness of the brightness judging section 171 is greater than the threshold Vth and is not dark enough to necessitate switching to normal image observation mode.

Figure 40:
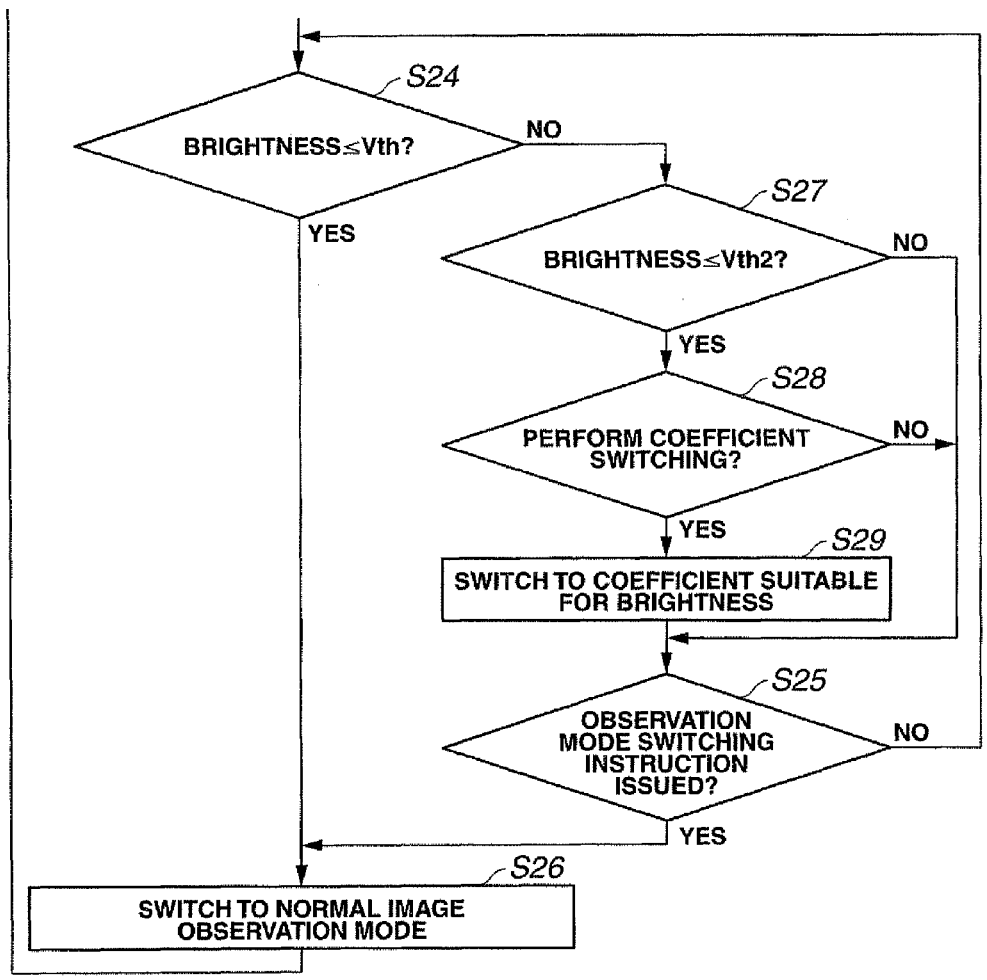
FIG. 40 is a block diagram showing a portion of operations in a modification of the third embodiment.

A portion of operations in this case is shown in FIG. 40. Although a case of two brightness levels equal to or greater than the threshold Vth will now be described as a simple example, the present modification can be similarly applied to cases having three or more brightness levels. A threshold separating the two brightnesses is assumed to be Vth2.

In step S24 of FIG. 39, when brightness is equal to or greater than the threshold Vth, as represented by step S27, the brightness judging section 171 further judges whether the brightness equals or falls below the second threshold Vth2.

Figure 39:
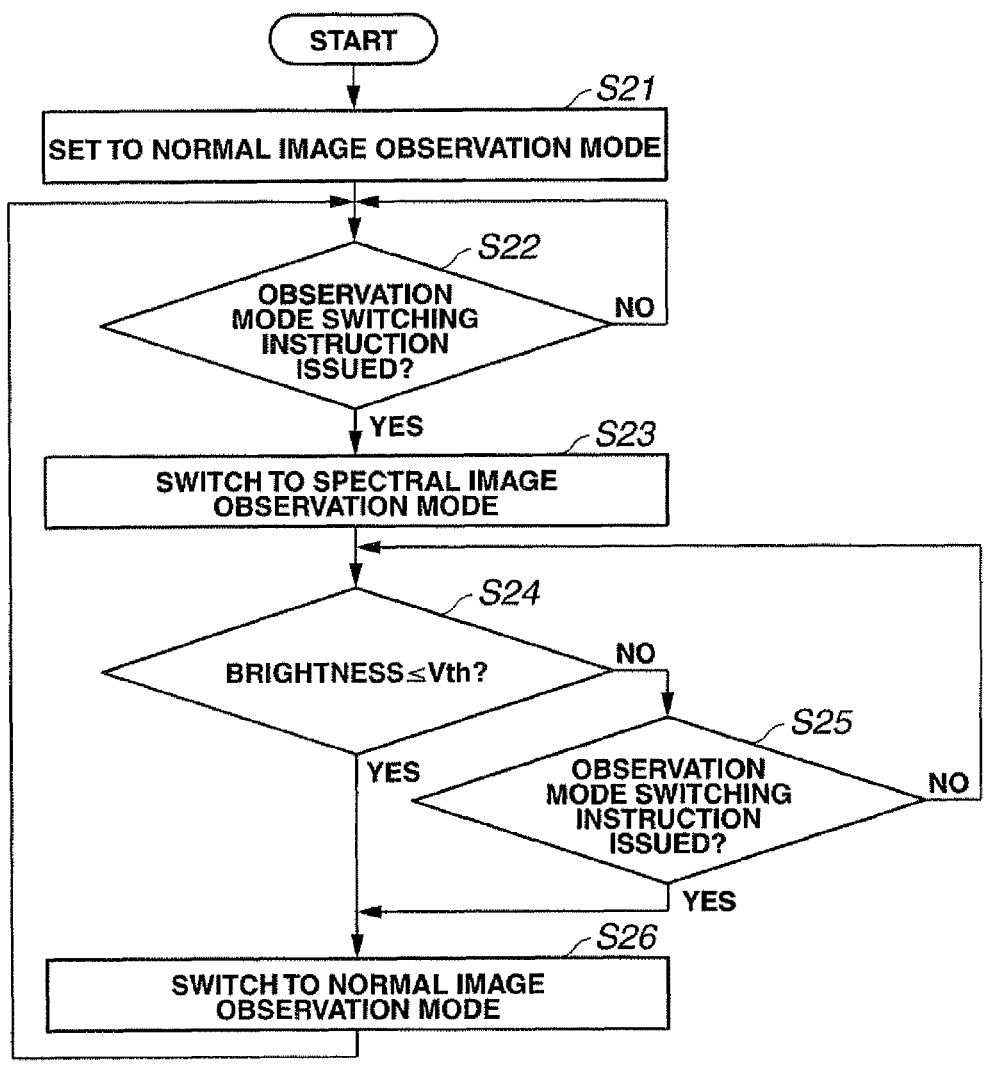
FIG. 39 is a flowchart for describing operations in the third embodiment.

Then, when the brightness is greater than the threshold Vth2, as was the case with FIG. 39, the routine proceeds to step S25 (in this case, for simplicity, it is assumed that an appropriate color tone is set when the brightness is greater than the threshold Vth2).

On the other hand, when the current brightness is lower than the threshold Vth2, as represented by step S28, the control section 42 performs display on whether coefficient switching suitable for the brightness is to be performed, and awaits a judgment by the user on whether switching is to be performed. Then, when switching is selected, as represented by step S29, the control section 42 performs coefficient switching to switch to a coefficient of a color tone appropriate for the brightness, and subsequently proceeds to step S25. In addition, the routine proceeds to step S25 even when switching is not selected. Other processing is similar to the case of FIG. 39.

According to the present modification, display can be performed with an appropriate color tone in accordance with the brightness of a scene. For example, in a darkened state, coefficient switching is performed so that chroma is increased compared to a brighter state. As a result, even when brightness is reduced, a function for enhancing visibility of a feature value of a living body from the color tone of a bright state can be maintained.

Incidentally, the present modification may be configured so that a color tone mode is selected in which display is performed by switching color tone coefficients in advance in according to a brightness value of a scene, whereby when the color tone mode is selected by the user, color tone coefficients are automatically switched in accordance with a brightness value of a scene to perform display.

Moreover, while the present embodiment is configured so that a brightness of a spectral image is judged from the spectral image, it is also possible to estimate the brightness of a spectral image from a normal image, whereby switching to normal observation mode is performed when the brightness equals or falls below a certain threshold.

While the present embodiment is arranged so that switching to normal observation mode is performed when the brightness of a spectral image equals or falls below a predetermined value corresponding to a dark image state, the present embodiment may be arranged in a similar manner to the fourth embodiment described below.

Fourth Embodiment

Figure 41:
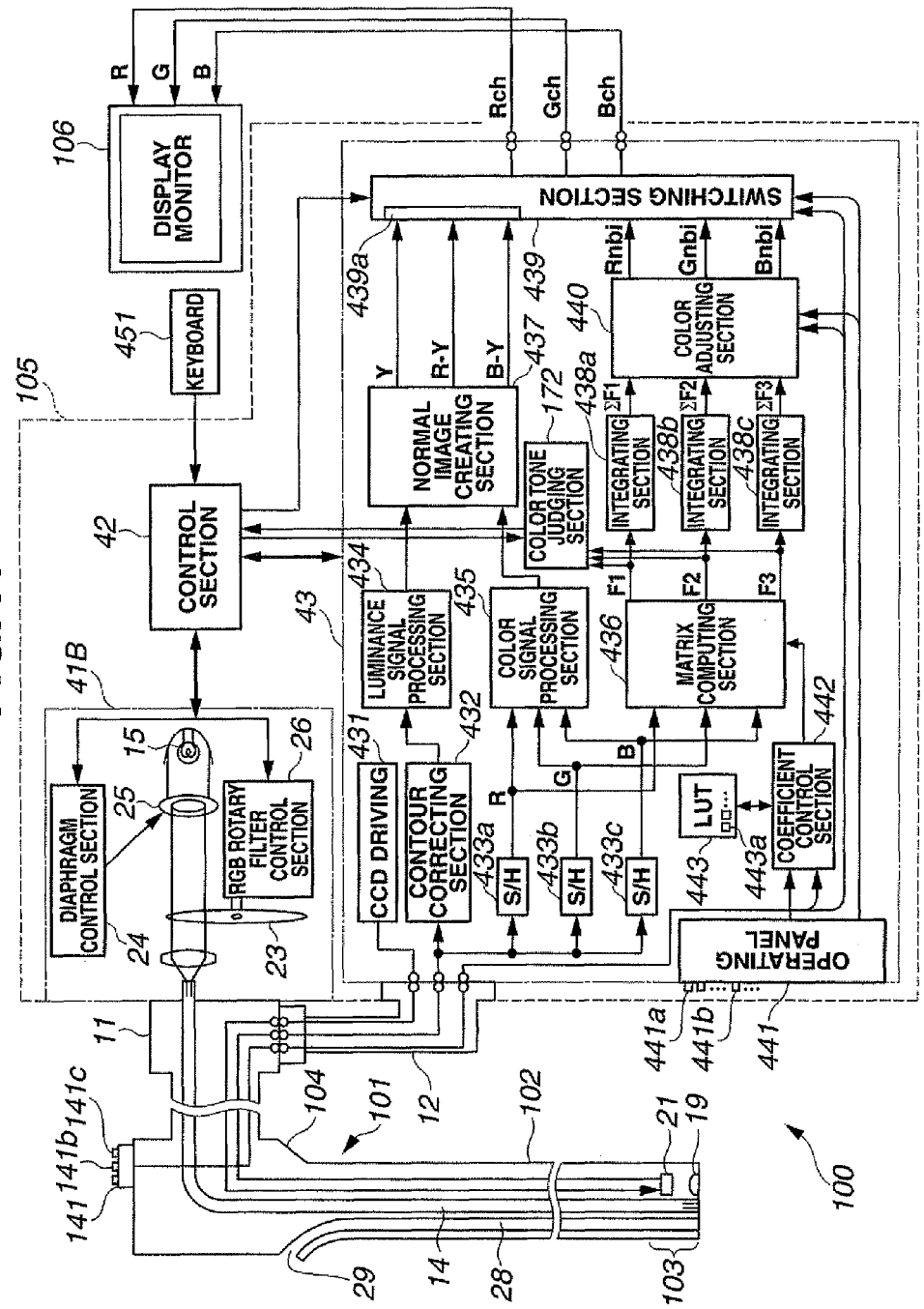
FIG. 41 is a block diagram showing a configuration of an electronic endoscope apparatus according to a fourth embodiment of the present invention.

Next, a fourth embodiment of the present invention will be described with reference to FIGS. 41 to 43. FIG. 41 shows a configuration of an electronic endoscope apparatus 100 according to the fourth embodiment of the present invention. The electronic endoscope apparatus 100 according to the present embodiment is configured as shown in FIG. 37, wherein a color tone judging section 172 that judges a color tone is provided in place of the brightness judging section 171.

Additionally, in the present embodiment, a frame sequential type light source section 41B is provided instead of the simultaneous type light source section 41 used in the first embodiment or the like.

With the light source section 41B, a diaphragm 25 is provided on a front face of the lamp 15, and an RGB filter 23 is further provided on a front face of the diaphragm 25. In addition, the diaphragm 25 is connected to a diaphragm control section 24. In response to a control signal from the diaphragm control section 24, the light source section 41B limits a light flux to be transmitted among light flux irradiated from the lamp 15 to change light quantity. Furthermore, the RGB rotary filter 23 is connected to an RGB rotary filter control section 26 and is rotated at a predetermined rotation speed.

As for operations by the light source section 41B according to the present embodiment, a light flux outputted from the lamp 15 is limited to a predetermined light quantity by the diaphragm 25. The light flux transmitted through the diaphragm 25 passes through the RGB filter, and is outputted as respective illumination lights of R/G/B or, in other words, as R/G/B frame sequential illumination lights at predetermined time intervals from the light source section 41B. In addition, the R/G/B frame sequential illumination lights are irradiated inside a subject to be examined via the light guide 14, whereby reflected light thereof is received by the CCD 21.

The CCD 21 in this case is a monochromatic CCD 21 that is not provided with a color filter. Signals (image pickup signals) obtained at the CCD 21 are sorted according to irradiation time by a switching section (not shown) provided at the endoscope apparatus main body 105 to be respectively inputted to the S/H circuits 433a to 433c.

In other words, when an R illumination light is irradiated via the R filter from the light source section 41, a signal obtained by the CCD 21 is inputted to the S/H circuit 433*a*. Incidentally, in a case where a CCD 21 provided with a color filter is employed, a simultaneous type light source section 41 such as that shown in FIG. 37 can be employed.

Figure 42:
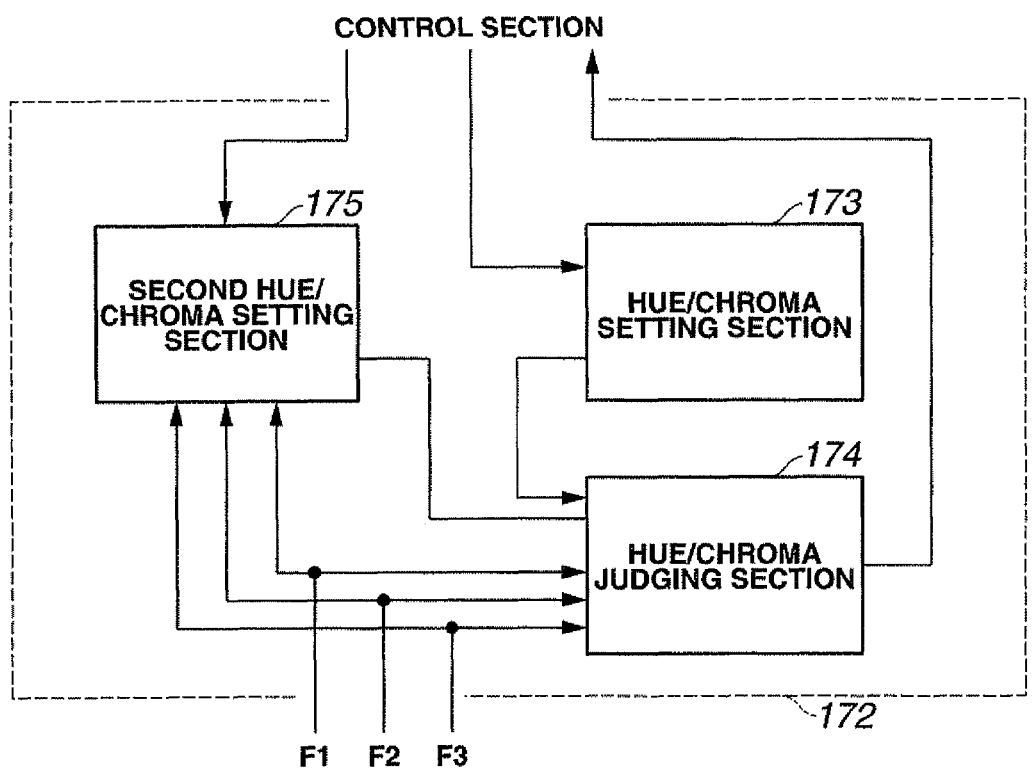
FIG. 42 is a block diagram showing a configuration example of a color tone judging section shown in FIG. 41.

In addition, as shown in FIG. 42, the above-mentioned color tone judging section 172 comprises: a (first) hue/chroma setting section 173 that sets a color tone range corresponding to a color tone to be detected; and a hue/chroma judging section 174 that judges whether the condition of the color tone range set by the hue/chroma setting section 173 is met.

In this case, the color tone range by the hue/chroma setting section 173 is inputted via the control section 42 from the keyboard 451 or the like, and can be set by the user or the like. Furthermore, spectral image signals F1, F2 and F3 from the matrix computing section 436 are inputted to the hue/chroma judging section 174. Then, the hue/chroma judging section 174 judges whether the signals fall within the color tone range set by the hue/chroma setting section 173, and outputs a judgment result thereof to the control section 42.

Based on the judgment result, the control section 42 performs control such as switching of the switching section 439.

For example, when a color tone of a current spectral image signal inputted to the color tone judging section 172 is detected within a color tone range judged by the hue/chroma judging section 174 in the color tone judging section 172 for a predetermined area or more in a single frame, the hue/chroma judging section 174 outputs a judgment signal to the effect that the color tone range has been met to the control section 42.

In response thereto, the control section 42 forcibly switches the operation mode to normal image observation mode, and also switches the switching section 439 to perform control so that a color image signal corresponding to the normal image is outputted to the display monitor 5.

Furthermore, in the present embodiment, a second hue/chroma setting section 175 is provided at the color tone judging section 172. Color tones to be detected via the control section 42 from the keyboard 451 or the like are registered into the second hue/chroma setting section 175.

In addition, registration/setting of a color tone range corresponding to a color tone to be detected from actually loaded spectral image signal data is also enabled.

In other words, when typical spectral image signal data to be detected exists, based on an load instruction from the keyboard 451 or the like, the image data is loaded to the second hue/chroma setting section 175 via the control section 42. In this case, it is also possible to process the data as required and set a color tone range in order to detect a similar color tone. The user can cause color tone judgment to be performed in a color tone range to be prioritized at the (first) hue/chroma setting section 173 or the second hue/chroma setting section 175.

In this manner, the second hue/chroma setting section 175 is arranged so that various color tones can be registered therein.

Operations in the case of the present modification will now be described. In the present modification, instead of performing judgment on whether a brightness detected in step S24 in FIG. 39 equals or falls below the threshold Vth, judgment is performed on whether a color tone detected by the color tone judging section 172 is detected within a predetermined color tone range for a predetermined area or more in a single frame.

Then, when it is determined that the color tone is detected in the predetermined color tone range for a certain value or more, the control section 42 performs control for forcibly switching from spectral image observation mode to normal observation mode. Other operations are the same as the operations described with reference to FIG. 39.

According to the present embodiment, when a predetermined color tone is attained for which the normal image observation mode is more desirable than the spectral image observation mode, forced setting to normal image observation mode can be performed. For example, with a spectral signal color image in the case of colonoscopy, when so-called residue such as food debris or feces remain, such residue is displayed in red resembling the color of bleeding. This is due to the fact that residue strongly absorbs blue light and strongly reflects green light. Normally, feces and the like are cleansed as a preparation prior to colonoscopy.

However, depending on the state of large intestines, there are cases where residue is not completely cleansed or where a considerable amount of residue remains.

In such cases, retaining a spectral color image may make it difficult to secure a visual field in a state suitable for examination, in which case it is desirable to forcibly recall the normal image observation mode in which familiar normal images are displayed.

For the present embodiment, in such a case, color tone detecting means such as described above or, more specifically, for example, means for detecting hue and chroma is provided within the signal processing control means. Accordingly, when it is determined that residue occupies a certain area of the screen or more, control is performed to restore (or switch) the observation mode switching means to normal observation mode.

Incidentally, as a modification of the present embodiment, a plurality of color tones or objects to be detected may be set at the above-described second hue/chroma setting section 175, and when one of the color tones or objects is detected during spectral image observation mode, the control section 42 may be arranged to perform control for restoring normal observation mode. In addition to residue described above, forcible restoration of the normal image observation mode is desirable in a case where there is a large amount of bile and mucosa of the biological tissue cannot be suitably observed as a spectral image or in a case where, due to pigment dispersing, the color tone of the pigment has a significant influence over the spectral image.

Figure 43:
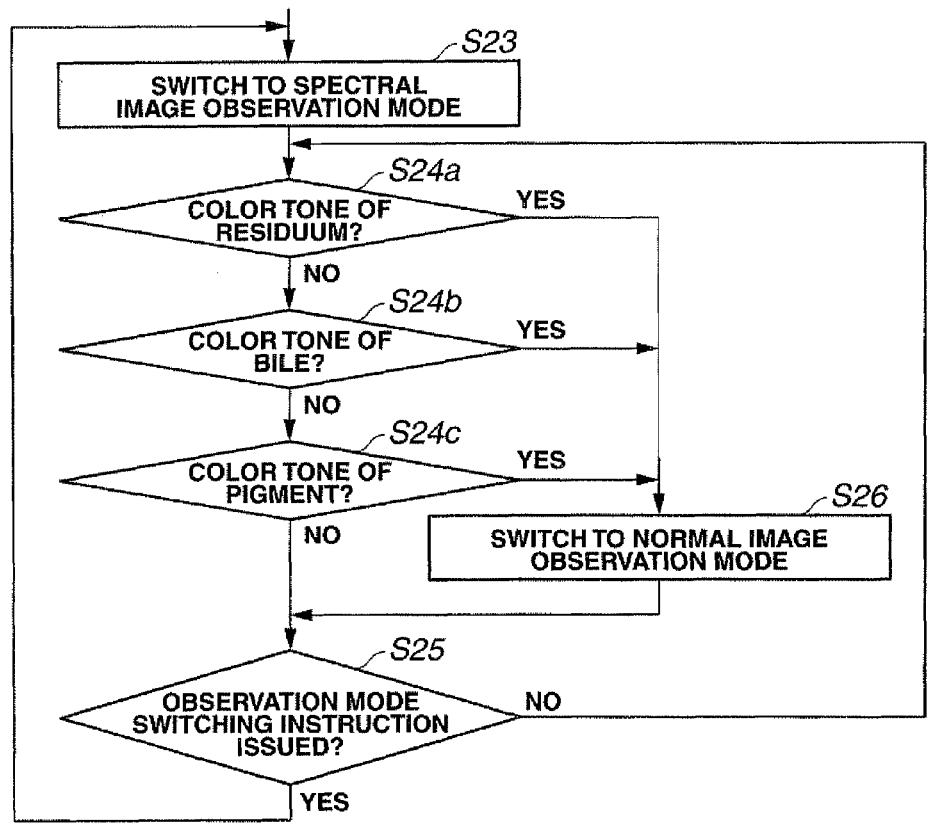
FIG. 43 is a flowchart showing a portion of operations in a modification of the fourth embodiment.

A portion of operations in this case is shown in FIG. 43. FIG. 43 represents processing in which the judgment processing portion of step S24 in FIG. 39 has been changed.

Incidentally, before commencing the operation, through an instruction operation from the keyboard 451 or the like, the user registers color tone data on colored pigments due to, for example, residue, bile, and typical pigment dispersing as color tones to be detected to the second hue/chroma setting section 175.

It is assumed that the user has selected a setting mode that restores normal observation mode when a predetermined amount or more of color tones due to the any of residue, bile and pigment is detected. After switching to spectral image observation mode is made in the same manner as in step S23 of FIG. 39, the color tone judging section 172 enters a state of monitoring whether a predetermined color tone is realized. In other words, as represented by step 24*a*, judgment is performed on whether the color tone of the current spectral image is the color tone of residue. When it is judged that a certain area or more is occupied by the color tone of residue, as represented by step S26, the control section 42 forcibly switches to normal image observation mode.

In addition, when the color tone of the current spectral image is not the color tone of residue, the routine proceeds to step S24*b* to judge whether a certain area or more is occupied by the color tone of bile. When it is judged that a certain area or more is occupied by the color tone of bile, as represented by step S26, the control section 42 forcibly switches to normal image observation mode.

Furthermore, when the color tone of the current spectral image is not the color tone of bile, the routine proceeds to step S24c to judge whether the color tone is that colored by pigments. When it is judged that a certain area or more is occupied by color tone colored by pigment, as represented by step S26, the control section 42 forcibly switches to normal image observation mode.

Moreover, when the color tone of the current spectral image is not color tone colored by pigments, the routine proceeds to step S25 at which the control section 42 enters an observation mode switching instruction waiting state.

According to the present modification, a forcible switch to normal image observation mode can be made when a color tone is developed which is unsuitable for continual observation in spectral image observation mode, thereby saving the user the trouble of performing switching. Therefore, according to the present modification, operability is improved.

In addition, in the embodiment described above, illumination light quantity (light quantity from a light source) is controlled/adjusted in order to avoid saturation of R/G/B color signals. Conversely, there is a method that adjusts (utilizes) an electronic shutter of a CCD.

With a CCD, charges accumulate in proportion to light intensity incident in a given time period, whereby the charge quantity is taken as a signal. A component corresponding to a charge accumulation time during which charge is accumulated is called an electronic shutter. By adjusting the charge accumulation time due to the electronic shutter, the accumulated quantity of charges or, in other words, a signal quantity can be adjusted. In other words, as shown in FIG. 44, by obtaining R/G/B color images in a state where charge accumulation time is sequentially changed, a spectral image similar to that in the case of illumination light quantity control can be obtained.

Figure 44:
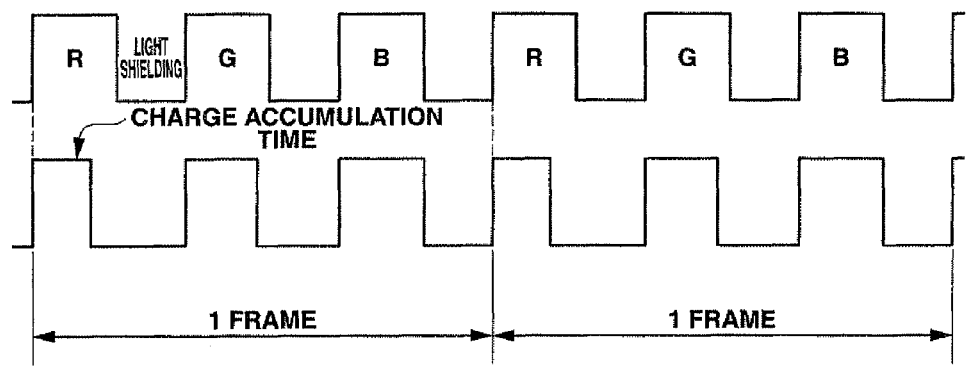
FIG. 44 is an explanatory diagram showing charge accumulation time by an electronic shutter of a CCD.

Incidentally, a case of frame sequential illumination is shown in FIG. 44. In this case, an upper side represents R, G and B illumination states while a lower row represents charge accumulation time due to an electronic shutter.

In other words, illumination light quantity control is used to obtain a normal image, and when obtaining a spectral image, it is possible to prevent saturation of R/G/B color images by varying charge accumulation time due to an electronic shutter.

Incidentally, an electronic shutter may also be applied to a case of a simultaneous type.

In addition, a modification of the present modification may be arranged as described below.

The modification utilizes a frame sequential method in a manner similar to the fourth embodiment, and takes advantage of features thereof. By adding weighting to charge accumulation times due to electronic shutter control, the modification is able to simplify creation of spectral image data. In other words, in the present modification, a CCD driving circuit 431 capable of varying the charge accumulation time of the CCD 21 is provided.

Figure 45:
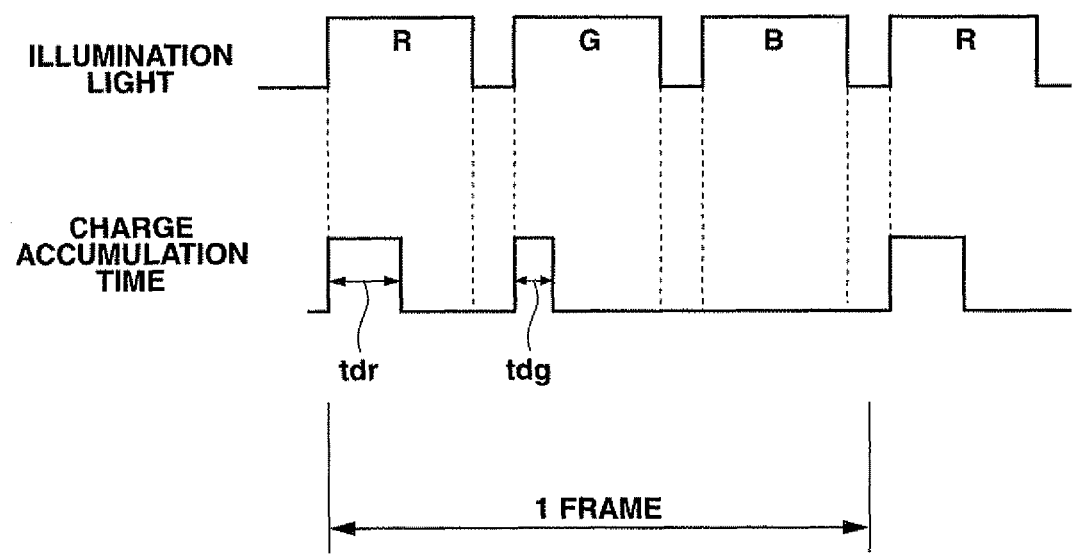
FIG. 45 is an explanatory diagram showing charge accumulation time by an electronic shutter of a CCD in greater detail.

As for operations of the present modification, as shown in FIG. 45, when respective illumination lights are irradiated via the RGB rotary filter 23, the charge accumulation time due to the electronic shutter of the CCD 21 is varied. At this point, let us assume that the respective charge accumulation times of the CCD 21 for R/G/B illumination lights are tdr, tdg and tdb (incidentally, since an accumulation time is not provided for the B color image signal, tdb is omitted in the diagram).

For example, when performing the matrix computation represented by Formula 21, since the computation to be performed by the F3 quasi-filter image may be determined from RGB images obtained by a normal endoscope as $$F3 = -0.050R - 1.777G + 0.829B \quad (25)$$

setting the charge accumulation time due to electronic shutter control according to RGB shown in FIG. 45 to $$tdr:tdg:tdb = 0.050:1.777:0.829 \quad (26)$$

shall suffice. In addition, for the matrix portion, a signal in which only the R and G components are inverted as well as the B component are added. As a result, a spectral image similar to that in the third embodiment can be obtained.

According to the present modification, in the same manner as the fourth embodiment, a spectral image on which vascular patterns are clearly displayed can be obtained. Furthermore, the present embodiment utilizes the frame sequential method for creating color image signals in the same manner as the fourth embodiment, and charge accumulation times can be varied using the electronic shutter for each color image signal. Consequently, the matrix computing section 436 need only perform addition and subtraction processing, thereby enabling simplification of processing.

Fifth Embodiment

Figure 46:
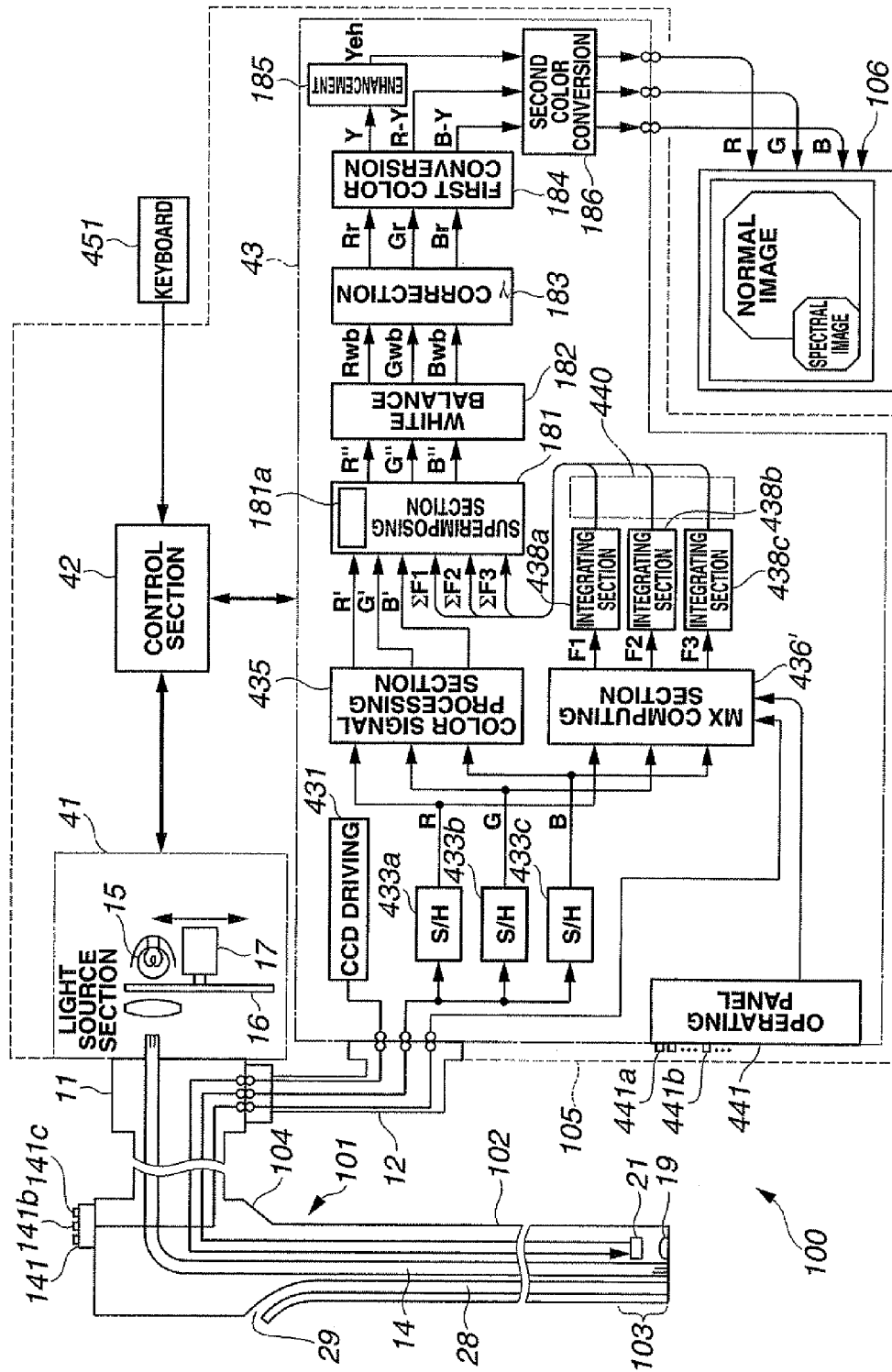
FIG. 46 is a block diagram showing a configuration of an electronic endoscope apparatus according to a fifth embodiment of the present invention.

Next, a fifth embodiment of the present invention will be described with reference to FIGS. 46 to 48. FIG. 46 shows an electronic endoscope apparatus 100 according to the fifth embodiment of the present invention. The electronic endoscope apparatus 100 according to the present embodiment is, for example, the electronic endoscope apparatus 100 shown in FIG. 4 configured so that a normal observation image and a spectral image are simultaneously displayable on, for example, the display monitor 106 by changing a portion of the configuration of the main body processing apparatus 43. As will be described hereafter, display state control means or display control means is provided which not only switches among images to display one of the images but also displays both images by, for example, changing sizes thereof.

As shown in FIG. 46, color signals R', G' and B' outputted from, for example, the color signal processing section 435 are inputted to a superimposing section 181. The color signals R', G' and B' are superimposed by the superimposing section 181 with output signals ΣF1 to ΣF3 of the integrating sections 438a to 438c. The superimposed signals are denoted by R", G" and B". The signals R", G" and B" are inputted to a white balance circuit 182, and outputted therefrom as white balance-adjusted signals Rwb, Gwb and Bwb.

Incidentally, in FIG. 46, while output signals ΣF1 to ΣF3 of the integrating sections 438a to 438c are arranged to be inputted to the superimposing section 181 as indicated by the solid lines, the signals may alternatively be passed through the color adjusting section 440 to be made into color-adjusted signals and then inputted to the superimposing section 181 as indicated by the dashed-two dotted lines.

The signals Rwb, Gwb and Bwb are inputted to a γ correcting circuit 183 to become γ corrected signals Rγ, Gγ and Bγ, and then inputted to a first color converting circuit 184 to be converted into a luminance signal Y and color difference signals R-Y and B-Y.

The luminance signal Y is made into a contour-enhanced luminance signal Yeh by an enhancing circuit 185, and then inputted together with the color difference signals R-Y and B-Y to a second color converting circuit 186 to be color-converted to create color signals R, G and B.

The color signals R, G and B are inputted to the respective channels R, G and B of the display monitor 106, whereby a corresponding image is displayed thereon.

For example, the superimposing section 181 according to the present embodiment includes a built-in selecting circuit that selects and outputs only one of the signals and a built-in enlarging/reducing circuit 181a that performs enlargement/reduction. Accordingly, in response to a display control signal by the user from the keyboard 451 or the like, the control circuit 42 causes only one of the signals to be outputted from the superimposing section 181. Consequently, the selected image is displayed on the display monitor 106.

In addition, in response to the display control signal, the superimposing section 181 performs adjustment for enlarging/reducing the image sizes of the color signals R', G' and B' outputted from the color signal processing section 435 or the output signals ΣF1 to ΣF3 of the integrating sections 438a to 438c, and superimposes both images and outputs the result thereof. As shown, in the present embodiment display state control means or display control means is formed which controls images or the like displayed on the display monitor 106.

For example, the display monitor 106 of FIG. 46 shows an example in which both a normal image from the side of the color signals R', G' and B' outputted from the color signal processing section 435 and a spectral image from the side of the output signals ΣF1 to ΣF3 of the integrating sections 438a to 438c are simultaneously displayed, where the normal image is displayed in its original size while the spectral image is displayed in a state adjusted to a smaller size.

Furthermore, as shown in FIGS. 47 and 48, the present embodiment is arranged so that identification for confirmation is explicitly displayed in the vicinity of an image actually being displayed on the display monitor 106 so that confirmation of whether the image is a normal image or a spectral image can be made. In other words, observation mode displaying means is provided which, when displaying an image corresponding to each observation mode, displays the observation mode or an image type in the vicinity of the image corresponding to the observation mode. Incidentally, the functions of the coefficient control section 442 and the LUT 443 shown in FIG. 4 are incorporated into a matrix computing section (in FIG. 46, abbreviated to MX computing section) 436' according to the present embodiment.

Other components are similar to those shown in, for example, FIG. 4. While a case where switching of observation modes causes one of the observation modes to be alternatively selected has been described with reference to FIG. 32, the present embodiment can also accommodate a case where two observation modes are simultaneously selected and images obtained by the two observation modes are simultaneously displayed.

FIG. 47 shows an image display example displayed on the display monitor 106 by selection control of observation modes or display methods performed by the user.

FIGS. 47A and 47B respectively show cases where only a normal image or only a spectral image is displayed on the display monitor 106. In these cases, the same display modes as, for example, FIGS. 32A and 32B are employed.

In addition, FIG. 47C shows a case where a normal image is displayed in a large size and a spectral image is displayed in a small size, whereby both images are superimposed and then displayed. In other words, an example displaying a picture-in-picture which displays the normal image as a parent image and the spectral image as a child image is shown.

FIG. 47D shows a case where the sizes of the normal image and the spectral image in FIG. 47C are alternated.

As seen, by allowing a normal image and a spectral image to be displayed simultaneously, the present embodiment offers a wider range of options to the user and therefore improves operability.

In addition, since the present embodiment is arranged so that, even when only one of the images is displayed, the image can be enlarged and displayed according to the resolution or the like of the display monitor 106, images may be displayed in appropriate sizes even when the resolution or the like of the display screen of the display monitor 106 varies. Furthermore, an observation mode of an image or a type of the image is displayed, for example, below each image to enable easy confirmation by the user. In this example, a case of a normal image is explicitly indicated by "NI" and a case of a spectral image by "NBI".

While a case of a normal display monitor 106 has been described with reference to FIG. 47, display may be performed instead on, for example, a display monitor having a landscape-oriented display screen.

FIG. 48A depicts a situation where a normal image and a spectral image are simultaneously displayed on a display monitor 106 having a landscape-oriented display screen. Again, by adjusting display sizes, it is possible to perform display at relatively large sizes as shown in FIG. 48A.

In addition, as shown in FIG. 48B, two display monitors 106A and 106B may be prepared to respectively display a normal image and a spectral image. Furthermore, the display may also be alternated.

Moreover, the spectral image to be displayed may be selected from those having a single wavelength or, as was the case in the second embodiment or the like, a quasi-color display may be performed instead using two or three spectral images.

In addition, while an example arranged for easy confirmation even when images of two observation modes are both displayed has been described as an observation mode display example according to the present embodiment, the arrangements shown in FIGS. 32D to 32F may be employed when only displaying an image of one of the observation modes.

Incidentally, a configuration in the case of simultaneously displaying a normal image and a spectral image is not limited to that of FIG. 46. For example, with respect to the configuration shown in FIG. 4, approximately the same effects and advantages can be achieved by employing the superimposing section 181 shown in FIG. 46 which performs selection of one of the images and synthesis (superposition) of both images in place of the switching section 439 that selects one of the images.

Sixth Embodiment

Figures 49, 50:
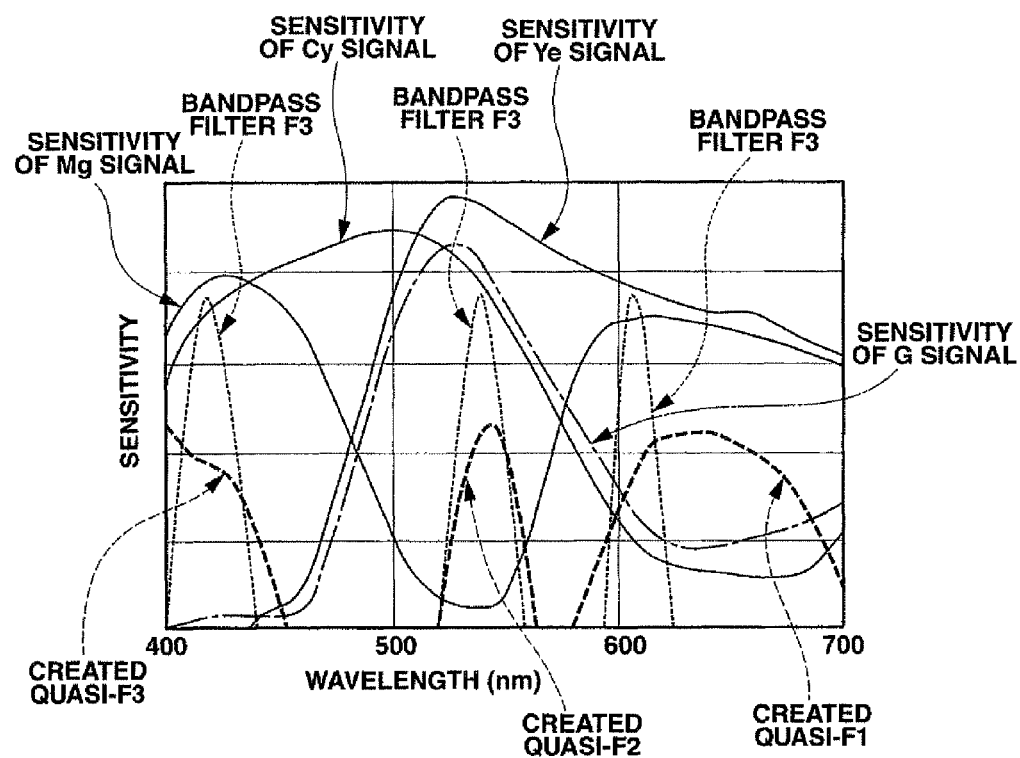
FIG. 49 is a diagram showing an array of color filters according to a sixth embodiment of the present invention.
FIG. 50 is a diagram showing spectral sensitivity characteristics of the color filters shown in FIG. 49.

FIGS. 49 and 50 relate to a sixth embodiment of the present invention, where FIG. 49 is a diagram showing a color filter array and FIG. 50 is a diagram showing spectral sensitivity characteristics of the color filters shown in FIG. 49.

Since the sixth embodiment is almost the same as the first embodiment, only differences therebetween will be described. Like components will be assigned like reference characters and descriptions thereof will be omitted.

The present embodiment primarily differs from the first embodiment in the color filters provided at the CCD 21. Compared to the first embodiment in which RGB primary color-type color filters are used as shown in FIG. 6, the present embodiment uses complementary type color filters.

As shown in FIG. 49, the array of the complementary type color filters is constituted by the respective elements of G, Mg, Ye and Cy. Incidentally, the respective elements of the primary color-type color filters and the respective elements of the complementary type color filters form relationships of Mg=R+B, Cy=G+B, and Ye=R+G.

In this case, a full pixel readout from the CCD 21 and signal processing or image processing on the images from the respective color filters will be performed. In addition, by transforming Formulas 1 to 8 and 19 to 21 which accommodate primary color-type color filters so as to accommodate complementary type color filters, Formulas 27 to 33 presented below are derived. Note that target narrow bandpass filter characteristics are the same.

$$(G \ Mg \ Cy \ Ye) \begin{pmatrix} a_1 & a_2 & a_3 \\ b_1 & b_2 & b_3 \\ c_1 & c_2 & c_3 \\ d_1 & d_2 & d_3 \end{pmatrix} = (F_1 \ F_2 \ F_3) \quad (27)$$

$$C = (G \ Mg \ Cy \ Ye) \quad (28)$$

$$A = \begin{pmatrix} a_1 & a_2 & a_3 \\ b_1 & b_2 & b_3 \\ c_1 & c_2 & c_3 \\ d_1 & d_2 & d_3 \end{pmatrix}$$

$$F = (F_1 \ F_2 \ F_3)$$

$$k_G = (\int S(\lambda) \times H(\lambda) \times G(\lambda) d\lambda)^{-1}$$

$$k_{Mg} = (\int S(\lambda) \times H(\lambda) \times Mg(\lambda) d\lambda)^{-1}$$

$$k_{Cy} = (\int S(\lambda) \times H(\lambda) \times Cy(\lambda) d\lambda)^{-1}$$

$$k_{Ye} = (\int S(\lambda) \times H(\lambda) \times Ye(\lambda) d\lambda)^{-1} \quad (29)$$

$$K = \begin{pmatrix} k_G & 0 & 0 & 0 \\ 0 & k_{Mg} & 0 & 0 \\ 0 & 0 & k_{Cy} & 0 \\ 0 & 0 & 0 & k_{Ye} \end{pmatrix} \quad (30)$$

$$A = \begin{pmatrix} -0.413 & -0.678 & 4.385 \\ -0.040 & -3.590 & 2.085 \\ -0.011 & -2.504 & -1.802 \\ 0.332 & 3.233 & -3.310 \end{pmatrix} \quad (31)$$

$$K = \begin{pmatrix} 1 & 0 & 0 & 0 \\ 0 & 0.814 & 0 & 0 \\ 0 & 0 & 0.730 & 0 \\ 0 & 0 & 0 & 0.598 \end{pmatrix} \quad (32)$$

$$A' = KA \quad (33)$$

$$= \begin{pmatrix} 1 & 0 & 0 & 0 \\ 0 & 0.814 & 0 & 0 \\ 0 & 0 & 0.730 & 0 \\ 0 & 0 & 0 & 0.598 \end{pmatrix} \begin{pmatrix} -0.413 & -0.678 & 4.385 \\ -0.040 & -3.590 & 2.085 \\ -0.011 & -2.504 & -1.802 \\ 0.332 & 3.233 & -3.310 \end{pmatrix}$$

$$= \begin{pmatrix} -0.413 & -0.678 & 4.385 \\ -0.033 & -2.922 & 1.697 \\ -0.008 & -1.828 & -1.315 \\ 0.109 & 1.933 & -1.979 \end{pmatrix}$$

Furthermore, FIG. 50 shows spectral sensitivity characteristics when using complementary type color filters, target bandpass filters, and characteristics of quasi-bandpass filter determined from Formulas 27 to 33 provided above.

It is needless to say that, when using complementary type color filters, the S/H circuits shown in FIG. 4 are respectively applied to G/Mg/Cy/Ye instead of R/G/B.

Moreover, even when using complementary type color filters, the matrix estimation method expressed by Formulas 9 to 18 is applicable. In this case, when the number of complementary type color filters is 4, the portion of the hypothesis of Formula 14 that living body spectral reflectance can be approximated using three fundamental spectral characteristics now becomes four, or four or less. Therefore, accordingly, a dimension for computing the estimation matrix is changed from 3 to 4.

According to the present embodiment, in the same manner as the first embodiment, a spectral image on which vascular patterns are clearly displayed can be obtained. In addition, the present embodiment is able to receive the full benefit of using complementary type color filters.

Incidentally, with the present invention, various combinations and subsequent use of the embodiments described above are possible. In addition, various modifications may be made without departing from the scope thereof.

For example, for all previously described embodiments, the operator can create a new quasi-bandpass filter during clinical practice or at other timings and apply the filter to clinical use. In other words, with respect to the first embodiment, a designing section (not shown) capable of computing/calculating matrix coefficients may be provided at the control section 42 shown in FIG. 4.

Accordingly, a quasi-bandpass filter suitable for obtaining a spectral image desired by the operator may be arranged to be newly designed by inputting a condition via the keyboard 451 provided on the endoscope apparatus main body 105 shown in FIG. 4. In this case, immediate clinical application can be achieved by setting a final matrix coefficient (corresponding to the respective elements of matrix <A'> in Formulas 21 and 33) derived by applying a correction coefficient (corresponding to the respective elements of matrix <K> in Formulas 20 and 32) to the calculated matrix coefficient (corresponding to the respective elements of matrix <A> in Formulas 19 and 31) to the matrix computing section 436 shown in FIG. 4.

Moreover, for the respective embodiments and the like described above, while a case of creating a spectral image signal has been primarily described using a case where RGB signals, which are also referred to as color signals, are created as color image signals from an image pickup signal picked up by the CCD 21, a spectral image signal may alternatively be created from a color image signal constituted by a luminance signal and a color difference signal.

The respective embodiments and the like described above have been described using an example in which a subject to be examined such as biological tissue or the like is illuminated by guiding illumination light from the light source section 31 by the light guide 14 of the endoscope 101 and irradiating the (guided) illumination light to the subject to be examined from a distal end face of the light guide 14.

The present invention is not limited to this example, and, for example, a light emitting diode (abbreviated to LED) may be arranged to be positioned on the distal end portion 103 of the endoscope 101, whereby the subject to be examined is illuminated by illumination light irradiated from the LED. In other words, the light source section or the illuminating section in this case is provided at the endoscope 101.

Seventh Embodiment

Figure 51:
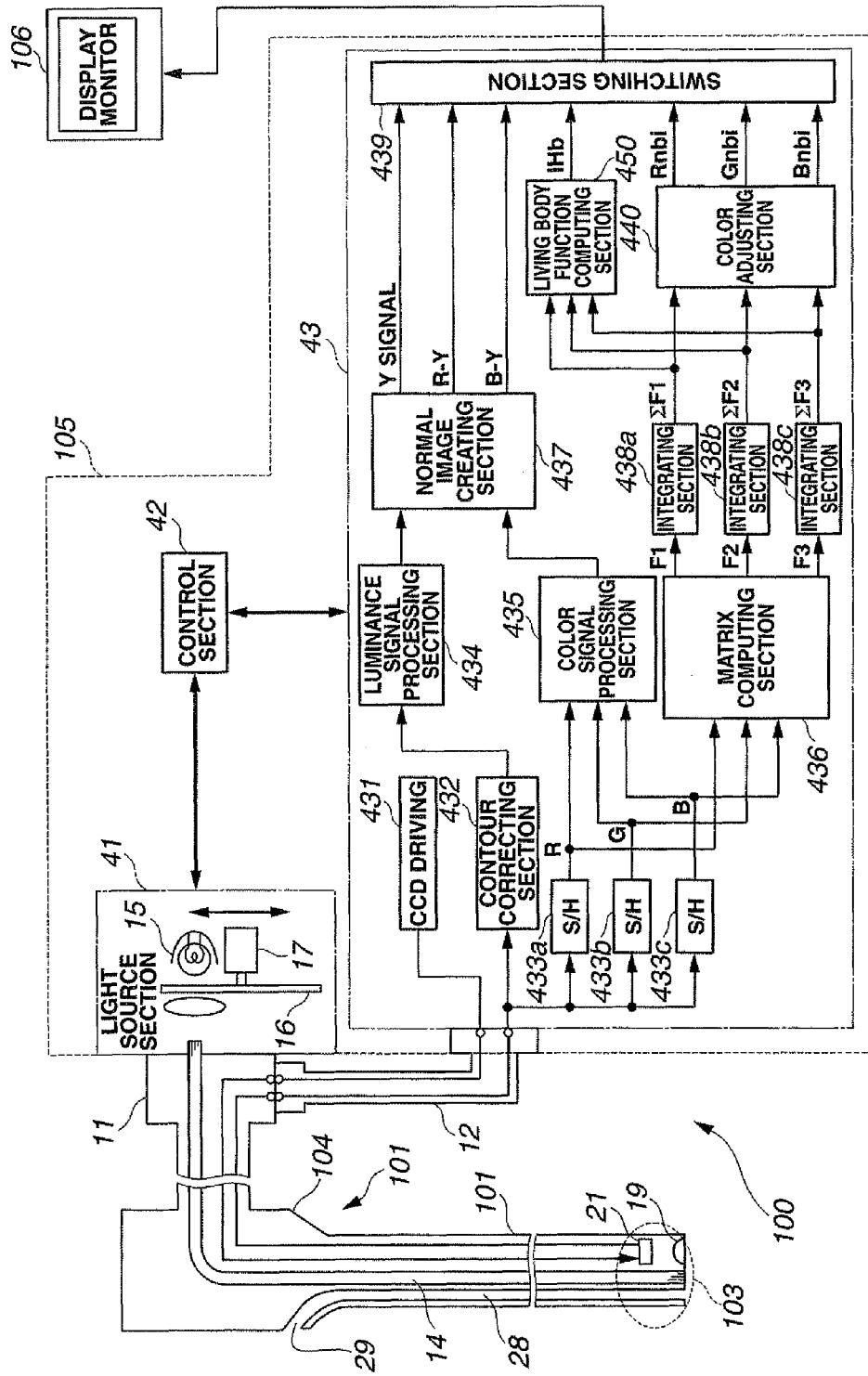
FIG. 51 is a block diagram showing a configuration of an electronic endoscope apparatus according to a seventh embodiment of the present invention.
Figure 52:
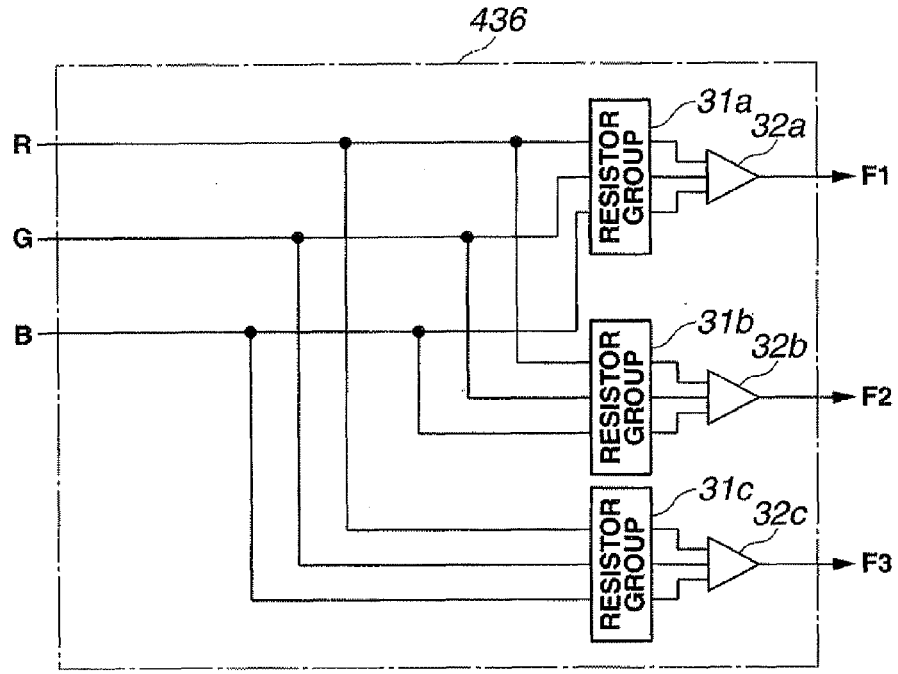
FIG. 52 is a configuration diagram showing a configuration of a matrix computing section shown in FIG. 51.
Figure 53:
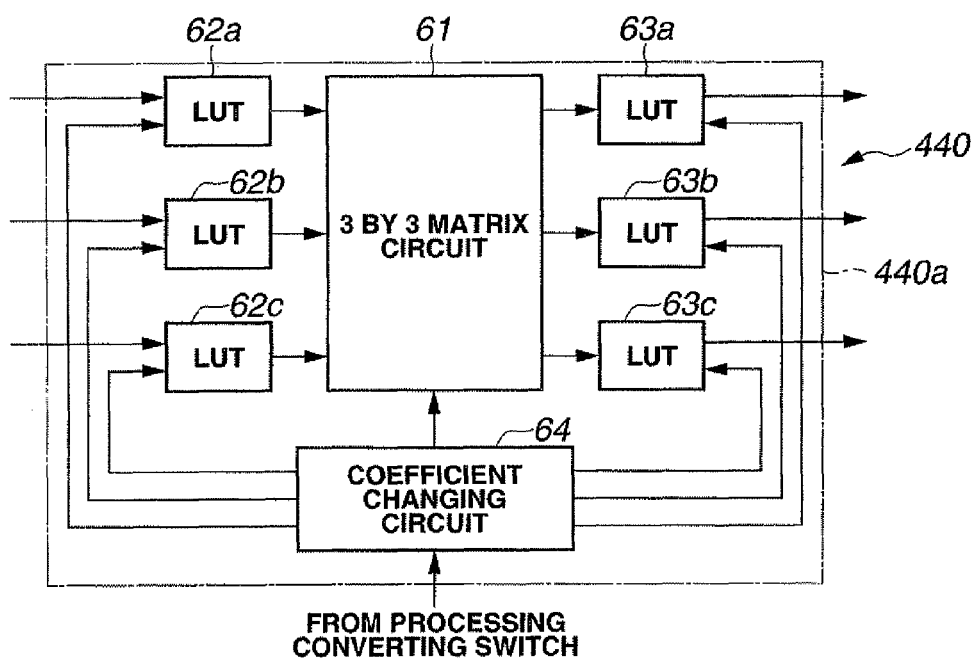
FIG. 53 is a block diagram showing a configuration of a color adjusting section shown in FIG. 51.
Figure 54:
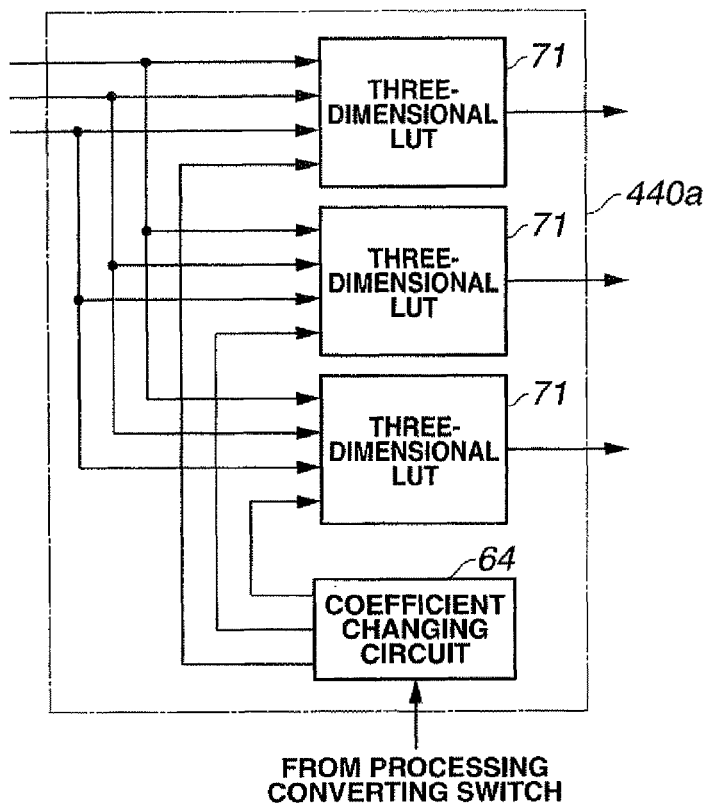
FIG. 54 is a block diagram showing a configuration of a modification of the color adjusting section shown in FIG. 51.
Figure 55:
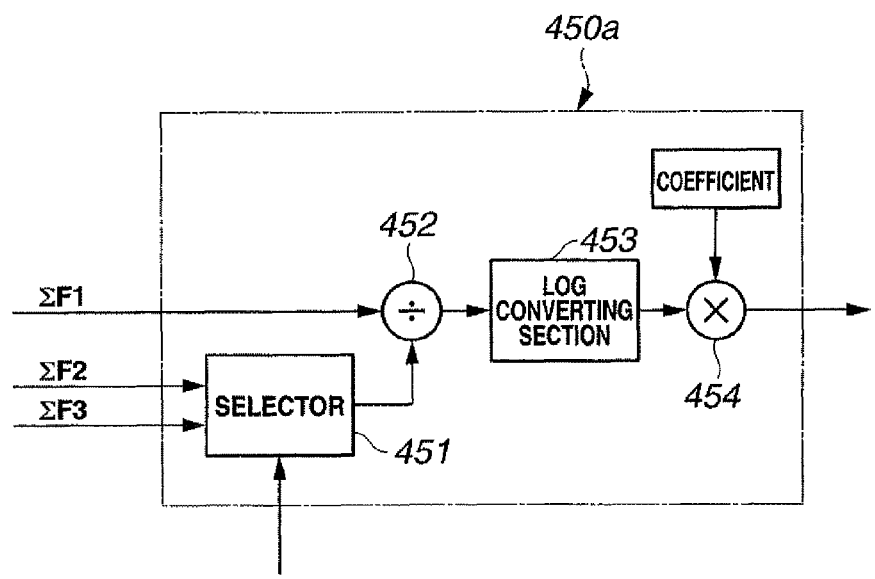
FIG. 55 is a block diagram showing a configuration of a living body function computing section shown in FIG. 51.
Figure 56:
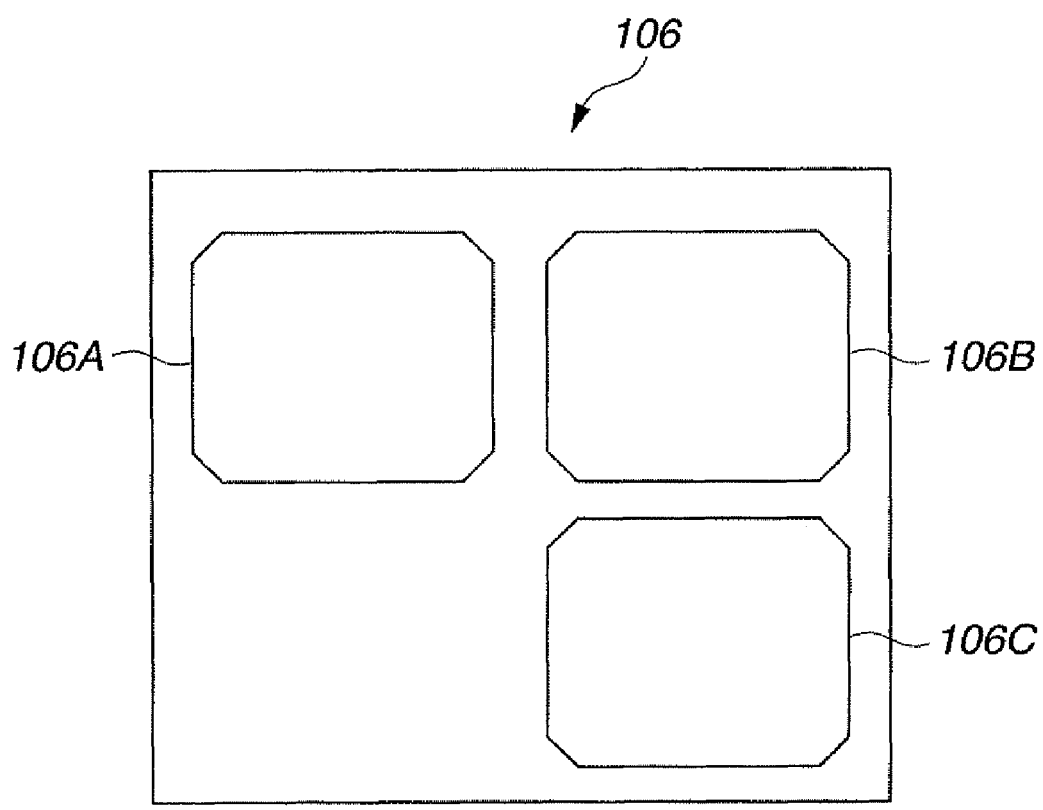
FIG. 56 is a diagram showing a display example on a monitor.

Next, a seventh embodiment of the present invention will be described with reference to FIGS. 1 to 3, FIG. 51, FIGS. 5 to 7, FIG. 52, FIGS. 9 to 20, FIG. 53, FIG. 22 and FIGS. 54 to 56. FIG. 51 is a block diagram showing a configuration of the electronic endoscope apparatus shown in FIG. 3; FIG. 52 is a configuration diagram showing a configuration of the matrix computing section shown in FIG. 51; FIG. 53 is a block diagram showing a configuration of the color adjusting section shown in FIG. 51; FIG. 54 is a block diagram showing a configuration of a modification of the color adjusting section shown in FIG. 51; FIG. 55 is a block diagram showing a configuration of a living body function computing section; and FIG. 56 is a diagram showing a display example on a monitor.

An object of the present embodiment is to provide a biological observation apparatus capable of displaying living body function information related to tissue information of a desired depth of biological tissue based on a spectral image obtained through signal processing, thereby contributing towards the improvement of diagnostic performance.

Since FIGS. 1 and 2, a matrix calculating method, a correcting method, an S/N improving method, and a modification of the matrix calculating method related to the present seventh embodiment have been described in the introduction of the first embodiment, descriptions thereof will be omitted.

Next, an exterior configuration of an electronic endoscope apparatus according to the seventh embodiment of the present invention is the same as that shown in, for example, FIG. 3.

As shown in FIG. 3, an electronic endoscope apparatus 100 comprises an electronic endoscope 101, an endoscope apparatus main body 105, and a display monitor 106. In addition, the endoscope 101 is primarily constituted by: an insertion portion 102 to be inserted into the body of a subject to be examined; a distal end portion 103 provided at an distal end of the insertion portion 102; and an angle operating section 104 provided on an opposite side of the distal end side of the insertion portion 102 and which is provided for instructing operations such as bending operations of the distal end portion 103.

An image of the subject to be examined acquired by the endoscope 101 is subjected to predetermined signal processing at the endoscope apparatus main body 105, and a processed image is displayed on the display monitor 106.

Next, the endoscope apparatus main body 105 will be described in detail with reference to FIG. 51. FIG. 51 is a block diagram of the synchronous electronic endoscope apparatus 100.

As shown in FIG. 51, the endoscope apparatus main body 105 comprises a light source section 41 that primarily acts as an illuminating section, a control section 42, and a main body processing apparatus 43. The control section 42 and the main body processing apparatus 43 control operations of the light source section 41 and/or a CCD 21 as an image pickup section, and constitute a signal processing control section that outputs an video signal to the display monitor 106 that is a display device.

The present embodiment is configured so that the operating panel 441, the coefficient control section 442, the LUT 443 and the keyboard 451 in the first embodiment shown in FIG. 4 are not provided, and instead, a living body function computing section 450 is provided. The living body function computing section 450 receives input of output signals from integrating sections 438a, 438b and 438c, creates information on indicators representing living body functions, and outputs the information to a switching section 439. The configuration of the endoscope apparatus main body 105 will now be described in greater detail.

Incidentally, for the present embodiment, while a description will be given on the assumption that the light source section 41 and the main body processing apparatus 43 that performs image processing and the like are provided within the endoscope apparatus main body 105 that is a single unit, the light source section 41 and the main body processing apparatus 43 may be alternatively configured as a connectable and detachable unit that is separate from the endoscope apparatus main body 105.

The light source section 41 is connected to the control section 42 and the endoscope 101, and irradiates a white light (including light that is not perfectly white) at a predetermined light quantity based on a signal from the control section 42. In addition, the light source section 41 comprises: a lamp 15 as a white light source; a chopper 16 for adjusting light quantity; and a chopper driving section 17 for driving the chopper 16.

The chopper 16 is configured as shown in FIG. 5, and since the configuration and operations thereof have already been described in the first embodiment, a description thereof will be omitted.

Incidentally, the light source section 41 may be arranged to adjust light quantity through current control of the lamp 15 instead of through light quantity control by the chopper. In other words, a current control device that performs current control of the lamp 15 is provided, whereby based on a command from the control section 42, the current control device controls current flowing through the lamp 15 so that neither of the color image signals of R, G and B reach a saturated state. Consequently, since current used by the lamp 15 for emission is controlled, the light quantity thereof varies according to the magnitude of the current.

As seen, even in the case of an electronic endoscope apparatus employing current control of the lamp 15, a spectral image that clearly displays a vascular pattern or the like can be obtained. The light quantity control method by current control of the lamp 15 is more advantageous than the light quantity control method using a chopper in that an easier control method is achieved.

In addition, the endoscope 101 connected to the light source section 41 via the connector 11 comprises: an objective lens 19 on the distal end portion 103; and a solid state image pickup device 21 such as a CCD or the like (hereinafter simply referred to as CCD). The CCD in the present embodiment is of the single-plate type (the CCD used in a synchronous electronic endoscope), and is of the primary color-type. FIG. 6 shows an array of color filters positioned on an image pickup plane of the CCD. In addition, FIG. 7 shows respective spectral sensitivity characteristics of RGB of the color filters shown in FIG. 6.

Furthermore, as shown in FIG. 51, the insertion portion 102 comprises: a light guide 14 that guides light irradiated from the light source section 41 to the distal end portion 103; a signal line for transferring an image of the subject to be examined obtained by the CCD to the main body processing apparatus 43; and a forceps channel 28 or the like for performing treatment. Incidentally, a forceps aperture 29 for inserting forceps into the forceps channel 28 is provided in the vicinity of an operating section 104.

Moreover, in the same manner as the light source section 41, the main body processing apparatus 43 is connected to the endoscope 101 via the connector 11. The main body processing apparatus 43 is provided with a CCD driving circuit 431 for driving the CCD 21. In addition, the main body processing apparatus 43 is provided with a luminance signal processing system and a color signal processing system as signal circuit systems for obtaining a normal image.

The luminance signal processing system comprises: a contour correcting section 432 connected to the CCD 21 and which performs contour correction; and a luminance signal processing section 434 that creates a luminance signal from data corrected by the contour correcting section 432. In addition, the color signal processing system comprises: sample-and-hold circuits (S/H circuits) 433a to 433c, connected to the CCD 21, which perform sampling and the like on a signal obtained by the CCD 21 and create an RGB signal; and a color signal processing section 435 connected to outputs of the S/H circuits 433a to 433c and which creates color signals.

Furthermore, a normal image creating section 437 that creates a single normal image from outputs of the luminance signal processing system and the color signal processing system is provided, whereby a Y signal, an R-Y signal and a B-Y signal are sent from the normal image creating section 437 to the display monitor 106 via the switching section 439.

On the other hand, a matrix computing section 436 that receives input of output signals (RGB signals) of the S/H circuits 433a to 433c and performs predetermined matrix computation on the RGB signals is provided as a signal circuit system for obtaining spectral images. Matrix computation refers to addition processing of color image signals and to processing of multiplying the matrix obtained by the above-described matrix calculating method (or modification thereof).

In the present embodiment, while a method using electronic circuit processing (processing by hardware using an electronic circuit) will be described as the matrix calculating method, a method using numerical data processing (processing by software using a program) such as in an embodiment described later may be used instead. In addition, upon execution, a combination of the methods may also be used.

FIG. 52 is a circuit diagram of the matrix computing section 436. RGB signals are respectively inputted to amplifiers 32a to 32c via resistor groups 31a to 31c.

The respective resistor groups have a plurality of resistors to which RGB signals are respectively connected, and the resistance values of the respective resistors are values corresponding to the matrix coefficient. In other words, the gain of the RGB signals are varied by the respective resistors and added (or subtracted) by the amplifiers.

The respective outputs of the amplifiers 32a to 32c become outputs of the matrix computing section 436. In other words, the matrix computing section 436 performs so-called weighting addition processing. Incidentally, the resistance values of the respective resistors used herein may be arranged to be variable.

The outputs of the matrix computing section 436 are respectively inputted to the integrating sections 438a to 438c, and after integrating computation is performed thereon, respective spectral image signals $\Sigma F1$ to $\Sigma F3$ are sent to the color adjusting section 440 and the living body function computing section 450.

The color adjusting section 440 performs computation for color adjustment, to be described later, on the spectral image signals $\Sigma F1$ to $\Sigma F3$, respectively creates spectral channel image signals Rnbi, Gnbi and Bch as color tone-adjusted spectral image signals, and outputs the signal to the switching section 439. In the present embodiment, although R, G and B channels of the display monitor 106 are not explicitly shown in FIG. 51, the spectral channel image signals Rnbi, Gnbi and Bch are respectively outputted to the R, G and B channels of the display monitor 106. Therefore, as a description focusing on display colors on the display monitor 106, the spectral channel image signals Rnbi, Gnbi and Bch may be described as color channel image signals outputted to the R, G and B channels of the display monitor 106.

Furthermore, based on the spectral image signals $\Sigma F1$ to $\Sigma F3$, the living body function computing section 450 according to the present embodiment calculates an indicator representing a living body function or, more specifically, a value that correlates with the concentration of hemoglobin having a blood oxygen metabolic function in a living body (hemoglobin index: IHb) through computation as living body function information. In addition, the living body function computing section 450 creates a living body function image (included in living body function information) such as a quasi-image (a quasi-color image or a grayscale image) from the calculated IHb value, and sends the image to the switching section 439. Configurations of the color adjusting section 440 and the living body function computing section 450 shall be described later.

Incidentally, the switching section 439 is provided to perform display switching among a normal image, a spectral image and a living body function image on the display monitor 106, and is also capable of switching/displaying among spectral images. In other words, the operator is able to make a selection from a normal image, spectral channel image signals Rnbi, Gnbi and Bnbi, and a living body function image and have the image displayed. Furthermore, the switching section 439 may also be configured so that any two or more images are simultaneously displayable on the display monitor 106.

In particular, in the case where a normal image, a spectral channel image and a living body function image are simultaneously displayable on the display monitor 106, the user is able to readily compare a spectral channel image and a living body function image against a generally observed normal image. Moreover, the user is able to perform observation of normal images and spectral channel images while taking into consideration the respective features thereof (a feature of normal images is that the color tones thereof closely resemble that of naked eye observation for easy observation; a feature of spectral channel images is that observation of predetermined blood vessels or the like which cannot be observed through normal images are possible). Therefore, the present embodiment is extremely useful in diagnostics.

Next, a detailed description on operations of the electronic endoscope apparatus 100 according to the present embodiment will be given with reference to FIG. 51.

In the following, operations during normal image observation will be described first, followed by a description on operations during spectral image observation.

First, to describe operations of the light source section 41, based on a control signal from the control section 42, the chopper driving section 17 is set to a predetermined position and rotates the chopper 16. A light flux from the lamp 15 passes through a notched portion of the chopper 16, and is collected by a collecting lens at an incident end of the light guide 14 that is a light fiber bundle provided inside the connector 11 located at a connecting portion of the endoscope 101 and the light source section 41.

The collected light flux passes the light guide 14 and is irradiated into the body of a subject to be examined from an illuminating optical system provided at the distal end portion 103. The irradiated light flux is reflected inside the subject to be examined, and signals are collected via the objective lens 19 by the CCD 21 according to each color filter shown in FIG. 6.

The collected signals are inputted in parallel to the luminance signal processing system and the color signal processing system described above. Signals collected according to color filter are added on a per-pixel basis and inputted to the contour correcting section 432 of the luminance signal system, and after contour correction, inputted to the luminance signal processing section 434. A luminance signal is created at the luminance signal processing section 434, whereby the created luminance signal is inputted to the normal image creating section 437.

Meanwhile, signals collected by the CCD 21 is inputted on a per-filter basis to the S/H circuits 433a to 433c, and R/G/B signals are respectively created. In addition, after the R/G/B signals are subjected to color signal processing at the color signal processing section 435, a Y signal, an R-Y signal and a B-Y signal are created at the normal image creating section 437 from the afore-mentioned luminance signals and color signals. The Y signal, the R-Y signal and the B-Y signal are outputted to the display monitor 106 via the switching section 439, and a normal image of the subject to be examined is displayed on the display monitor 106.

Next, operations during spectral image observation will be described. Incidentally, descriptions on operations similar to those performed during normal image observation shall be omitted.

The operator issues an instruction for observing a spectral image from a normal image by operating a keyboard provided on the main body 105, a switch provided on the operating section 104 of the endoscope 101, or the like. At this point, the control section 42 changes the control state of the light source section 41 and the main body processing apparatus 43.

More specifically, as required, the control section 42 changes the light quantity irradiated from the light source section 41. As described above, since saturation of an output from the CCD 21 is undesirable, during spectral image observation, the control section 42 reduces illumination light quantity in comparison to normal image observation. Furthermore, in addition to performing control so that an output signal from the CCD does not reach saturation, the control section 42 is also able to change illumination light quantity within a range in which saturation is not reached.

In addition, as for changing control over the main body processing apparatus 43 by the control section 42, a signal outputted from the switching section 439 is switched from an output of the normal image creating section 437 to an output of the color adjusting section 440.

In addition, the outputs of the S/H circuits 433a to 433c are subjected to amplification/addition processing at the matrix computing section 436, outputted according to each band to the integrating sections 438a to 438c, and after integration processing, outputted to the color adjusting section 440. Even when illumination light quantity is reduced by the chopper 16, storage and integration by the integrating sections 438a to 438c enable signal intensity to be increased as shown in FIG. 2, and a spectral image with improved S/N can be obtained.

A specific description will now be given on matrix processing performed by the matrix computing section 436 according to the present embodiment. In the present embodiment, when attempting to create bandpass filters (hereinafter referred to as a quasi-bandpass filters) closely resembling ideal narrowband pass filters F1 to F3 (in this case, the respective wavelength transmitting ranges are assumed to be F1: 590 nm to 620 nm, F2: 520 nm to 560 nm, and F3: 400 nm to 440 nm) depicted in FIG. 7 from the spectral sensitivity characteristics of the RGB color filters indicated by the solid lines in FIG. 7, according to the contents represented by Formulas 1 to 5 presented above, the following matrix becomes optimum.

$$A = \begin{pmatrix} 0.625 & -3.907 & -0.05 \\ -3.097 & 0.631 & -1.661 \\ 0.036 & -5.146 & 0.528 \end{pmatrix} \quad (19)$$

Furthermore, by performing correction using contents represented by Formulas 6 and 7, the following coefficient is obtained.

$$K = \begin{pmatrix} 1 & 0 & 0 \\ 0 & 1.07 & 0 \\ 0 & 0 & 1.57 \end{pmatrix} \quad (20)$$

Incidentally, the above uses a priori information that the spectrum $S(\lambda)$ of a light source represented by Formula 6 is depicted in FIG. 9 and the reflectance spectrum $H(\lambda)$ of the living body to be studied represented by Formula 7 is depicted in FIG. 10.

Therefore, the processing performed by the matrix computing section 436 is mathematically equivalent to the matrix computation below.

$$\begin{aligned} A' &= KA \quad (21) \\ &= \begin{pmatrix} 1 & 0 & 0 \\ 0 & 1.07 & 0 \\ 0 & 0 & 1.57 \end{pmatrix} \begin{pmatrix} 0.625 & -3.907 & -0.05 \\ -3.097 & 0.631 & -1.661 \\ 0.036 & -5.146 & 0.528 \end{pmatrix} \\ &= \begin{pmatrix} 0.625 & -3.907 & -0.050 \\ -3.314 & 0.675 & -1.777 \\ 0.057 & -8.079 & 0.829 \end{pmatrix} \end{aligned}$$

By performing the matrix computation, quasi-filter characteristics (indicated as characteristics of quasi-filters F1 to F3 in FIG. 7) are obtained. In other words, the aforementioned matrix processing is for creating a spectral image signal by using a quasi-bandpass filter (matrix) created in advance as described above on a color image signal.

An example of an endoscopic image created using the quasi-filter characteristics will be described below.

As shown in FIG. 11, tissue inside a body cavity 51 often has an absorbing body distributed structure such as blood vessels which differ in a depth direction. Capillaries 52 are predominantly distributed in the vicinity of the surface layers of the mucous membrane, while veins 53 larger than capillaries are distributed together with capillaries in intermediate layers that are deeper than the surface layers, and even larger veins 54 are distributed in further deeper layers.

On the other hand, the reachable depth of light in the depth-wise direction of the tissue inside a body cavity 51 is dependent on the wavelength of the light. As shown in FIG. 12, in the case of a light having a short wavelength such as blue (B), illumination light including the visible range only reaches the vicinity of the surface layers due to absorption characteristics and scattering characteristics of the biological tissue. Thus, the light is subjected to absorption and scattering within a range up to that depth, and light exiting the surface is observed. Furthermore, in the case of green (G) light whose wavelength is longer than that of blue (B) light, light reaches a greater depth than the reachable range of blue (B) light. Thus, light is subjected to absorption and scattering within the range, and light exiting the surface is observed. Moreover, red (R) light whose wavelength is longer than that of green (G) light reaches an even greater depth.

Figure 14:
FIG. 14 is a first diagram showing respective band images by the white light of FIG. 13.

As shown in FIG. 13, with RGB light during normal observation of the tissue inside a body cavity 51, since the respective wavelength band overlap each other:

(1) an image pickup signal picked up by the CCD 21 under B band light picks up a band image having superficial and intermediate tissue information including a large amount of superficial tissue information such as that shown in FIG. 14;
(2) an image pickup signal picked up by the CCD 21 under G band light picks up a band image having superficial and intermediate tissue information including a large amount of intermediate tissue information such as that shown in FIG. 15; and
(3) an image pickup signal picked up by the CCD 21 under R band light picks up a band image having intermediate and deep tissue information including a large amount of deep tissue information such as that shown in FIG. 16.

In addition, by performing signal processing on the RGB image pickup signals at the endoscope apparatus main body 105, it is now possible to obtain a desirable endoscopic image or an endoscopic image with natural color reproduction.

The matrix processing performed by the above-described matrix computing section 436 is for creating a spectral image signal using a quasi-bandpass filter (matrix) created in advance as described above on a color image signal.

For example, spectral image signals F1 to F3 are obtained by using quasi-bandpass filters F1 to F3 having discrete narrowband spectral characteristics and which are capable of extracting desired deep tissue information, as shown in FIG. 17. As shown in FIG. 17, since the respective wavelength ranges of the quasi-bandpass filters F1 to F3 do not overlap each other, (4) a band image having superficial layer tissue information such as that shown in FIG. 18 is picked up in the spectral image signal F3 by the quasi-bandpass filter F3;
(5) a band image having intermediate layer tissue information such as that shown in FIG. 19 is picked up in the spectral image signal F2 by the quasi-bandpass filter F2; and
(6) a band image having deep layer tissue information such as that shown in FIG. 20 is picked up in the spectral image signal F1 by the quasi-bandpass filter F1.

Next, with respect to the spectral image signals ΣF1 to ΣF3 obtained as described above, as an example of a most simplified color conversion, the color adjusting section 440 respectively allocates the spectral image signal F1 to the spectral channel image signal Rnbi (to be outputted to the R channel of the display monitor 106), the spectral image signal F2 to the spectral channel image signal Gnbi (to be outputted to the G channel of the display monitor 106), and the spectral image signal F3 to the spectral channel image signal Bnbi (to be outputted to the B channel of the display monitor 106), and outputs the same to the display monitor 106 via the switching section 439.

As shown in FIG. 53, the color adjusting section 440 is constituted by a color conversion processing circuit 440a comprising: a 3 by 3 matrix circuit 61; three sets of LUTs 62a, 62b, 62c, 63a, 63b and 63c provided anteriorly and posteriorly to the 3 by 3 matrix circuit 61; and a coefficient changing circuit 64 that changes table data of the LUTs 62a, 62b, 62c, 63a, 63b and 63c or the coefficient of the 3 by 3 matrix circuit 61.

The spectral image signals F1 to F3 inputted to the color conversion processing circuit 440a are subjected to inverse 7 correction, non-linear contrast conversion and the like on a per-band data basis by the LUTs 62a, 62b and 62c.

Then, after color conversion is performed at the 3 by 3 matrix circuit 61, γ correction or appropriate tone conversion processing is performed at the post-stage LUTs 63a, 63b and 63c.

Table data of the LUTs 62a, 62b, 62c, 63a, 63b and 63c or the matrix coefficient of the 3 by 3 matrix circuit 61 can be changed by the coefficient changing circuit 64.

Changes by the coefficient changing circuit 64 are performed based on a control signal from a processing converting switch (not shown) provided on the operating section of the endoscope 101 or the like.

Upon receiving the control signal, the coefficient changing circuit 64 reads out appropriate data from coefficient data stored in advance in the color adjusting section 440, and overwrites the current circuit coefficient with the data.

Next, specific contents of color conversion processing will be described. Formula 22 represents an example of a color conversion equation.

$$\begin{pmatrix} R_{nbi} \\ G_{nbi} \\ B_{nbi} \end{pmatrix} = \begin{pmatrix} 1 & 0 & 0 \\ 0 & 1 & 0 \\ 0 & 0 & 1 \end{pmatrix} \begin{pmatrix} F_1 \\ F_2 \\ F_3 \end{pmatrix} \quad (22)$$

The processing represented by Formula 22 is color conversion in which spectral image signals F1 to F3 are assigned to the spectral channel image signals Rnbi, Gnbi and Bnbi, which are respectively outputted to the R channel, the G channel and the B channel of the display monitor 106, in ascending order of wavelengths.

In this manner, when observing spectral channel images corresponding to the spectral channel image signals Rnbi, Gnbi and Bnbi by color images, for example, the image shown in FIG. 22 is obtained. The spectral image signal F3 is reflected on a large vein existing at a deep position, and the display color thereof is depicted as a blue pattern. Since the spectral image signal F2 is strongly reflected on a vascular network near intermediate layers, a display color (color image) thereof is displayed as a red pattern. Among vascular networks, those existing near the surface of the mucosal membrane are expressed as a yellow pattern.

While the color conversion processing circuit 440a is arranged to perform color conversion by a matrix computing unit constituted by the 3 by 3 matrix circuit 61, the present invention is not limited to this arrangement. Instead, color conversion processing means may be configured using a numerical processor (CPU) or an LUT.

For example, in the above-described embodiment, while the color conversion processing circuit 440a is illustrated by a configuration centered around the 3 by 3 matrix circuit 61, similar advantages may be achieved by replacing the color conversion processing circuit 440a with three-dimensional LUTs 71 corresponding to each band as shown FIG. 54. In this case, the coefficient changing circuit 64 performs an operation for changing the table contents based on a control signal from a processing converting switch (not shown) provided on the operating section of the endoscope 101 or the like.

On the other hand, with respect to a spectral channel image that is an observation image, when the operator issues a computation instruction to the living body function computing section 450 by operating a keyboard provided on the main body 105, a switch provided on the operating section 104 of the endoscope 101, or the like, an IHb value is computed by an IHb value calculating circuit 450a shown in FIG. 55 using band image information on two spectral image signals among the spectral image signals F1 to F3.

Conventional IHb value computation uses Formula 34, which takes advantage of the fact that a G band image strongly reflects blood information.

Meanwhile, by narrowing the band of the filter, surface capillaries are strongly reflected on the B image. Therefore, the depths at which blood exists differ between the B and G images with B reflecting superficial information and G reflecting information of deeper locations.

$$IHb = 32 \times \log_2(R/G) \quad (34)$$

Consequently, the living body function computing section 450 treats the spectral image signal F1 corresponding to the R band as an R signal, the spectral image signal F2 corresponding to the G band as a G signal, and the spectral image signal F3 corresponding to the B band as a B signal. Then, by switching operations of a selector 451 provided in the IHb value calculating circuit 450a based on an instruction from an operating switch or the like, the living body function computing section 450 switches and computes an IHb value of mucosal intermediate layers based on G information using Formula 34 and an IHb value of mucosal surface layers based on B information using Formula 35.

Accordingly, the user is able to separate and confirm tissue information of a desired depth in the vicinity of the tissue surface of biological tissue.

$$IHb = 32 \times \log_2(R/B) \quad (35)$$

Specifically, as shown in FIG. 55, the IHb value calculating circuit 450a comprises the selector 451, a divider 452, a logarithmic converting section 453 and a multiplier 454. The spectral image signal F1 as an R signal, and either the spectral image signal F2 as a G signal or the spectral image signal F3 as a B signal selected by the selector 451 are inputted to the divider 452, whereby either R/G or R/B is calculated by the divider 452.

The output of the divider 452 is inputted to the log converting section 453, whereby logarithmic conversion is performed by the log converting section 453 using a conversion table on the ROM or the like. The logarithmically-converted signal is subjected to multiplication with a predetermined coefficient at the multiplier 454, and, as a result, per-pixel 11b values are calculated.

Subsequently, a quasi-color image or the like is created based on the computed per-pixel IHb values, and the quasi-color image or the like is outputted to the display monitor 106 via the switching section 439. For example, as shown in FIG. 56, a normal color image 106A is displayed on a left hand side of the screen on the display monitor 106, an observation image 106B from a spectral channel image is displayed on a right hand side thereof, and a living body function image 106C based on the IHb values is displayed under the observation image 106B.

As seen, a normal image, an observation image color-converted to a color tone suitable for observing tissue information of a desired depth, and a living body function image based on IHb values of a tissue corresponding to the observation image are simultaneously displayed on the display monitor 106. Moreover, according to the present embodiment, the diagnostic performance of the operator can be enhanced.

For example, through the color conversion processing represented by Formula 22, the spectral image signal F2 is allocated to a spectral channel image signal Gnbi (the G channel of the display monitor 106), a vascular network near intermediate layers is displayed by a red pattern observation image, and, at the same time, IHb values of mucosal intermediate layers based on G information in the spectral image signals F1 and F2 are calculated to display a living body function image. From the display, the operator is now able to readily grasp changes in hemodynamics due to hemoglobin distribution.

At this point, while vascular networks existing near the surface of the mucosal membrane are expressed as a yellow pattern in an observation image, a yellow pattern tends to have a weak contrast against background mucosa and therefore low visibility. Changes in the pattern in the vicinity of the surface of the mucosal membrane are particularly important for the discovery and differential diagnosis of early-stage diseases.

In this light, in order to reproduce patterns in the vicinity of the surface of the mucosal membrane with higher visibility in an observation image, it is effective to perform the conversion expressed by Formula 23 provided below, and at the same time calculate an IHb value of the mucosa surface layer based on B information from the spectral image signals F1 and F3 to display a living body function image.

$$\begin{pmatrix} R_{nbi} \\ G_{nbi} \\ B_{nbi} \end{pmatrix} = \begin{pmatrix} 1 & 0 & 0 \\ 0 & \omega_G & \omega_B \\ 0 & 0 & 1 \end{pmatrix} \begin{pmatrix} F_1 \\ F_2 \\ F_3 \end{pmatrix} \quad (23)$$

The processing represented by Formula 23 is an example of a conversion in which the spectral image signal F1 is mixed with the spectral image signal F2 at a certain ratio and created data is newly used as the spectral channel signal Gnbi, and enables further clarification of the fact that absorbing/scattering bodies such as a vascular network differ according to depth position.

Therefore, by adjusting the matrix coefficient via the coefficient changing circuit 64, the user is able to adjust display colors. As for operations, in conjunction with a mode switching switch (not shown) provided at the operating section of the endoscope 101, the matrix coefficient is set to a default value from a through operation in the image processing means.

A through operation in this case refers to a state in which a unit matrix is mounted on the 3 by 3 matrix circuit 61 and a non-conversion table is mounted on the LUTs 62a, 62b, 62c, 63a, 63b and 63c. This means that, for example, preset values of $\omega_G = 0.2$, $\omega_B = 0.8$ are to be provided as default values of the matrix coefficient.

Then, by operating the operating section of the endoscope 101 or the like, the user performs adjustment so that the coefficient becomes, for example, $\omega_G = 0.4$, $\omega_B = 0.6$. An inverse γ correction table and a γ correction table are applied as required to the LUTs 62a, 62b, 62c, 63a, 63b and 63c.

Incidentally, in addition to the IHb value calculating circuit 450a, the living body function computing section 450 may be provided with a computing section that computes feature values such as an IHb average over an entire image, an IHb standard deviation, and an IHb kurtosis, whereby the values may be displayed on the screen of the display monitor 106 together with a living body function image based on the IHb value.

As seen, according to the present embodiment, by creating a quasi-narrowband filter using a color image signal for creating a normal electronic endoscopic image (normal image), a spectral image having desired deep portion tissue information such as a vascular pattern can be obtained without having to use an optical narrow bandpass filter for spectral images.

In addition, according to the present embodiment, by setting a parameter of a color conversion processing circuit 440a of the color adjusting section 440 according to the spectral image, it is now possible to realize a representation method that makes full use of a feature that is reachable depth information during narrowband spectral image information, and as a result effective separation and visual confirmation of tissue information of a desired depth in the vicinity of the surface of biological tissue can be realized.

Furthermore, according to the present embodiment, by simultaneously displaying an observation image having a color tone suitable for observation and living body function information based on an IHb value such as a quasi-image in addition to a normal color image on the same display monitor, it is now possible to readily grasp, for example, a congestive state. Therefore, the present embodiment enables respective images to be readily compared without having to frequently switch among various images, as was conventionally required, and improvements in diagnostic performance may be advantageously achieved.

Eighth Embodiment

Figure 57:
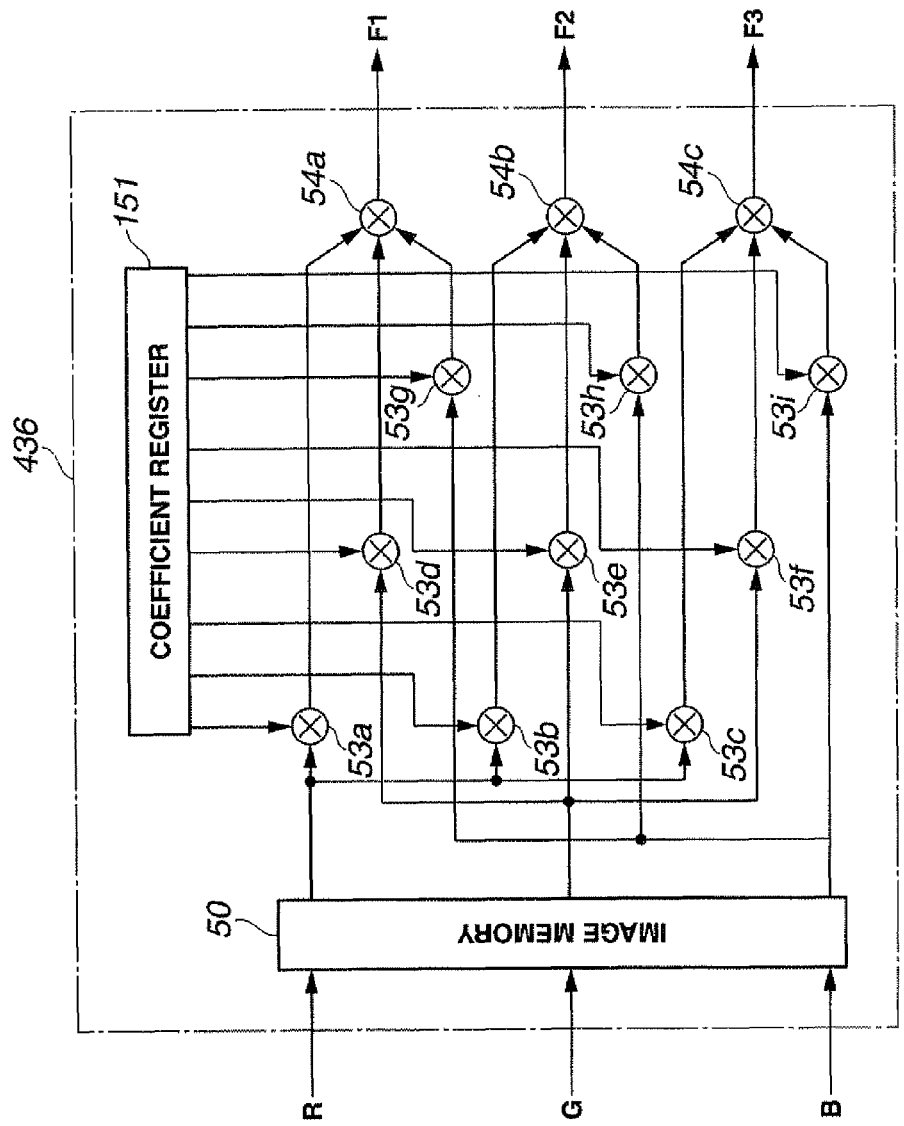
FIG. 57 is a block diagram showing a configuration of a matrix computing section according to an eighth embodiment of the present invention.

FIG. 57 is a block diagram showing a configuration of a matrix computing section according to an eighth embodiment of the present invention. Since the eighth embodiment is almost the same as the seventh embodiment, only differences therebetween will be described. Like components will be assigned like reference characters and descriptions thereof will be omitted.

The present embodiment primarily differs from the seventh embodiment in the matrix computing section 436. While the seventh embodiment is arranged so that matrix computation is performed by so-called hardware processing using an electronic circuit, in the present embodiment, the matrix computation is performed by numerical data processing (processing by software using a program).

A specific configuration of the matrix computing section 436 according to the present embodiment is shown in FIG. 57. The present matrix computing section 436 includes an image memory 50 for storing respective color image signals of R, G and B. In addition, a coefficient register 151 in which respective values of the matrix <A'> expressed by Formula 21 are stored as numerical data is provided.

The coefficient register 151 and the image memory 50 are connected to multipliers 53a to 53i; the multipliers 53a, 53d and 53g are connected to a multiplier 54a; and the output of the multiplier 54a is connected to the integrating section 438a shown in FIG. 51. In addition, the multipliers 53b, 53e and 53h are connected to a multiplier 54b, and the output thereof is connected to the integrating section 438b. Furthermore, the multipliers 53c, 53f and 53i are connected to a multiplier 54c, and the output thereof is connected to the integrating section 438c.

As for operations in the present embodiment, inputted RGB image data is temporarily stored in the image memory 50. Next, a computing program stored in a predetermined storage device (not shown) causes each coefficient of the matrix <A'> from the coefficient register 151 to be multiplied at a multiplier with RGB image data stored in the image memory 50.

Incidentally, FIG. 57 shows an example in which the R signal is multiplied by each matrix coefficient at the multipliers 53a to 53c. In addition, as is shown in the same diagram, the G signal is multiplied by each matrix coefficient at the multipliers 53d to 53f, while the B signal is multiplied by each matrix coefficient at the multipliers 53g to 53i. As for data respectively multiplied by a matrix coefficient, outputs of the multipliers 53a, 53d and 53g are multiplied by the multiplier 54a, outputs of the multipliers 53b, 53e and 53h are multiplied by the multiplier 54b, and the outputs of the multipliers 53c, 53f and 53i are multiplied by the multiplier 54c.

An output of the multiplier 54a is sent to the integrating section 438a. In addition, the outputs of the multipliers 54b and 54c are respectively sent to the integrating sections 438b and 438c.

According to the present embodiment, in the same manner as in the seventh embodiment, a spectral observation image capable of clearly displaying a vascular pattern can be obtained, and at the same time, living body function information related to the spectral observation image can be displayed.

Moreover, in the present embodiment, since matrix processing is performed using software without using hardware as is the case with the seventh embodiment, for example, changes to each matrix coefficient or the like can be accommodated in a prompt manner.

In addition, in a case where matrix coefficients are stored by resultant values alone or, in other words, not stored as a matrix <A'> but stored according to $S(\lambda)$, $H(\lambda)$, $R(\lambda)$, $G(\lambda)$ and $B(\lambda)$, and computed as required to determine a matrix <A'> to be used, a change can be made to only one of the elements, thereby improving convenience. For example, it is possible to change only the illumination light spectral characteristics. $S(\lambda)$ or the like.

Ninth Embodiment

Figure 58:
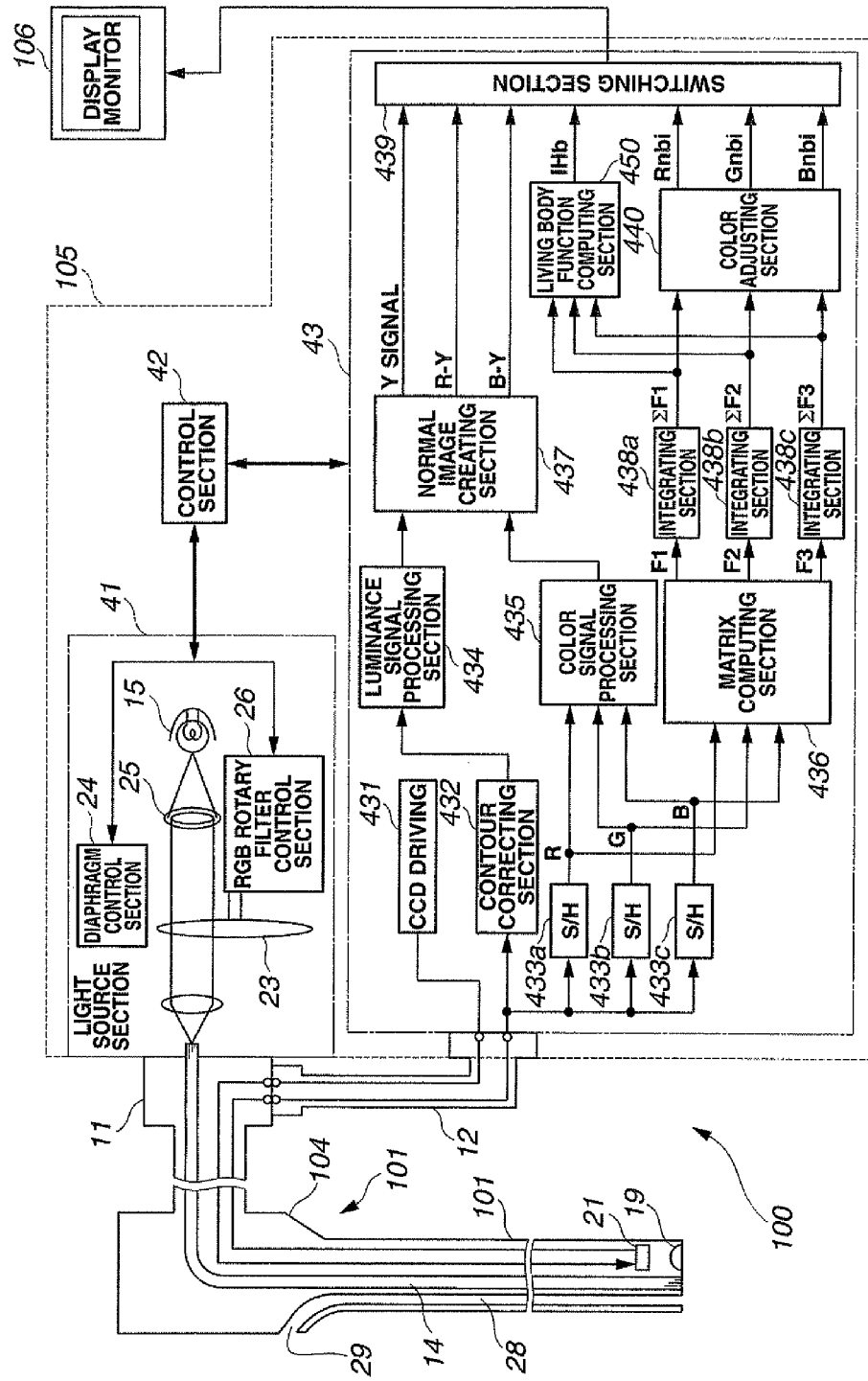
FIG. 58 is a block diagram showing a configuration of an electronic endoscope apparatus according to a ninth embodiment of the present invention.

FIGS. 58 and 59 relate to a ninth embodiment of the present invention, where FIG. 58 is a block diagram showing a configuration of an electronic endoscope apparatus, and FIG. 59 is a diagram showing charge accumulation times of the CCD 21 shown in FIG. 58.

Since the ninth embodiment is configured almost the same as the seventh embodiment, only differences therebetween will be described. Like components will be assigned like reference characters and descriptions thereof will be omitted.

The present embodiment differs from the seventh embodiment in the light source section 41 and the CCD 21. In the seventh embodiment, the CCD 21 is provided with the color filters shown in FIG. 6 and is a so-called synchronous-type CCD that creates a color pickup image using the color filters. However, in the present embodiment, a so-called frame sequential-type CCD 21 that creates a color pickup image by illuminating illumination light in the order of R, G and B is used.

As shown in FIG. 58, the light source section 41 according to the present embodiment is provided with a diaphragm 25 on a front face of the lamp 15, and an RGB filter 23 is further provided on a front face of the diaphragm 25. In addition, the diaphragm 25 is connected to a diaphragm control section 24, and in response to a control signal from the diaphragm control section 24, the diaphragm 25 limits a light flux to be transmitted among light flux irradiated from the lamp 15 to change light quantity. Furthermore, a RGB rotary filter 23 is connected to an RGB rotary filter control section 26 and is rotated at a predetermined rotation speed.

As for operations by the light source section 41 according to the present embodiment, a light flux outputted from the lamp 15 is limited to a predetermined light quantity by the diaphragm 25. The light flux transmitted through the diaphragm 25 passes through the RGB filter 23, and is outputted as respective illumination lights of R/G/B at predetermined time intervals from the light source section 41.

In addition, the respective illumination lights are reflected inside the subject to be examined and received by the CCD 21. Signals obtained at the CCD 21 are sorted according to irradiation time by a switching section (not shown) provided at the endoscope apparatus main body 105, and are respectively inputted to the S/H circuits 433a to 433c.

In other words, when an illumination light is irradiated via the R filter from the light source section 41, a signal obtained by the CCD 21 is inputted to the S/H circuit 433a. Incidentally, since other operations are the same as those in the seventh embodiment, descriptions thereof will be omitted.

According to the present embodiment, in the same manner as in the seventh embodiment, a spectral observation image capable of clearly displaying a vascular pattern can be obtained, and at the same time, living body function information related to the spectral observation image can be displayed.

In addition, unlike the seventh embodiment the present embodiment is able to receive the full benefits of the so-called frame sequential method. Such benefits include those offered by the tenth embodiment that will be described later.

Furthermore, in the embodiment described above, illumination light quantity (light quantity from a light source) is controlled/adjusted in order to avoid saturation of R/G/B color signals. Conversely, there is a method that adjusts an electronic shutter of a CCD. With a CCD, charges accumulate in proportion to light intensity incident in a given time period, whereby the charge quantity is taken as a signal. A component corresponding to a charge accumulation time during which charge is accumulated is called an electronic shutter.

By adjusting the electronic shutter, the accumulated quantity of charges or, in other words, a signal quantity can be adjusted. Therefore, as shown in FIG. 59, by obtaining R/G/B color images in a state where charge accumulation time is sequentially changed, a spectral image similar to that in the case of illumination light quantity control can be obtained.

More specifically, in each of the embodiments described above, illumination light quantity control may be used to obtain a normal image, and when obtaining a spectral image, it is possible to prevent saturation of R/G/B color images by varying the electronic shutter.

Tenth Embodiment

FIG. 60 is a diagram showing charge accumulation time of a CCD according to a tenth embodiment of the present invention.

Since the tenth embodiment is configured almost the same as the ninth embodiment, only differences therebetween will be described. Like components will be assigned like reference characters and descriptions thereof will be omitted.

The present embodiment is primarily similar to the ninth embodiment in the utilization of a frame sequential method, and takes advantage of features thereof. By adding weighting to charge accumulation times due to electronic shutter control according to the ninth embodiment, the present embodiment is able to simplify creation of spectral image data.

In other words, in the present embodiment, a CCD driving circuit 431 capable of varying the charge accumulation time of the CCD 21 is provided. Incidentally, since other components are the same as those in the ninth embodiment, descriptions thereof will be omitted.

As for operations of the present embodiment, as shown in FIG. 60, when respective illumination lights are irradiated via the RGB rotary filter 23, the CCD driving circuit 431 varies the charge accumulation time due to the electronic shutter of the CCD 21.

At this point, let us assume that the respective charge accumulation times of the CCD 21 for R/G/B illumination lights are tdr, tdg and tdb (incidentally, since an accumulation time is not provided for the B color image signal, tdb is omitted in the diagram). For example, when performing the matrix computation represented by Formula 21, since the computation to be performed by the F3 quasi-filter image may be determined from RGB images obtained by a normal endoscope as $$F3 = -0.050R - 1.777G + 0.829B \quad (25)$$

setting the charge accumulation time due to electronic shutter control according to RGB shown in FIG. 60 to $$tdr:tdg:tdb = 0.050:1.777:0.829 \quad (26)$$

shall suffice. In addition, for the matrix portion, a signal in which only the R and G components are inverted as well as the B component are added. As a result, a spectral image similar to that in the seventh to ninth embodiments can be obtained.

According to the present embodiment, in the same manner as in the ninth embodiment, a spectral observation image capable of clearly displaying a vascular pattern can be obtained, and at the same time, living body function information related to the spectral observation image can be displayed. Furthermore, the present embodiment utilizes the frame sequential method for creating color image signals in the same manner as the ninth embodiment, and charge accumulation times can be varied using the electronic shutter for each color image signal. Consequently, the matrix computing section 436 need only perform addition and subtraction processing, thereby enabling simplification of processing.

Eleventh Embodiment

Figure 62:
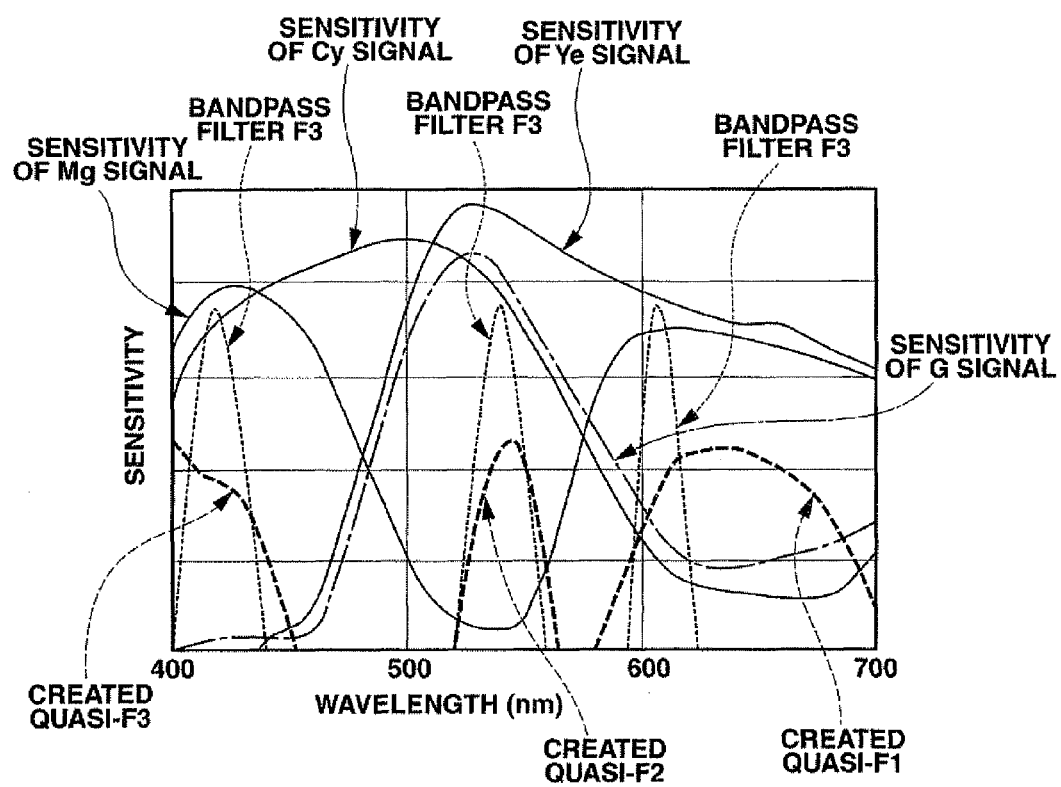
FIG. 62 is a diagram showing spectral sensitivity characteristics of the color filters shown in FIG. 61.

FIGS. 61 and 62 relate to an eleventh embodiment of the present invention, where FIG. 61 is a diagram showing an color filter array and FIG. 62 is a diagram showing spectral sensitivity characteristics of the color filters shown in FIG. 61.

Since the eleventh embodiment is almost the same as the seventh embodiment, only differences therebetween will be described. Like components will be assigned like reference characters and descriptions thereof will be omitted.

The present embodiment primarily differs from the seventh embodiment in the color filters provided at the CCD 21. Compared to the seventh embodiment in which RGB primary color-type color filters are used as shown in FIG. 6, the present embodiment uses complementary type color filters.

As shown in FIG. 61, the array of the complementary type color filters is constituted by the respective elements of G, Mg, Ye and Cy. Incidentally, the respective elements of the primary color-type color filters and the respective elements of the complementary type color filters form relationships of Mg=R+B, Cy=G+B, and Ye=R+G.

In this case, the endoscope apparatus main body 105 performs a full pixel readout from the CCD 21 and signal processing or image processing on the images from the respective color filters. In addition, by transforming Formulas 1 to 8 and 19 to 21 which accommodate primary color-type color filters so as to accommodate complementary type color filters, Formulas 27 to 33 presented below are derived. Note that target narrow bandpass filter characteristics are the same.

$$(G \quad Mg \quad Cy \quad Ye)\begin{pmatrix} a_1 & a_2 & a_3 \\ b_1 & b_2 & b_3 \\ c_1 & c_2 & c_3 \\ d_1 & d_2 & d_3 \end{pmatrix} = (F_1 \quad F_2 \quad F_3) \quad (27)$$

$$C = (G \quad Mg \quad Cy \quad Ye) \quad (28)$$

$$A = \begin{pmatrix} a_1 & a_2 & a_3 \\ b_1 & b_2 & b_3 \\ c_1 & c_2 & c_3 \\ d_1 & d_2 & d_3 \end{pmatrix}$$

$$F = (F_1 \quad F_2 \quad F_3)$$

$$k_G = (\int S(\lambda) \times H(\lambda) \times G(\lambda) d\lambda)^{-1}$$

$$k_{Mg} = (\int S(\lambda) \times H(\lambda) \times Mg(\lambda) d\lambda)^{-1}$$

$$k_{Cy} = (\int S(\lambda) \times H(\lambda) \times Cy(\lambda) d\lambda)^{-1}$$

$$k_{Ye} = (\int S(\lambda) \times H(\lambda) \times Ye(\lambda) d\lambda)^{-1} \quad (29)$$

$$K = \begin{pmatrix} k_G & 0 & 0 & 0 \\ 0 & k_{Mg} & 0 & 0 \\ 0 & 0 & k_{Cy} & 0 \\ 0 & 0 & 0 & k_{Ye} \end{pmatrix} \quad (30)$$

$$A = \begin{pmatrix} -0.413 & -0.678 & 4.385 \\ -0.040 & -3.590 & 2.085 \\ -0.011 & -2.504 & -1.802 \\ 0.332 & 3.233 & -3.310 \end{pmatrix} \quad (31)$$

$$K = \begin{pmatrix} 1 & 0 & 0 & 0 \\ 0 & 0.814 & 0 & 0 \\ 0 & 0 & 0.730 & 0 \\ 0 & 0 & 0 & 0.598 \end{pmatrix} \quad (32)$$

$$A^t = KA \quad (33)$$

$$= \begin{pmatrix} 1 & 0 & 0 & 0 \\ 0 & 0.814 & 0 & 0 \\ 0 & 0 & 0.730 & 0 \\ 0 & 0 & 0 & 0.598 \end{pmatrix} \begin{pmatrix} -0.413 & -0.678 & 4.385 \\ -0.040 & -3.590 & 2.085 \\ -0.011 & -2.504 & -1.802 \\ 0.332 & 3.233 & -3.310 \end{pmatrix}$$

$$= \begin{pmatrix} -0.413 & -0.678 & 4.385 \\ -0.033 & -2.922 & 1.697 \\ -0.008 & -1.828 & -1.315 \\ 0.109 & 1.933 & -1.979 \end{pmatrix}$$

Furthermore, FIG. 62 shows spectral sensitivity characteristics when using complementary type color filters, target bandpass filters, and characteristics of quasi-bandpass filter determined from Formulas 27 to 33 provided above.

It is needless to say that, when using complementary type color filters, the S/H circuits shown in FIG. 51 are respectively applied to G/Mg/Cy/Ye instead of R/G/B.

Moreover, even when using complementary type color filters, the matrix estimation method expressed by Formulas 9 to 18 is applicable. In this case, when the number of complementary type color filters is 4, the portion of the hypothesis of Formula 14 that living body spectral reflectance can be approximated using three fundamental spectral characteristics now becomes four, or four or less. Therefore, accordingly, a dimension for computing the estimation matrix is changed from 3 to 4.

According to the present embodiment, in the same manner as in the seventh embodiment, a spectral observation image capable of clearly displaying a vascular pattern can be obtained, and at the same time, living body function information related to the spectral observation image can be displayed. In addition, the present embodiment is able to receive the full benefit of using complementary type color filters.

While various embodiments according to the present invention have been described above, the present invention allows various combinations of the embodiments described above to be used. In addition, modifications may be made without departing from the scope thereof.

For example, for all previously described embodiments, the operator can create a new quasi-bandpass filter during clinical practice or at other timings and apply the filter to clinical use. In other words, with respect to the seventh embodiment, a designing section (not shown) capable of computing/calculating matrix coefficients may be provided at the control section 42 shown in FIG. 51.

Accordingly, a quasi-bandpass filter suitable for obtaining a spectral image desired by the operator may be arranged to be newly designed by inputting a condition via the keyboard provided on the endoscope apparatus main body 105 shown in FIG. 3. Accordingly, immediate clinical application can be achieved by setting a final matrix coefficient (corresponding to the respective elements of matrix <A'> in Formulas 21 and 33) derived by applying a correction coefficient (corresponding to the respective elements of matrix <K> in Formulas 20 and 32) to the calculated matrix coefficient (corresponding to the respective elements of matrix <A> in Formulas 19 and 31) to the matrix computing section 436 shown in FIG. 51.

Figure 63:
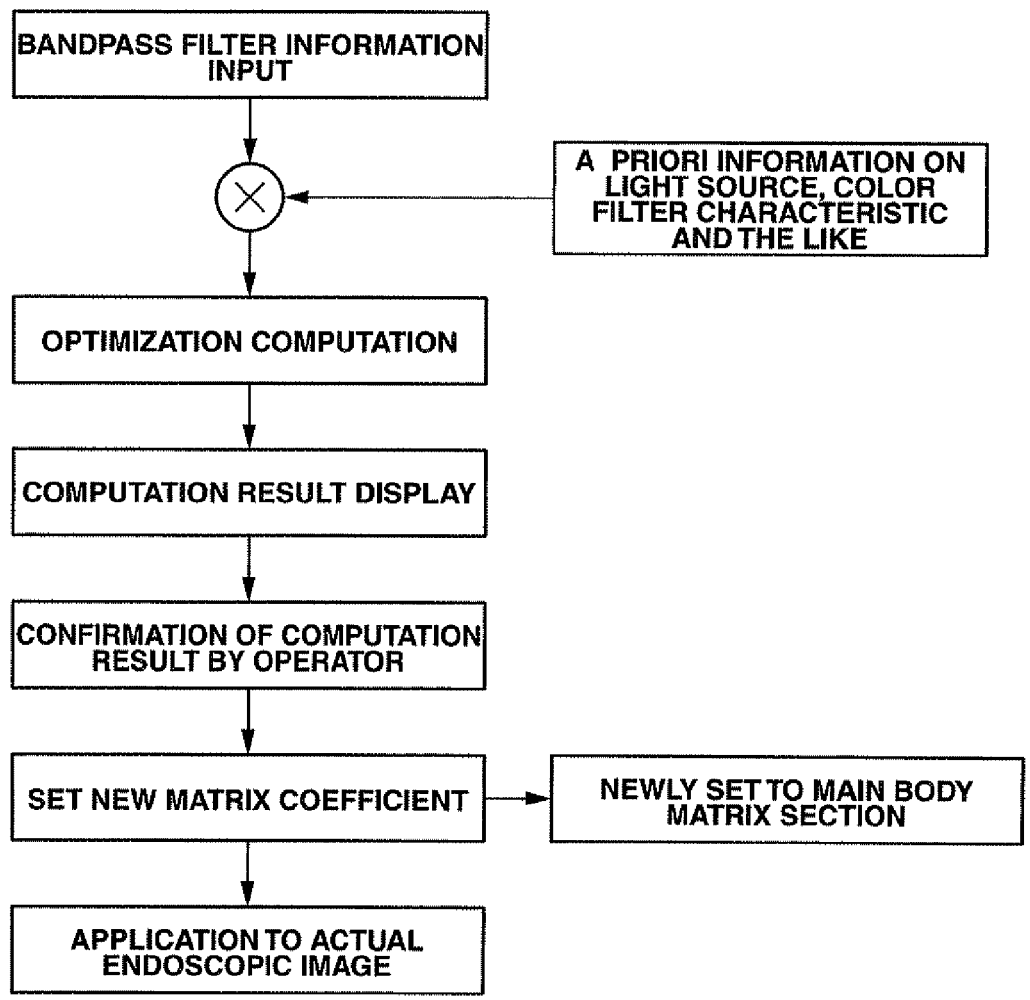
FIG. 63 is a flowchart during matrix computation according to a modification of the present invention.

FIG. 63 shows a flow culminating in clinical application. To describe the flow in specific terms, first, the operator inputs information (e.g., wavelength band or the like) on a target bandpass filter via a keyboard or the like. In response thereto, a matrix <A'> is calculated together with characteristics of a light source, color filters of a CCD or the like stored in advance in a predetermined storage device or the like, and, as shown in FIG. 62, characteristics of the target bandpass filter as well as a computation result (quasi-bandpass filter) by the matrix <A'> are displayed on a monitor as spectrum diagrams.

After confirming the computation result, the operator performs settings accordingly when using the newly created matrix <A'>, and an actual endoscopic image is created using the matrix <A'>. At the same time, the newly created matrix <A'> is stored in a predetermined storage device, and can be reused in response to a predetermined operation by the operator.

As a result, irrespective of an existing matrix <A'>, the operator can create a new bandpass filter based on personal experience or the like. This is particularly effective when used for research purposes.

The present invention is not limited to the embodiments described above, and various changes and modifications may be made without departing from the scope thereof.

INDUSTRIAL APPLICABILITY

By creating a spectral image signal (spectral signal) from a color image signal (living body signal) through electric signal processing and by further providing color tone adjusting means and coefficient switching means, a state of high reliability can be maintained even when a different biological tissue is to be observed, and image display can be performed in a state of favorable operability.

The present application is based on Japanese Patent Application No. 2005-140379 filed May 12, 2005 in Japan and on Japanese Patent Application No. 2005-140383 filed May 12, 2005 in Japan, the disclosed contents of which are incorporated into the present specification, the scope of claims and the drawings by reference.

The invention claimed is:

1. A biological observation apparatus comprising:
a color image signal creator that performs signal processing on either a first image pickup signal for which a subject to be examined illuminated by white illumination light is picked up by a first image pickup apparatus provided with a color filter having a transmitting characteristic of a plurality of broadband wavelengths or a second image pickup signal for which a subject to be examined illuminated by a plurality of mutually different frame sequential illumination lights in a broadband wavelength range which covers a visible range is picked up by a second image pickup apparatus, and creates a color image signal for display as a color image on a display device;
a spectral image signal creator that creates, based on the first image pickup signal or the second image pickup signal, a spectral image signal corresponding to a narrowband image signal obtained upon picking up an image of a subject to be examined illuminated by an illumination light in a narrowband wavelength range through signal processing of a color signal used to create the color image signal or through signal processing of the color image signal;
a display color convertor that performs display color conversion on the spectral image signal when displaying the signal as a spectral image on the display device;
at least one of a characteristic changer/setter that changes/sets creating characteristics of the spectral image signal at the spectral image signal creator, a display color changer/setter that changes/sets a display color convertor, and an interface for performing instruction operations for switching and confirming information including images displayed on the display device;
a brightness judger that outputs a judgment signal when a brightness in the spectral image signal is equal to or lower than a reference value,
wherein the display color changer/setter comprises a coefficient storer that stores a plurality of conversion coefficients for changing characteristics of the display color conversion and a coefficient switch/setter that switches and sets a conversion coefficient to be used for conversion of a conversion coefficient to be used for display color conversion by the display color convertor,
wherein the plurality of conversion coefficients stored in the coefficient storer includes a feature value coefficient corresponding to a plurality of feature values having different spectral reflection characteristics of a living body as the subject to be examined,
wherein the different spectral reflection characteristics are expressed as a linear sum of three elementary spectral characteristics, the spectral image signal is created by performing approximation to express with a single number value the spectral characteristics of the living body in each wavelength of different narrowband regions of each wavelength, and
wherein the brightness judger switches an image displayed on the display device from the spectral image to the color image based on the judgment signal.

2. The biological observation apparatus according to claim 1, comprising a light source that emits the illumination light used for picking up images by the first image pickup apparatus or the second image pickup apparatus.

3. The biological observation apparatus according to claim 1, wherein the first image pickup apparatus or the second image pickup apparatus is provided at an endoscope, and comprising a connector to which the endoscope is detachably connected.

4. The biological observation apparatus according to claim 1, wherein the characteristic changer/setter automatically or manually changes/sets the creating characteristics of the characteristic changer/setter based on information corresponding to at least one of the first image pickup apparatus or the second image pickup apparatus and the light source that emits the illumination light used for picking up images by the first image pickup apparatus or the second image pickup apparatus.

5. The biological observation apparatus according to claim 1, wherein the spectral image signal creator includes a second coefficient storer that stores a plurality of coefficients that changes creating characteristics of the spectral image signals, and the characteristic changer/setter switches/sets a coefficient to be used for changing/setting the creating characteristics with respect to the second coefficient storer.

6. The biological observation apparatus according to claim 5, wherein the plurality of coefficients stored in the second coefficient storer includes a plurality of biological coefficients corresponding to spectral reflection characteristics of the living body, or a name of an observation target region in the living body, or a type of mucosal tissue of the living body.

7. The biological observation apparatus according to claim 5, wherein the plurality of coefficients stored in the second coefficient storer include a plurality of feature value coefficients that change creating characteristics of the spectral image signal in correspondence to a plurality of different feature values of the living body.

8. The biological observation apparatus according to claim 7, wherein the feature value coefficient is set to a vascular coefficient that creates the spectral image signal for observing a vascular structure distributed in a depth-wise direction from a surface of the living body.

9. The biological observation apparatus according to claim 1, wherein the feature value coefficient is set to a vascular coefficient that sets a display color of the spectral image signal for observing a vascular structure distributed in a depth-wise direction from a surface of the living body.

10. The biological observation apparatus according to claim 1, further comprising a brightness judger that judges whether a brightness in the spectral image signal is equal to or lower than a reference value, and switches creating characteristics of the spectral image signal in accordance with a judgment result by the brightness judger.

11. The biological observation apparatus according to claim 1, further comprising a color tone judger that judges whether the spectral image signal corresponds to a predetermined color tone value, and switches creating characteristics of the spectral image signal in accordance with a judgment result by the color tone judger.

12. The biological observation apparatus according to claim 1, wherein the characteristic changer/setter includes a light source type/spectral characteristic detector that detects at least either a type of light source mounted on a light source that emits the illumination light or a spectral characteristic difference thereof, and changes creating characteristics of the spectral image signal according to a detection result by the light source type/spectral characteristic detector.

13. The biological observation apparatus according to claim 1, wherein the interface includes a display state controller that controls a display state of at least either the color image or the spectral image to be displayed in the display device.

14. The biological observation apparatus according to claim 13, wherein the display state controller includes a display selector that selects at least either simultaneous display of both the color image and the spectral image to be displayed on the display device or a display of only one of the images.

15. The biological observation apparatus according to claim 13, wherein the display state controller includes an image size changer that changes an image size of the color image and the spectral image when displayed on the display device, and the color image and the spectral image in an image size changed by the image size changer is outputtable to the display device.

16. The biological observation apparatus according to claim 15, wherein the observation image mode setter sets an observation image to be displayed on the display device upon power activation of the biological observation apparatus to either the color image or the spectral image based on a selection operation from the observation image selector.

17. The biological observation apparatus according to claim 15, wherein the observation image mode setter switches, in conjunction with a selection of the color image or the spectral image, a parameter of at least either a signal processor that includes the color image signal creator and the spectral image signal creator that are used when outputting either the color image or the spectral image to the display device or a light source that generates the illumination light.

18. The biological observation apparatus according to claim 1, comprising an observation image mode setter including: an observation image selector that performs selection for causing one of the color image and the spectral image to be displayed on the display device as an observation image to be observed by a user; and a controller that performs control so that the color image signal creator or the spectral image signal creator enters an active state so that at least the image selected by the observation image selector is created.

19. The biological observation apparatus according to claim 1, wherein the observation image mode setter includes an observation image information display that displays information related to an observation image to be displayed on the display device.

20. The biological observation apparatus according to claim 19, wherein the observation image information display explicitly displays, on the display device, that an observation image displayed on the display device is either the color image or the spectral image.

21. The biological observation apparatus according to claim 19, wherein the observation image information display explicitly displays, on the interface provided on the biological observation apparatus for the user to perform instruction operations, that an observation image displayed on the display device is either the color image or the spectral image.

22. A biological observation apparatus comprising:
a color image signal creator that performs signal processing on either a first image pickup signal for which a subject to be examined illuminated by white illumination light is picked up by a first image pickup apparatus provided with a color filter having a transmitting characteristic of a plurality of broadband wavelengths or a second image pickup signal for which a subject to be examined illuminated by a plurality of mutually different frame sequential illumination lights in a broadband wavelength range which covers a visible range is picked up by a second image pickup apparatus, and creates a color image signal for display as a color image on a display device;
a spectral image signal creator that creates, based on the first image pickup signal or the second image pickup signal, a spectral image signal corresponding to a narrowband image signal obtained upon picking up an image of a subject to be examined illuminated by an illumination light in a narrowband wavelength range through signal processing of a color signal used to create the color image signal or through signal processing of the color image signal;
a display color convertor that performs display color conversion on the spectral image signal when displaying the signal as a spectral image on the display device;
at least one of a characteristic changer/setter that changes/sets creating characteristics of the spectral image signal at the spectral image signal creator, a display color changer/setter that changes/sets a display color convertor, and an interface for performing instruction operations for switching and confirming information including images displayed on the display device; and
a particular color tone value detector that detects a particular color tone value of the color tone of the spectral image signal when at least one of a staining dye, residue and bile exists in the subject to be examined,
wherein the display color changer/setter comprises a coefficient storer that stores a plurality of conversion coefficients for changing characteristics of the display color conversion and a coefficient switch/setter that switches and sets a conversion coefficient to be used for conversion of a conversion coefficient to be used for display color conversion by the display color convertor,
wherein the plurality of conversion coefficients stored in the coefficient storer includes a feature value coefficient corresponding to a plurality of feature values having different spectral reflection characteristics of a living body as the subject to be examined, and
wherein the different spectral reflection characteristics are expressed as a linear sum of three elementary spectral characteristics, the spectral image signal is created by performing approximation to express with a single number value the spectral characteristics of the living body in each wavelength of different narrowband regions of each wavelength,
and when the particular color tone value detected by the particular color tone value detector is equal to or greater than a predetermined quantity, the spectral image to be displayed on the display device is switched to the color image.

* * * * *